United States Patent
Dietz et al.

(10) Patent No.: US 11,273,148 B2
(45) Date of Patent: Mar. 15, 2022

(54) TARGETED EPIGENETIC THERAPY FOR INHERITED AORTIC ANEURYSM CONDITION

(71) Applicant: The Johns Hopkins University, Baltimore, MD (US)

(72) Inventors: Harry C. Dietz, Towson, MD (US); Benjamin Edward Kang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/643,522

(22) PCT Filed: Aug. 31, 2018

(86) PCT No.: PCT/US2018/049217
§ 371 (c)(1),
(2) Date: Feb. 28, 2020

(87) PCT Pub. No.: WO2019/046791
PCT Pub. Date: Mar. 7, 2019

(65) Prior Publication Data
US 2020/0253932 A1 Aug. 13, 2020

Related U.S. Application Data

(60) Provisional application No. 62/553,394, filed on Sep. 1, 2017.

(51) Int. Cl.
*A61K 31/4155* (2006.01)
*A61P 9/14* (2006.01)

(52) U.S. Cl.
CPC ............ *A61K 31/4155* (2013.01); *A61P 9/14* (2018.01)

(58) Field of Classification Search
CPC .............................. A61K 31/4155; A61P 9/14
See application file for complete search history.

(56) References Cited

U.S. PATENT DOCUMENTS

| | | |
|---|---|---|
| 5,283,173 A | 2/1994 | Fields et al. |
| 5,288,514 A | 2/1994 | Ellman |
| 5,468,614 A | 11/1995 | Fields et al. |
| 5,474,796 A | 12/1995 | Brennan |
| 5,525,490 A | 6/1996 | Erickson et al. |
| 5,539,083 A | 7/1996 | Cook et al. |
| 5,605,662 A | 2/1997 | Heller et al. |
| 5,637,463 A | 6/1997 | Dalton et al. |
| 5,667,973 A | 9/1997 | Fields et al. |
| 8,697,359 B1 | 4/2014 | Zhang |
| 2004/0021533 A1 | 2/2004 | Okazaki et al. |
| 2004/0038284 A1 | 2/2004 | Markowitz et al. |
| 2004/0215338 A1 | 10/2004 | Elkins et al. |
| 2017/0107218 A1 | 4/2017 | Zhou et al. |

FOREIGN PATENT DOCUMENTS

| | | |
|---|---|---|
| EP | 1479402 B1 | 8/2011 |
| WO | 84/03564 A1 | 9/1984 |
| WO | 91/19735 A1 | 12/1991 |
| WO | 92/00091 A1 | 1/1992 |
| WO | 93/20242 A1 | 10/1993 |
| WO | 95/25116 A1 | 9/1995 |
| WO | 95/35505 A1 | 12/1995 |
| WO | 2007/050793 A3 | 1/2008 |
| WO | 2008/033408 A3 | 12/2008 |
| WO | 2011/041545 A1 | 4/2011 |
| WO | 2019/046791 A1 | 3/2019 |

OTHER PUBLICATIONS

Akhurst (Jul. 27, 2012) "The Paradoxical TGF-B Vasculopathies", Nature Genetics, 44(8):4 Pages.

Akiyoshi et al. (Dec. 3, 1999) "c-Ski Acts as a Transcriptional Co-repressor in Transforming Growth Factor-b Signaling through Interaction with Smads", The Journal Of Biological Chemistry, 247(49):35269-35277.

Attenhofer Jost et al. (2014) "Medical Treatment of Aortic Aneurysms in Marfan Syndrome and other Heritable Conditions", Current Cardiology Reviews, 10(2):161-171.

Au et al. (Dec. 19, 2013) "De Novo Exon 1 Missense Mutations of SKI and Shprintzen-Goldberg Syndrome: Two New Cases and a Clinical Review", American Journal of Medical Genetics, 164A:676-684.

Campbell et al. (1994) "Phosphonate Ester Synthesis Using a Modified Mitsunobu Condensation", The Journal of Organic Chemistry, 59(3):658-660.

Carmignac et al. (Nov. 2, 2012) "In-Frame Mutations in Exon 1 of SKI Cause Dominant Shprintzen-Goldberg Syndrome", The American Journal of Human Genetics, 91:950-957.

Chabala (1995) "Solid-Phase Combinatorial Chemistry and Novel Tagging Methods for Identifying Leads", Current Opinion in Biotechnology, 6:632-639.

Chen et al. (1994) "Analogous Organic Synthesis of Small-Compound Libraries: Validation of Combinatorial Chemistry in Small-Molecule Synthesis", Journal of American Chemical Society, 116(6):2661-2662.

Chen et al. (Apr. 13, 2007) "Competition between Ski and CREB-binding Protein for Binding to Smad Proteins in Transforming Growth Factor-Beta Signaling", The Journal of Biological Chemistry, 282(15):11365-11376.

Chen et al. (Oct. 26, 2014) "SREBP-1 is a Novel Mediator of TGFβ1 Signaling in Mesangial Cells", Journal of Molecular Cell Biology, 6(6):516-530.

(Continued)

*Primary Examiner* — Brenda L Coleman
(74) *Attorney, Agent, or Firm* — Mintz Levin Cohn Ferris Glovsky and Popeo, P.C.; Peter F. Corless

(57) ABSTRACT

Transforming growth factor β (TGFβ) transcriptional responses are involved in the pathogenesis of aortic aneurism syndromes. Compositions that inhibit histone acetyl-transferase activity normalize gene expression in the aorta, preserved aortic wall architecture and abrogated aneurism progression. Methods include the use of these compositions to epigenetically regulate abnormal expression and/or activity of TGFβ genes.

8 Claims, 27 Drawing Sheets

Specification includes a Sequence Listing.

(56) References Cited

OTHER PUBLICATIONS

Chien et al. (Nov. 1991) "The Two-Hybrid System: A Method to Identify and Clone Genes for Proteins that Interact with a Protein of Interest", Proceedings of the National Academy of Sciences of the United States of America, 88:9578-9582.
Cho et al. (Sep. 3, 1993) "An Unnatural Biopolymer", Science, 261(5126):1303-1305.
Courtois et al. (Feb. 7, 2017) "A Novel SMAD3 Mutation Caused Multiple Aneurysms In A Patient Without Osteoarthritis Symptoms", European Journal of Medical Genetics, 60:228-231.
Dang et al. (Feb. 1991) "Intracellular Leucine Zipper Interactions Suggest c-Myc Hetero-Oligomerization", Molecular and Cellular Biology, 11(2):954-962.
Dewitt et al. (Aug. 1993) "Diversomers: An Approach to Nonpeptide, Nonoligomeric Chemical Diversity", Proceedings of the National Academy of Sciences, 90(15):6909-6913.
Dias et al. (Dec. 19, 2015) "Methylation of RNA Polymerase II Non-Consensus Lysine Residues Marks Early Transcription in Mammalian Cells Identifying", eLife, 4:30 Pages.
Dolle (1996) "Discovery of Enzyme Inhibitors Through Combinatorial Chemistry", Molecular Diversity, 2:223-236.
Doyle et al. (Oct. 27, 2015) "A Deleterious Gene-by-Environment Interaction Imposed by Calcium Channel Blockers in Marfan Syndrome", eLife, e08648, 4:18 Pages.
Doyle et al. (Nov. 2012) "Mutations in the TGF-α Repressor SKI Cause Shprintzen-Goldberg Syndrome with Aortic Aneurysm", Nature Genetics, 44(11):16 Pages.
Drinnenberg et al. (Oct. 23, 2009) "RNAi in Budding Yeast", Science, 326(5952):14 Pages.
Eguchi et al. (1991) "Antisense RNA", Annual Review of Biochemistry, 60:631-652.
Eichler et al. (Jul. 1995) "Generation and Utilization of Synthetic Combinatorial Libraries", Molecular Medicine Today, 1(4):174-180.
Eichler et al. (1995) "Peptide, Peptidomimetic, and Organic Synthetic Combinatorial Libraries", Medicinal Research Reviews, 15(6):481-496.
Fauchere et al. (1997) "Peptide and Nonpeptide Lead Discovery Using Robotically Synthesized Soluble Libraries", Canadian Journal of Physiology and Pharmacology, 75:683-689.
Fearon et al. (Sep. 1992) "Karyoplasmic Interaction Selection Strategy: A General Strategy to Detect Protein-Protein Interactions in Mammalian Cells", Proceedings of the National Academy of Sciences of the United States of America, 89:7958-7962.
Fields et al. (Jul. 20, 1989) "A Novel Genetic System to Detect Protein-Protein Interactions", Nature, 340:245-246.
Fodor et al. (Feb. 15, 1991) "Light-Directed, Spatially Addressable Parallel Chemical Synthesis", Science, 251(4995):767-773.
Frank et al. (1988) "Simultaneous Multiple Peptide Synthesis under Continuous Flow Conditions on Cellulose Paper Discs as Segmental Solid Supports", Tetrahedron, 44(19):6031-6040.
Gallo et al. (Jan. 2014) "Angiotensin II-dependent TGF-β Signaling Contributes to Loeys-Dietz Syndrome Vascular Pathogenesis", The Journal of Clinical Investigation, 124(1):448-460.
Geysen et al. (1987) "Strategies for Epitope Analysis using Peptide Synthesis", Journal of Immunological Methods, 102:259-274.
Groenink et al. (Sep. 2, 2013) "Losartan Reduces Aortic Dilatation Rate in Adults with Marfan Syndrome: A Randomized Controlled Trial", European Heart Journal, 34:3491-3500.
Habashi et al. (Apr. 15, 2011) "Angiotensin II Type 2 Receptor Signaling Attenuates Aortic Aneurysm in Mice Through ERK Antagonism", Science, 332(6027):8 Pages.
Habashi et al. (Apr. 7, 2006) "Losartan, an AT1 Antagonist, Prevents Aortic Aneurysm in a Mouse Model of Marfan Syndrome", Science, 312(5770):12 Pages.
Hagihara et al. (1992) "Vinylogous Polypeptides: An Alternative Peptide Backbone", Journal of American Chemical Society, 114(16):6568-6570.

Hayashi et al. (Jun. 24, 2015) "Renin-Angiotensin Blockade Resets Podocyte Epigenome through Kruppel-Like Factor 4 and Attenuates Proteinuria", Kidney International, 88:745-753.
He et al. (Sep. 2015) "KLF4 Mediates the Link Between TGF-B1-Induced Gene Transcription and H3 Acetylation in Vascular Smooth Muscle Cells", The FASEB Journal, 29(9):4059-4070.
Heller et al. (Mar. 1997) "Discovery and Analysis of Inflammatory Disease-Related Genes Using cDNA Microarrays", PNAS, 94: 2150-2155.
Hirschmann et al. (1992) "The First Design and Synthesis of a Steroidal Peptidomimetic. The Potential Value of Peptidomimetics in Elucidating the Bioactive Conformation of Peptide Ligands", Journal of the American Chemical Society, 114(24):9699-9701.
Holm et al. (Apr. 15, 2011) "Noncanonical TGFβ Signaling Contributes to Aortic Aneurysm Progression in Marfan Syndrome Mice", Science, 332(6027):9 Pages.
Huang et al. (Jan. 9, 2017) "CIL-102-Induced Cell Cycle Arrest and Apoptosis in Colorectal Cancer Cells via Upregulation of p21 and GADD45", PLOS One, 12(1):17 Pages.
Isselbacher et al. (Jun. 14, 2016) "Hereditary Influence in Thoracic Aortic Aneurysm and Dissection", Circulation, 133(24):28 Pages.
Janda (Nov. 1994) "Tagged Versus Untagged Libraries: Methods for the Generation and Screening of Combinatorial Chemical Libraries", PNAS, 91(23):10779-10785.
Jinek et al. (Jan. 22, 2009) "A Three-Dimensional View of the Molecular Machinery of RNA Interference", Nature, 457:405-412.
Judge et al. (Jul. 2004) "Evidence for a Critical Contribution of Haploinsufficiency in the Complex Pathogenesis of Marfan Syndrome", The Journal of Clinical Investigation, 114(2):172-181.
Kenan et al. (Feb. 1994) "Exploring Molecular Diversity with Combinatorial Shape Libraries", Trends in biochemical sciences, 19(2):57-64.
Kim et al. (Jan. 2, 2017) "Genetic and Epigenetic Regulation of Aortic Aneurysms", BioMed Research International, Article ID 7268521, 2017:12 Pages.
Kozal et al. (Jul. 1996) "Extensive Polymorphisms Observed in HIV-1 Clade B Protease Gene using High-Density Oligonucleotide Arrays", Nature Medicine, 2(7):753-759.
Lebl et al. (1995) "One-Bead-One-Structure Combinatorial Libraries", Biopolymers (Peptide Science), 37:177-198.
Liang et al. (Nov. 29, 1996) "Parallel Synthesis and Screening of a Solid Phase Carbohydrate Library", Science, 274(5292):1520-1522.
Lin et al. (2010) "TGF-β Signaling in Aortic Aneurysm: Another Round of Controversy", Journal Of Genetics And Genomics, 37:583-591.
Haldar, et al., "Klf15 Deficiency is a Molecular Link Between Heart Failure and Aortic Aneurysm Formulation," Science Translation Medicine, 2010, vol. 2, No. 26, pp. 1-22.
Stratton, et al., "Epigenetic Regulation of Cardiac Fibrosis," Journal of Molecular and Cellular Cardiology, 2016, vol. 92, pp. 1-20.
International Search Report issued in corresponding International Application No. PCT/US2018/049217, dated Dec. 10, 2018 (4 pages).
Written Opinion issued in corresponding International Application No. PCT/US2018/049217, dated Dec. 10, 2018 (7 pages).
Lindsay et al. (Aug. 1, 2012) "Loss-of-Function Mutations in TGFB2 Cause A Syndromic Presentation of Thoracic Aortic Aneurysm", Nature Genetics, 44(8):18 Pages.
Liu et al. (2001) "Ski/Sno and TGF-β signaling", Cytokine and Growth Factor Reviews, 12:1-8.
Luo et al. (1999) "The Ski Oncoprotein Interacts with the Smad Proteins to Repress Tgfb Signaling", Genes & Development, 13:2196-2206.
Maddox et al. (2013) "p300/CBP Histone Acetyltransferase Activity is Required for Newly Acquired and Reactivated Fear Memories in the Lateral Amygdala", Learning & Memory, 20:109-119.
Makarova et al. (Aug. 25, 2009) "Prokaryotic Homologs of Argonaute Proteins are Predicted to Function as Key Components of a Novel System of Defense Against Mobile Genetic Elements", Biology Direct, 4:15 Pages.
Manzo et al. (Apr. 26, 2009) "Histone Acetyltransferase Inhibitors and Preclinical Studies", Expert Opinion on Therapeutic Patents, 19(6):761-774.

(56) References Cited

OTHER PUBLICATIONS

Marek et al. (May 18, 2011) "Paradoxical Enhancement of Fear Extinction Memory and Synaptic Plasticity by Inhibition of the Histone Acetyltransferase p300", The Journal of Neuroscience, 31(20):7486-7491.
Merrifield (Jul. 20, 1963) "Solid Phase Peptide Synthesis. I. The Synthesis of a Tetrapeptide", Journal of the American Chemical Society, 85(14):2149-2154.
Molloy (Nov. 2013) "Bacterial Physiology: Bacterial Argonaute Sets Sail", Nature Reviews Microbiology, 11(11):1 Page.
Olovnikov et al. (Sep. 12, 2013) "Bacterial Argonaute Samples the Transcriptome to Identify Foreign DNA", Molecular Cell, 51(5):21 Pages.
Petruk et al. (Nov. 26, 2013) "Stepwise Histone Modifications are Mediated by Multiple Enzymes that Rapidly Associate with Nascent DNA During Replication", Nature Communications, 4:9 Pages.
Reddy et al. (Feb. 2014) "Losartan Reverses Permissive Epigenetic Changes in Renal Glomeruli of Diabetic Db/Db Mice", Kidney International, 85(2):24 Pages.
Robinson et al. (2005) "Shprintzen-Goldberg Syndrome: Fourteen New Patients and a Clinical Analysis", American Journal of Medical Gene, 135A:251-262.
Salomon et al. (Jul. 2, 2015) "Single-Molecule Imaging Reveals that Argonaute Reshapes the Binding Properties of Its Nucleic Acid Guides", Cell, 162(1):27 Pages.
Santer et al. (Jun. 27, 2011) "Inhibition of the Acetyltransferases p300 and CBP Reveals a Targetable Function for p300 in the Survival and Invasion Pathways of Prostate Cancer Cell Lines", Molecular Cancer Therapeutics, 10(9):1644-1655.
Schena et al. (Oct. 1996) "Parallel Human Genome Analysis: Microarray-Based Expression Monitoring of 1000 Genes", PNAS, 93:10614-10619.
Schepers et al. (Apr. 16, 2014) "The SMAD-Binding Domain of SKI: A Hotspot for De Novo Mutations Causing Shprintzen-Goldberg Syndrome", European Journal of Human Genetics, 23:224-228.
Schiffer et al. (Jun. 20, 2012) "Targeted DNA Mutagenesis for the Cure of Chronic Viral Infections", Journal of Virology, 86(17):8920-8936.
Sheldon et al. (1993) "C-Reactive Protein and its Cytokine Mediators in Intensive-Care Patients", Clinical Chemistry, 39(1):147-150.
Stroschein et al. (Oct. 22, 1999) "Negative Feedback Regulation of TGF-β Signaling by the SnoN Oncoprotein", Science, 286(5440):771-774.
Sun et al. (Oct. 1999) "Interaction of the Ski Oncoprotein with Smad3 Regulates TGF-b Signaling", Molecular Cell, 4:499-509.
Swarts et al. (Apr. 29, 2015) "Argonaute of the Archaeon Pyrococcus Furiosus is a DNA-Guided Nuclease that Targets Cognate DNA", Nucleic Acids Research, 43(10):5120-5129.

Swarts et al. (Mar. 13, 2014) "DNA-Guided DNA Interference by a Prokaryotic Argonaute", Nature, 507(7491):17 pages.
Swarts et al. (Sep. 2014) "The Evolutionary Journey of Argonaute Proteins", Nature Structural & Molecular Biology, 21(9):31 Pages.
Thompson et al. (1996) "Synthesis and Applications of Small Molecule Libraries", Chemical Reviews, 96:555-600.
Tolia et al. (Jan. 2007) "Slicer and the Argonautes", Nature Chemical Biology, 3(1):36-43.
Van De Laar et al. (Feb. 2011) "Mutations in SMAD3 Cause a Syndromic Form of Aortic Aneurysms and Dissections with Early-Onset Osteoarthritis", Nature Genetics, 43(2):121-126.
Vasavada et al. (Dec. 1991) "A Contingent Replication Assay for the Detection of Protein-Protein Interactions in Animal Cells", Proceedings of the National Academy of Sciences of the United States of America, 88:10686-10690.
Vaughan et al. (Mar. 1996) "Human Antibodies with Sub-nanomolar Affinities Isolated from a Large Non-immunized Phage Display Library", Nature Biotechnology, 14(3):309-314.
Vogel (May 30, 2014) "A Bacterial Seek-and-Destroy System for Foreign DNA", Science, 344(6187):972-973.
Wang et al. (Dec. 2009) "Solution Structure and Functional Analysis of the Influenza B Proton Channel", Nature Structural & Molecular Biology, 16(12):16 Pages.
Wang et al. (Dec. 18, 2008) "Structure of an Argonaute Silencing Complex with a Seed-containing Guide DNA and Target RNA Duplex", Nature, 456(7224):14 Pages.
Wang et al. (Nov. 13, 2008) "Structure of the Guide-Strand-Containing Argonaute Silencing Complex", Nature, 456(7219):14 Pages.
Wu et al. (Nov. 1, 2002) "Structural Mechanism of Smad4 Recognition by the Nuclear Oncoprotein Ski: Insights on Ski-Mediated Repression of TGF-β Signaling", Cell, 111:357-367.
Xu et al. (May 23, 2000) "Ski Acts as a Co-Repressor with Smad2 and Smad3 to Regulate the Response to Type β Transforming Growth Factor", Proceedings of the National Academy of Sciences of the United States of America, 97(11):5924-5929.
Yuan et al. (Dec. 12, 2012) "Involvement of p300/CBP and Epigenetic Histone Acetylation in TGF-β1-mediated Gene Transcription in Mesangial Cells", The American Journal of Physiology—Renal Physiology, 304:F601-F613.
Zhang et al. (2013) "A Dynamic H3K27ac Signature Identifies VEGFA-Stimulated Endothelial Enhancers and Requires EP300 Activity", Genome Research, 23:917-927.
Zhu et al. (Jul. 25, 2013) "576 Kb Deletion in 1p36.33-P36.32 Containing SKI is associated with Limb Malformation, Congenital Heart Disease and Epilepsy", Gene, 528:352-355.
Ziganshin et al. (Mar. 5, 2015) "Atenolol versus Losartan in Marfan's Syndrome", The New England Journal of Medicine, 372(10):977-981.

* $P<0.05$  $P<0.01$ * $P<0.001$ + $P<10^{-4}$ ++ $P<10^{-6}$

SEQUENCE LISTING

```
<160> NUMBER OF SEQ ID NOS: 6

<210> SEQ ID NO 1
<211> LENGTH: 21
<212> TYPE: DNA
<213> ORGANISM: Mus musculus

<400> SEQUENCE: 1
gagcccgatc gcaccatgga a                                       21

<210> SEQ ID NO 2
<211> LENGTH: 20
<212> TYPE: DNA
<213> ORGANISM: Mus musculus

<400> SEQUENCE: 2
aagagatggt ctccccttcc                                         20

<210> SEQ ID NO 3
<211> LENGTH: 20
<212> TYPE: DNA
<213> ORGANISM: Mus musculus

<400> SEQUENCE: 3
agggaagcca aactttttcc                                         20

<210> SEQ ID NO 4
<211> LENGTH: 20
<212> TYPE: DNA
<213> ORGANISM: Mus musculus

<400> SEQUENCE: 4
gagactcttt gtgcaaaaga                                         20

<210> SEQ ID NO 5
<211> LENGTH: 20
<212> TYPE: DNA
<213> ORGANISM: Mus musculus

<400> SEQUENCE: 5
ggaggtggag atggactgta                                         20

<210> SEQ ID NO 6
<211> LENGTH: 20
<212> TYPE: DNA
<213> ORGANISM: Mus musculus

<400> SEQUENCE: 6
cggcattaac tctgtactgt                                         20
```

TARGETED EPIGENETIC THERAPY FOR INHERITED AORTIC ANEURYSM CONDITION

CROSS REFERENCE TO RELATED APPLICATIONS

The present application is a national stage application, filed under 35 U.S.C. § 371 of International Application No. PCT/US2018/049217, filed Aug. 31, 2018, which claims the benefit U.S. provisional application 62/553,394, filed Sep. 1, 2017. The entire contents of these applications are incorporated herein by reference in their entirety.

INCORPORATION BY REFERENCE OF SEQUENCE LISTING

The instant application contains a Sequence Listing which has been filed electronically in ASCII format and is hereby incorporated by reference in its entirety. Said ASCII copy, created on Oct. 30, 2018, is named 048317-545001WO_SEQUENCE_LISTING_ST235.TXT and is 4,096 bytes in size.

FIELD OF THE INVENTION

Embodiments are directed to methods and compositions for the prevention and treatment of inherited aortic aneurysm conditions by epigenetic modulation of transforming growth factor β target genes.

BACKGROUND

Acute aortic syndromes comprise classic aortic dissection, IMH, and penetrating atherosclerotic ulcer (Coady M A, et al. *Cardiol Clin.* 1999; 17(4):637-657). The aortic wall consists of 3 layers (tunica intima, tunica media, and adventitia). Acute aortic dissection (AAD) is presumed to occur when an intimal tear develops, permitting entry of blood to a diseased underlying media characterized by elastic degeneration and smooth muscle cell loss. Chronic acquired conditions, such as systemic arterial hypertension, sometimes in combination with atherosclerosis, cause thickening and fibrosis of the intimal layer and degradation and apoptosis of smooth muscle cells in the media. These processes lead to necrosis and fibrosis of the elastic components of the arterial wall, which in turn produce wall stiffness and weakness, from which dissection and rupture may arise. Because of the high pressure of blood flow in the aorta and thus through the intimal tear, a second or "false" lumen is created, which has the potential for rapid expansion to the outer aspect of the aortic media and which may propagate proximally or distally (Svensson L G, Crawford E S. *Cardiovascular and Vascular Disease of the Aorta* Philadelphia, Pa.: W B Saunders Co; 1997:1-6; Nienaber C A. Pathophysiology of acute aortic syndromes. In: Baliga R R, Nienaber C A, Isselbacher E M, Eagle K A, editors., eds. *Aortic Dissection and Related Syndromes* New York, N.Y.: Springer; 2007:17-43).

SUMMARY

As described below, the present disclosure features compositions and methods for the targeted epigenetic therapy inherited aortic aneurysm and other diseases or disorders associated with altered regulation of TGFβ target genes.

In certain embodiments, a method for treating a subject having or at risk of developing a transforming growth factor β-associated disease, disorder and/or condition comprises administering to the subject an effective amount of one or more agents that modulate transforming growth factor β (TGFβ) expression by modulating the expression and/or activity of histone acetyl-transferase (HAT), thereby treating the subject.

In certain embodiments, a TGFβ associated disease is aortic aneurysm syndrome, and/or associated disorders thereof. Examples of an aortic aneurysm syndrome comprises Shprintzen-Goldberg syndrome (SGS), Marfan syndrome (MFS), Loeys-Dietz syndrome (LDS), Ehlers-Danlos syndrome (EDS), familial aortic dissection, or annuloaortic ectasia.

In certain embodiments, an agent inhibits histone acetyl-transferase (HAT) expression and/or activity as compared to a normal control and/or excessive acetylation of H3K27. In some embodiments, the inhibitor is a selective inhibitor of EP300/CREB-binding protein (CBP) expression and/or activity as measured by TGFβ expression and/or activity.

In some embodiments, the method of treatment further comprises administering one or more inhibitors of TGFβ expression and/or activity.

In embodiments, the one or more TGFβ inhibitors modulate acetylation of histone H3K27 and/or normalize TGFβ synthetic repertoire (TSR) expression.

In other embodiments, a method of preventing or treating a transforming growth factor β (TGFβ) induced aortic aneurysm syndrome in a subject, comprises administering to the subject a therapeutically effective amount of a histone acetyl-transferase (HAT) inhibitor, thereby treating the subject.

In certain aspects of the invention, an agent inhibits histone acetyl-transferase (HAT) expression and/or activity as compared to a normal control.

In certain embodiments, the agent is a selective inhibitor of EP300/CREB-binding protein (CBP) expression and/or activity as measured by TGFβ expression and/or activity.

In some embodiments, the method of treatment further comprises administering one or more inhibitors of TGFβ expression and/or activity. In some embodiments, the one or more TGFβ inhibitors modulate acetylation of histone H3K27 and/or normalize TGFβ synthetic repertoire (TSR) expression.

In other embodiments, a method of preventing or treating aneurysm progression and/or preservation of aortic wall architecture in a subject, comprising administering to the subject a therapeutically effective amount of a histone acetyl-transferase (HAT) inhibitor, thereby treating the subject.

In embodiments, a pharmaceutical composition comprises a therapeutically effective amount of at least one histone acetyl-transferase (HAT) inhibitor.

In certain embodiments, the pharmaceutical composition further comprises one or more one or more inhibitors of TGFβ expression and/or activity.

In some embodiments the pharmaceutical composition further comprises one or more agents that modulate transforming growth factor β target gene expression.

Other aspects are described infra.

DEFINITIONS

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

As used herein, the term "agent" is meant to encompass any molecule, chemical entity, composition, drug, therapeutic agent, chemotherapeutic agent, or biological agent capable of preventing, ameliorating, or treating a disease or other medical condition. The term includes small molecule compounds, antisense oligonucleotides, siRNA reagents, antibodies, antibody fragments bearing epitope recognition sites, such as Fab, Fab', F(ab')$_2$ fragments, Fv fragments, single chain antibodies, antibody mimetics (such as DARPins, affibody molecules, affilins, affitins, anticalins, avimers, fynomers, Kunitz domain peptides and monobodies), peptides, aptamers; enzymes, peptides organic or inorganic molecules, natural or synthetic compounds and the like. An agent can be assayed in accordance with the methods of the invention at any stage during clinical trials, during pre-trial testing, or following FDA-approval.

By "ameliorate" is meant decrease, suppress, attenuate, diminish, arrest, or stabilize the development or progression of a disease.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA (Eguchi et al., 1991 Ann. Rev. Biochem. 60, 631-652). An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

As used in this specification and the appended claims, the term "or" is generally employed in its sense including "and/or" unless the content clearly dictates otherwise.

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

A "disease" is a state of health of an animal wherein the animal cannot maintain homeostasis, and wherein if the disease is not ameliorated then the animal's health continues to deteriorate. Examples of diseases include Shprintzen-Goldberg syndrome (SGS), Marfan syndrome (MFS), Loeys-Dietz syndrome (LDS), Ehlers-Danlos syndrome (EDS), familial aortic dissection, or annuloaortic ectasia.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type target gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

"Parenteral" administration of an immunogenic composition includes, e.g., subcutaneous (s.c.), intravenous (i.v.), intramuscular (i.m.), or intrasternal injection, or infusion techniques.

The terms "patient" or "individual" or "subject" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters, and primates.

The terms "pharmaceutically acceptable" (or "pharmacologically acceptable") refer to molecular entities and compositions that do not produce an adverse, allergic or other untoward reaction when administered to an animal or a human, as appropriate. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance.

By "reference" is meant a standard or control condition.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "TGFβ-associated disease, disorder and/or condition" is meant any disease, disorder and/or condition that has been identified or may be identified as associated with altered expression and/or activity of TGFβ. Exemplary TGFβ-associated diseases, disorders and/or conditions of the instant disclosure include Shprintzen-Goldberg syndrome (SGS), Marfan syndrome (MFS), Loeys-Dietz syndrome (LDS), Ehlers-Danlos syndrome (EDS), familial aortic dissection, or annuloaortic ectasia and those associated with upregulation of TGFβ (optionally induced by distal enhancer sequence(s) of TGFβ), such as Scleroderma, other fibrotic disease, grade 4 glioblastoma (GBM) and/or Primary Open-Angle Glaucoma (POAG).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, which in some embodiments relate to mammalian nucleic acid and amino acid sequences, are intended to encompass homologous and/or orthologous genes and gene products from other animals including, but not limited to other mammals, fish, amphibians, reptiles, and birds. In preferred embodiments, the genes, nucleic acid sequences, amino acid sequences, peptides, polypeptides and proteins are human. The term "gene" is also intended to include variants.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

BRIEF DESCRIPTION OF THE DRAWINGS

FIG. 2A is a graph showing the expression level of complement of Ski mRNA (+/−SEM) in each mouse line. Both Ski +/− and Ski G34D/+:Neo haploinsufficient mouse lines express half the normal complement of Ski mRNA while Ski G34D/+ mouse line expresses in full the normal complement of Ski mRNA which includes the mutant allele expression. *P<0.05; P<0.01; *P<0.001; NS, not significant. FIG. 2B shows amplified Ski cDNA of each mouse line. The Ski G34D/+mouse line uniquely expresses the mutant allele as shown by the BamH1 restriction fragment of amplified cDNA.

(17.00+/−2.31), VSMC/Ski G34D/+ (14+/−1.155). *P<0.05; P<0.01; *P<0.001; +P<10⁻⁴; ++P<10⁻⁶; NS, not significant.

Figure 1:
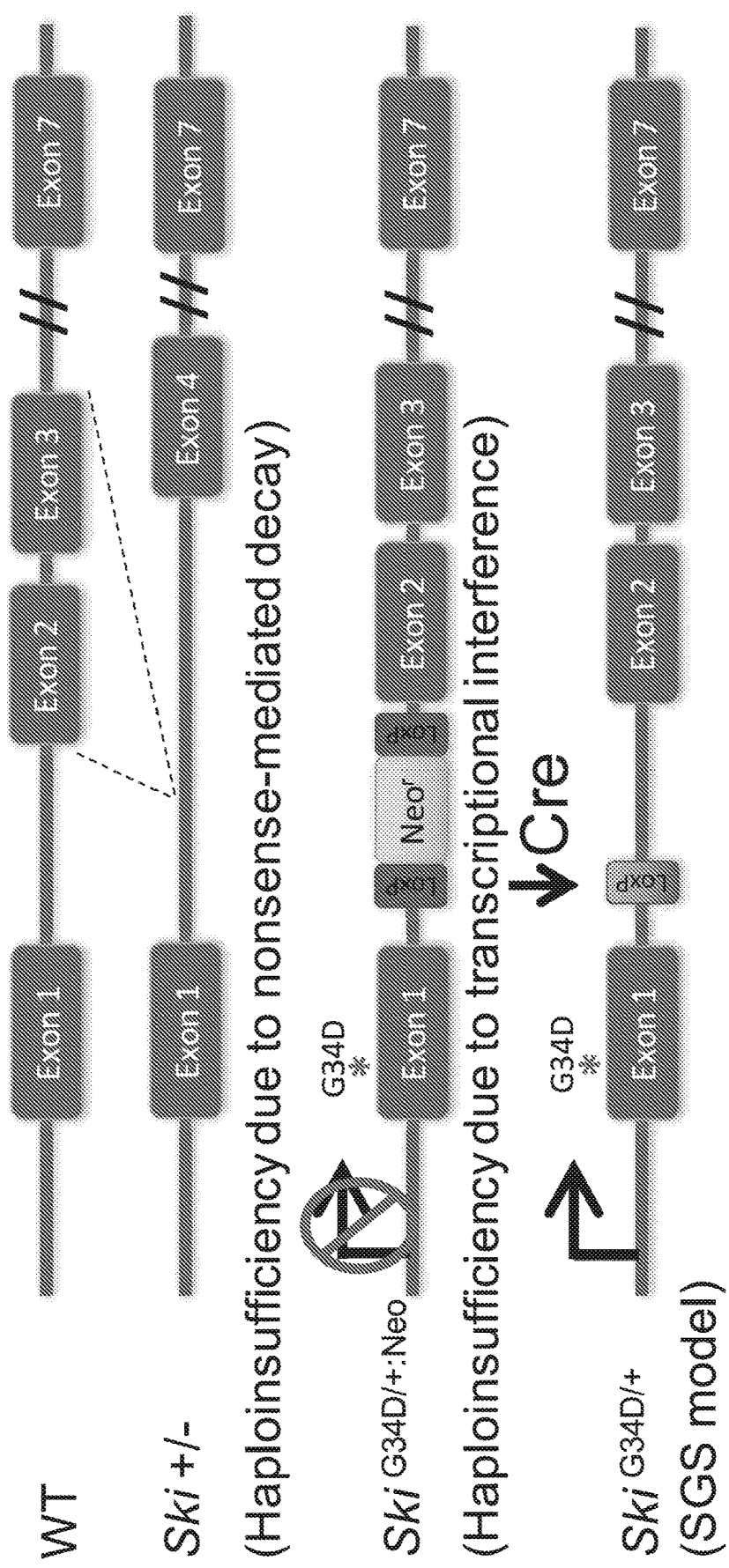
FIG. 1 is a schematic overview of multiple SKI mouse lines. Ski haploinsufficient mouse, called Ski +/−, is heterozygous for deletion of exons 2 and 3 of the Ski gene. This leads to functional haploinsufficiency due to nonsense mediated decay. Ski G34D/+:Neo mouse is heterozygous for a missense mutation previously observed in a severe SGS patient. The allele retains a floxed neomycin resistance cassette which causes transcriptional interference and functional haploinsufficiency. Upon exposure to Cre recombinase, this allele loses the Neo cassette, allowing for transcription of the mutant allele and expression of mutant SKI. Mice heterozygous for this allele, called Ski G34D/+, recapitulate the molecular mechanism of human Shprintzen-Goldberg syndrome.
Figure 2A:
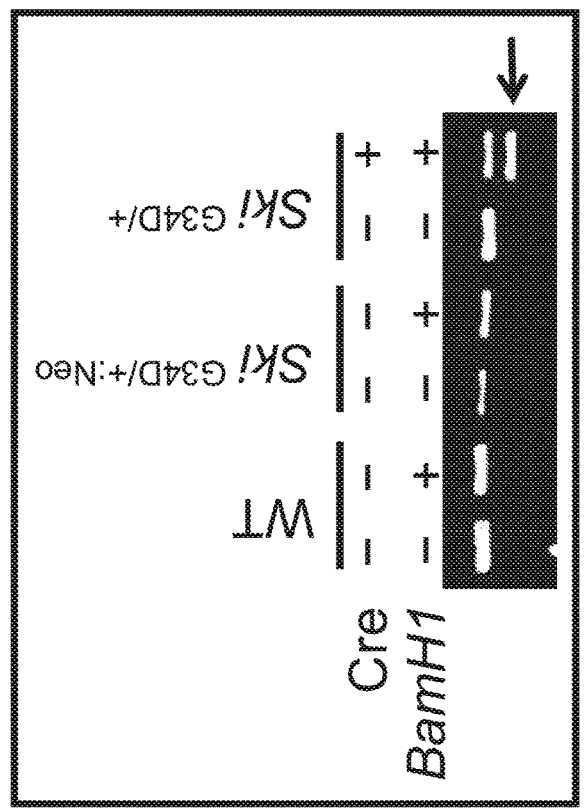
FIGS. 2A & 2B show the expression level of Ski in each mouse line.
Figure 2B:
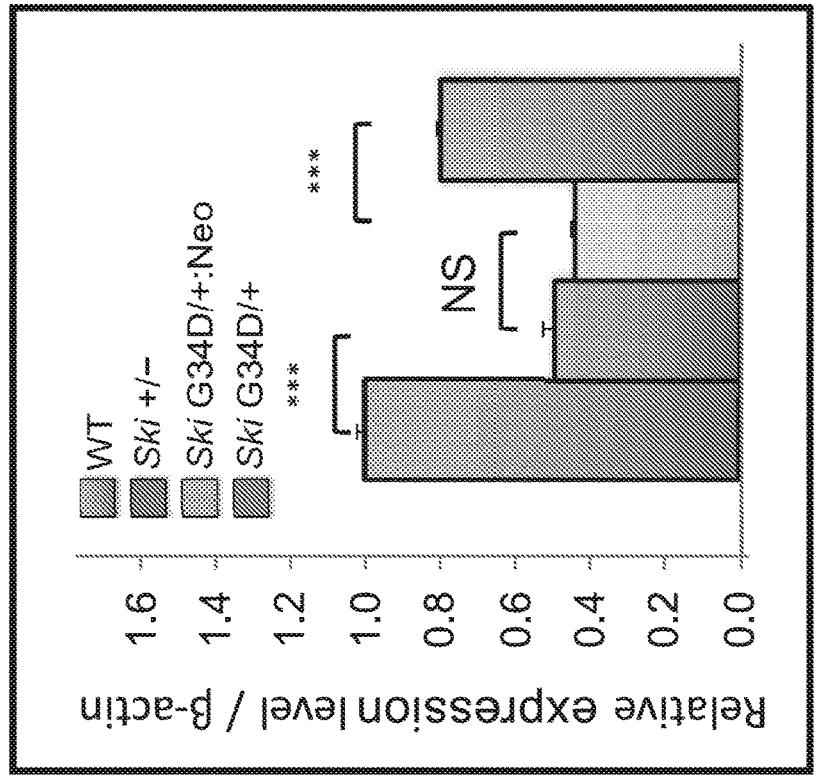
Figure 3:
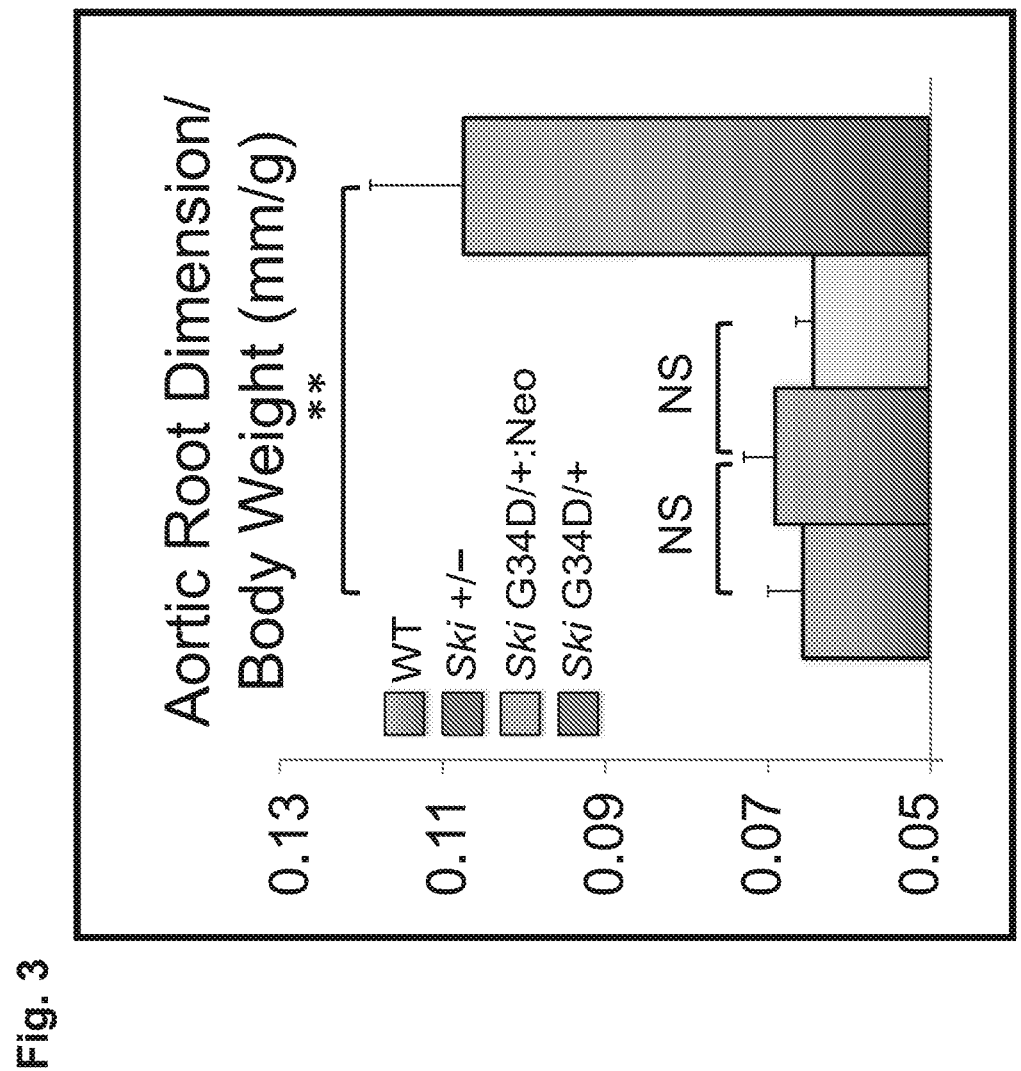
FIG. 3 is a graph showing the average absolute aortic root diameter normalized by body weight (+/−SEM) measured by echocardiogram at 6 months old for each mouse line. Note that the Ski G34D/+ mice have a significantly larger aortic root diameter than any other mice. Final absolute aortic root diameter normalized by body weight: WT (0.066+/−0.004 mm/g), Ski +/− (0.069+/−0.004 mm/g), Ski G34D/+:Neo (0.064+/−0.002 mm/g) and Ski G34D/+ (0.107+/−0.012 mm/g). WT (n=9), Ski +/− (n=10), Ski G34D/+:Neo (N=10), Ski G34D/+ (n=11). *P<0.05; **P<0.01; NS, not significant.
Figure 4:
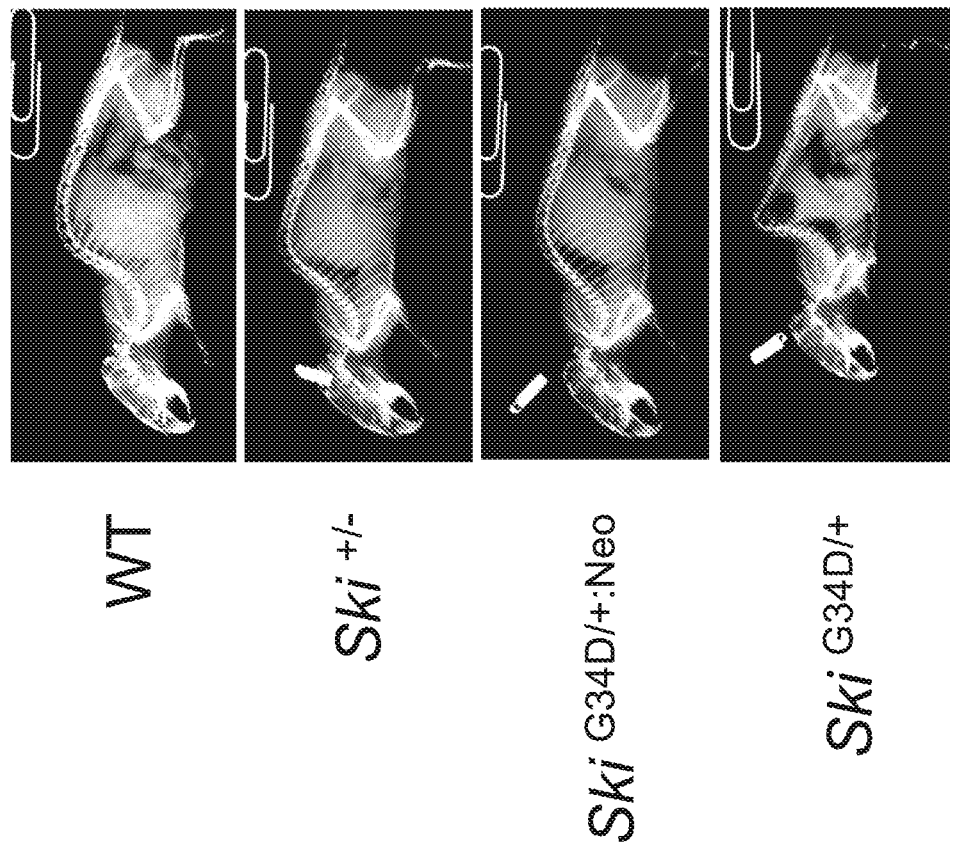
FIG. 4 is a panel of representative radiographs at 6 months old for each mouse line. Compared with other mouse lines, only the Ski G34D/+ mice demonstrated the skeletal deformity phenotype.
Figure 5:
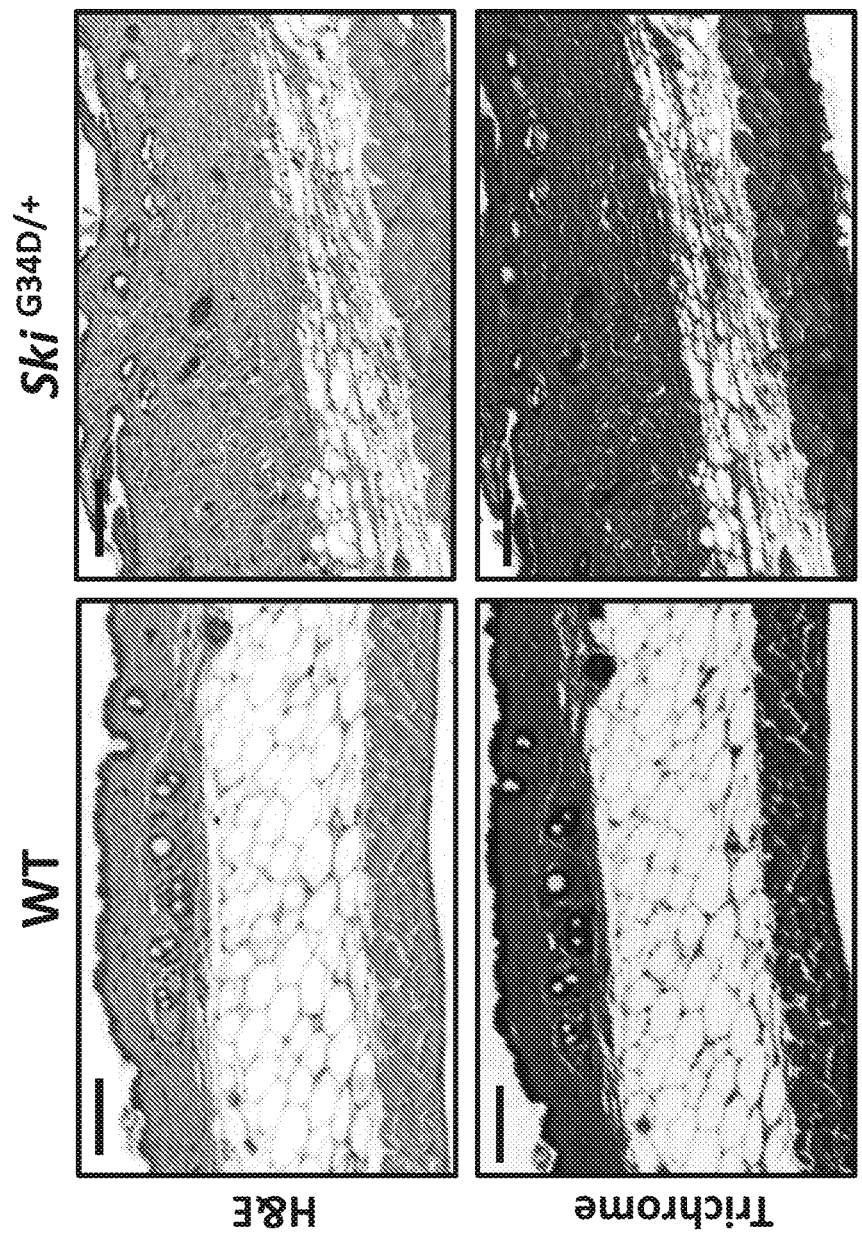
FIG. 5 is a panel of photomicrographs of VVG staining and Masson-trichrome staining of representative dorsal dermal sections of Ski G34D/+ mice and WT littermates. Compared with WT littermates, Ski G34D/+ mice demonstrated the reduced subcutaneous fat layer.
Figure 6:
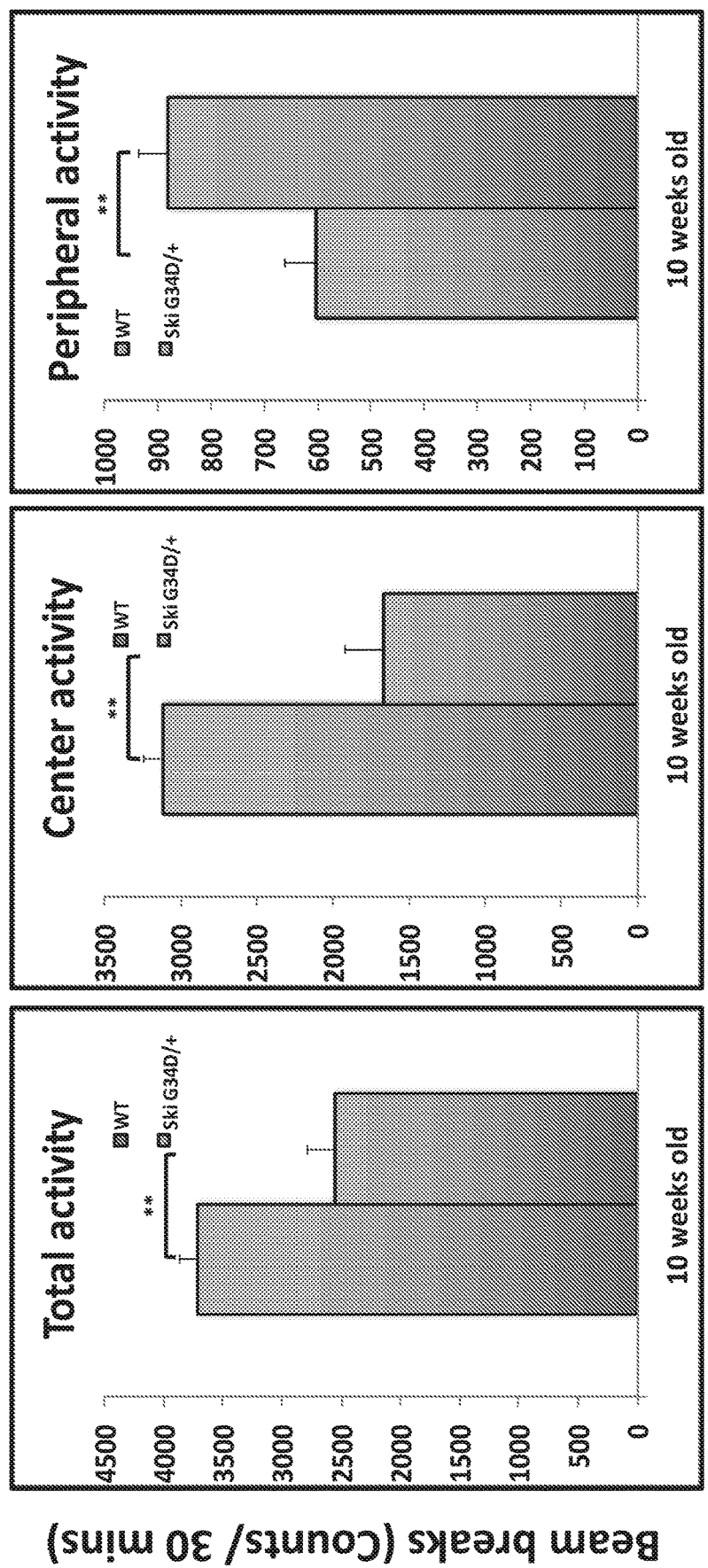
FIG. 6 are graphs showing the open field test results of WT littermates and Ski G34D/+ mice at 10 weeks old. Compared with WT littermates, Ski G34D/+ mice exhibited behavioral hypoactivity. The data are shown as beam break counts per 30 minutes (+/−SEM). For total activity, WT (3715.6+/−144.5 Counts/30 mins), Ski G34D/+ (2554.0+/−233.1 Counts/30 mins). For center activity, WT (3113.2+/−130.2 Counts/30 mins), Ski G34D/+ (1672.0+/−252.8 Counts/30 mins). For peripheral activity, WT (602.4+/−58.0 Counts/30 mins), Ski G34D/+ (882.0+/−55.2 Counts/30 mins). WT (n=5) and Ski G34D/+ (n=5). *P<0.05; **P<0.01.
Figure 7:
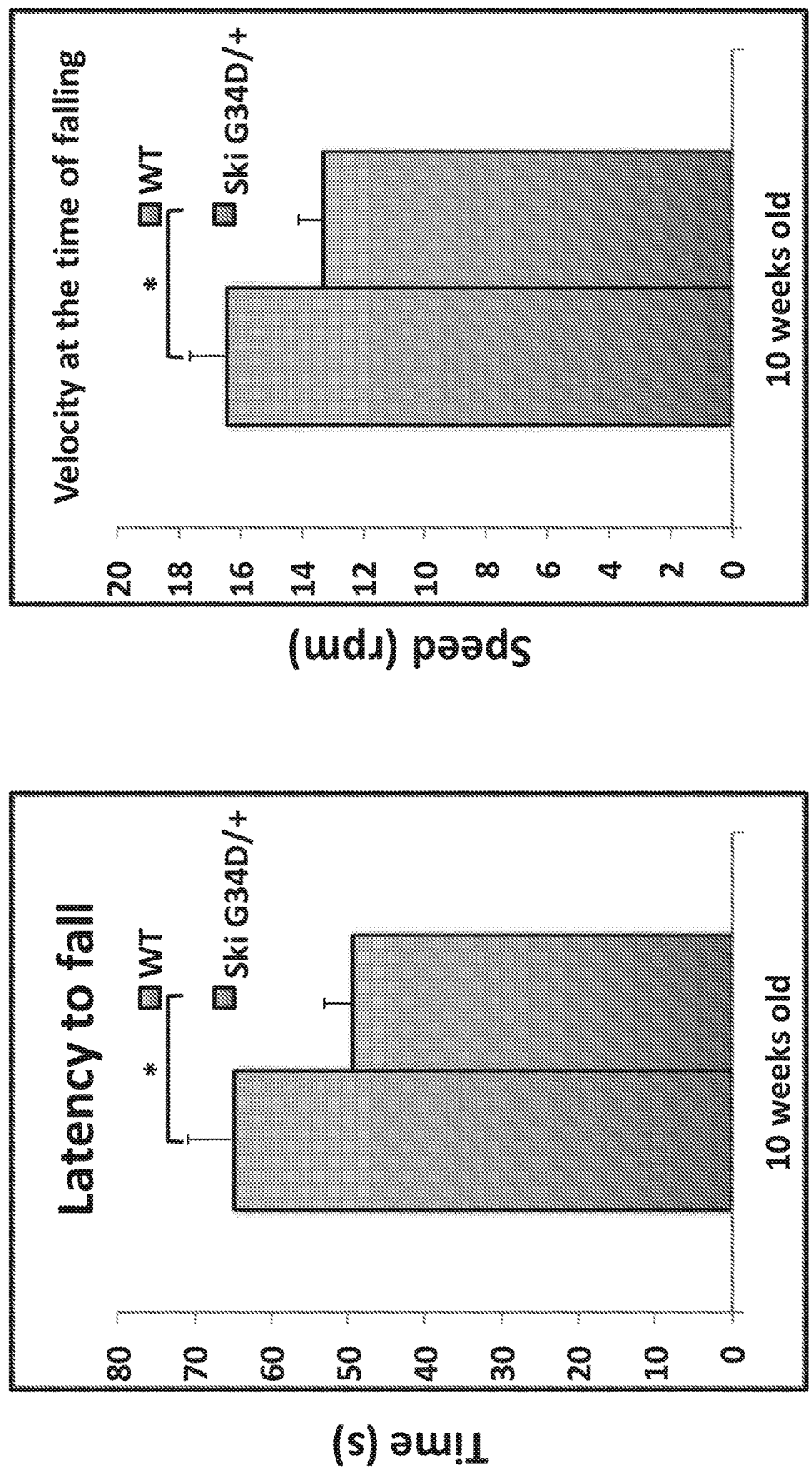
FIG. 7 are graphs showing the rotarod test results of WT littermates and Ski G34D/+ mice at 10 weeks old. Compared with WT littermates, Ski G34D/+ mice demonstrated impaired motor performance. The latency to fall is shown as time (seconds +/−SEM) that mice remained on an accelerating rotarod (1 rpm to 20 rpm over 100 seconds) before falling. WT (64.74+/−6.19 sec), Ski G34D/+ (49.50+/−3.71 sec). For the average rotational velocity (rpm +/−SEM) at the time of falling, WT (16.44+/−1.23 rpm), Ski G34D/+ (13.33+/−0.78 rpm). *P<0.05.
Figure 8:
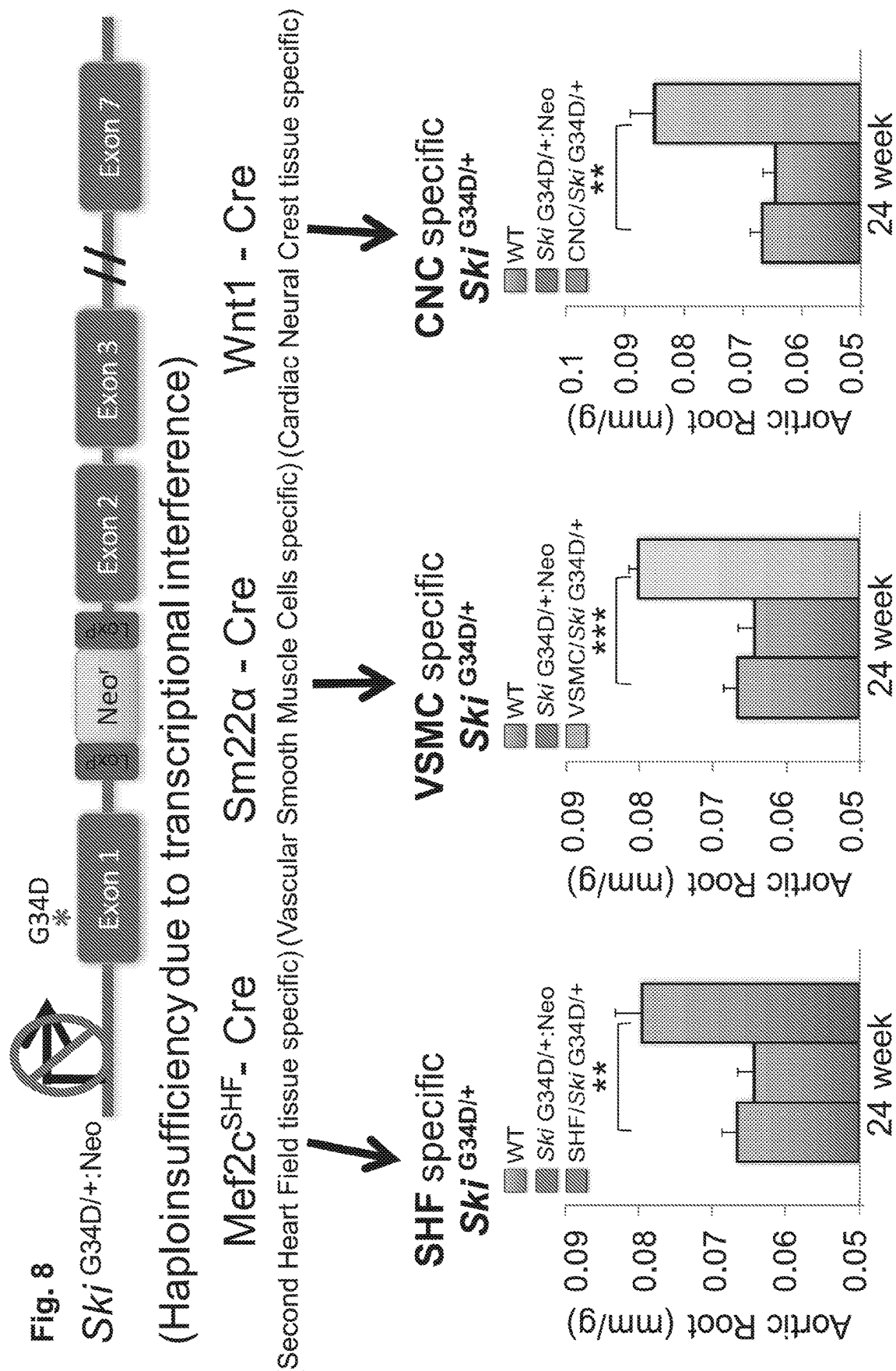
FIG. 8 contains a schematic overview of multiple tissue specific Ski G34D/+ mouse lines and graphs showing the average absolute aortic root diameter normalized by body weight (+/−SEM) as measured by echocardiogram at 6 months old for each mouse line. Mef2c$^{SHF}$-Cre is a Cre recombinase under transcriptional control of a second heart field (SHF) tissue specific promoter. SM22ais a vascular smooth muscle cells (VSMC) specific promoter. Wnt1 is a cardiac neural crest (CNC) tissue specific promoter. Note that the each Cre/Ski G34D/+ mice has a significantly larger aortic root diameter than WT littermates and unrecombined Ski G34D/+:Neo mice. Final absolute aortic root diameter normalized by body weight: WT (0.067+/−0.002 mm/g), Ski G34D/+:Neo (0.064+/−0.002 mm/g), SHF/Ski G34D/+ (0.079 +/−0.004 mm/g), VSMC/Ski G34D/+ (0.080+/−0.001 mm/g), CNC/Ski G34D/+ (0.085+/−0.004 mm/g). WT (n=10), Ski G34D/+:Neo (n=11), SHF/Ski G34D/+ (n=6), VSMC/Ski G34D/+ (n=10), CNC/Ski G34D/+ (n=5). *P<0.05; P<0.01; *P<0.001.
Figure 9:
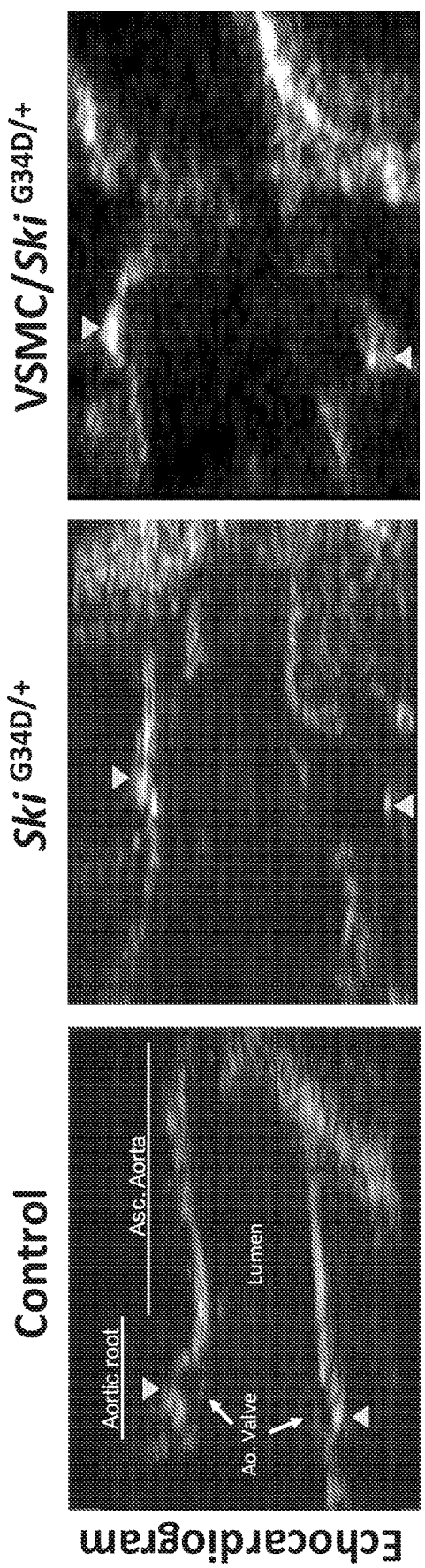
FIG. 9 is a panel of representative photomicrographs of echocardiograms for each mouse line. Compared to WT littermates, Ski G34D/+ mice demonstrated a significantly larger aortic root diameter.
Figure 10:
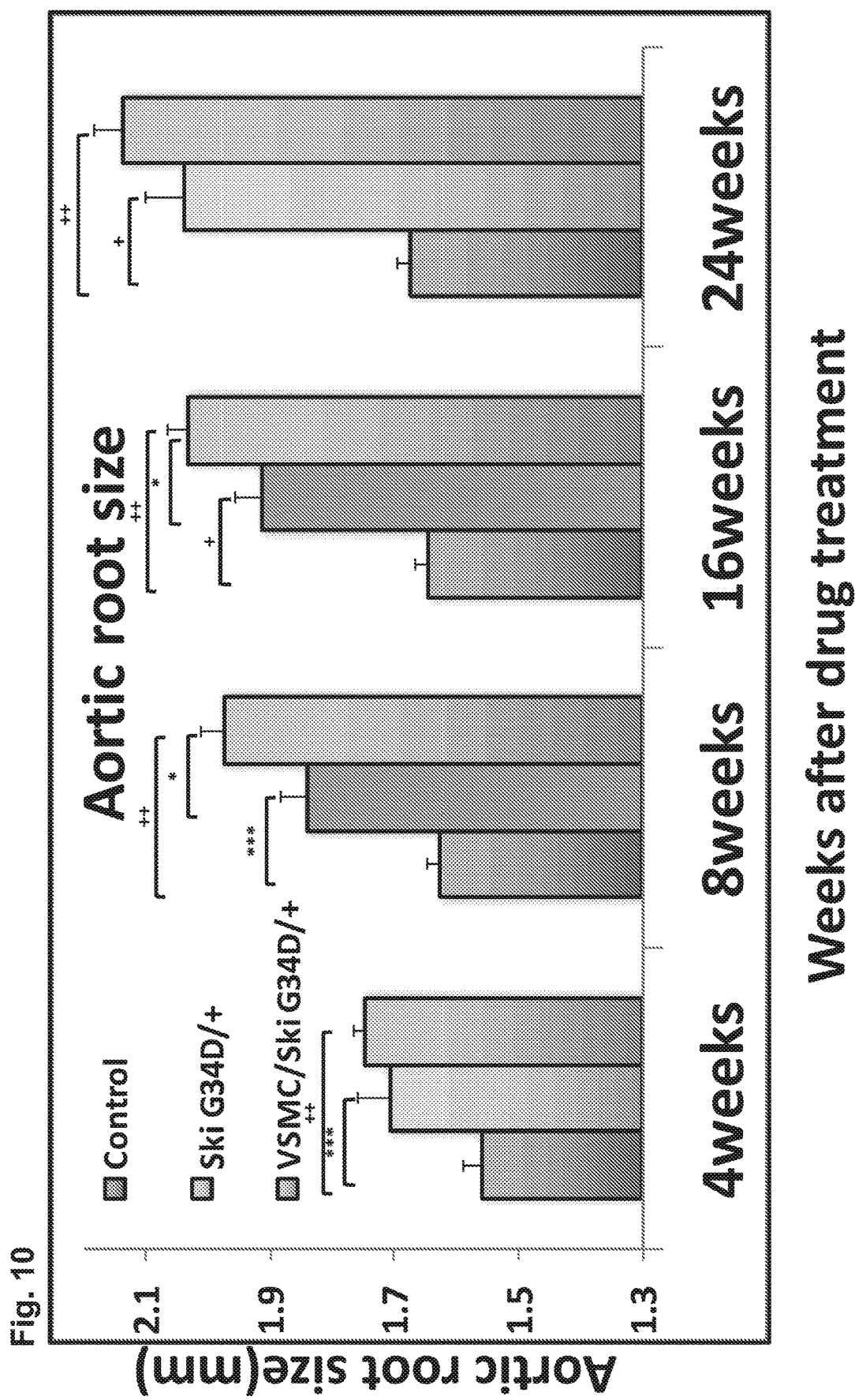
FIG. 10 is a graph showing the average absolute aortic root diameter (+/−SEM) measured by echocardiogram for each mouse line. Three independent measurements of the aortic root were made from the long axis echo view in systole at each time point (8 weeks old, 12 weeks old, 16 weeks old, 24 weeks old). All analyses were performed blinded to genotype. Note that the Ski G34D/+ mice and VSMC/Ski G34D/+ mice have a significantly larger aortic root diameter than WT littermates. Final absolute aortic root diameter: WT (1.674+/0.021 mm), Ski G34D/+ (2.039+/−0.062 mm), VSMC/Ski G34D/+ (2.138+/−0.044 mm). WT(n=11), Ski G34D/+ (n=10), VSMC/Ski G34D/+ (n=12). *P<0.05; P<0.01; *P<0.001; +P<10$^{-4}$; ++P<10$^{-6}$; NS, not significant.
Figure 11:
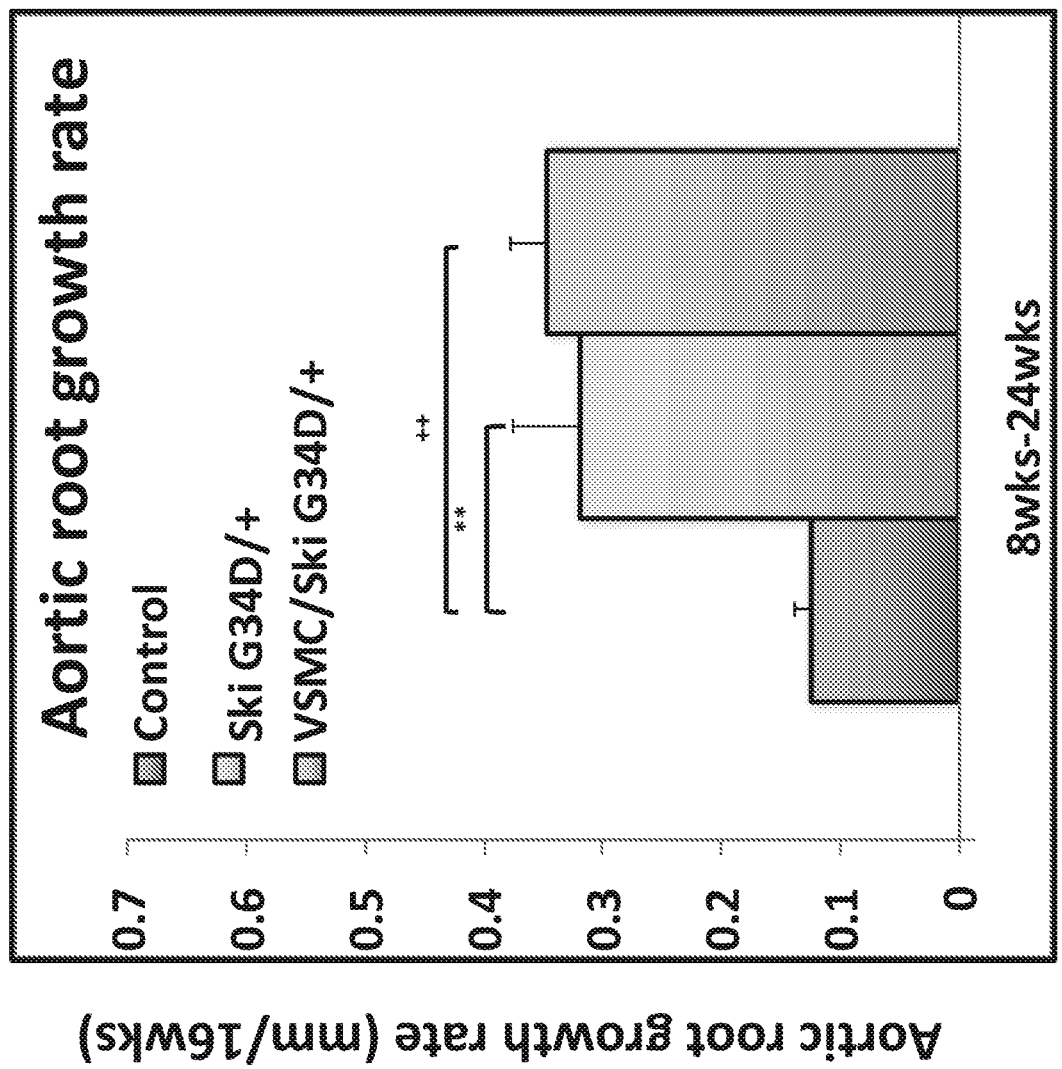
FIG. 11 is a graph showing average aortic root growth (+/−SEM) over 16 weeks as measured by echocardiogram. Note that the rate of aortic root growth of the Ski G34D/+ mice and VSMC/Ski G34D/+ mice is faster than that of WT littermates. Final aortic root growth rate: WT (0.125+/−0.012 mm/16 weeks), Ski G34D/+ (0.318+/−0.057 mm/16 weeks), VSMC/Ski G34D/+ (0.347+/−0.032 mm/16 weeks). WT(n=11), Ski G34D/+ (n=10), VSMC/Ski G34D/+ (n=12). *P<0.05; P<0.01; *P<0.001; +P<10$^{-4}$; ++P<10$^{-6}$; NS, not significant.
Figure 12:
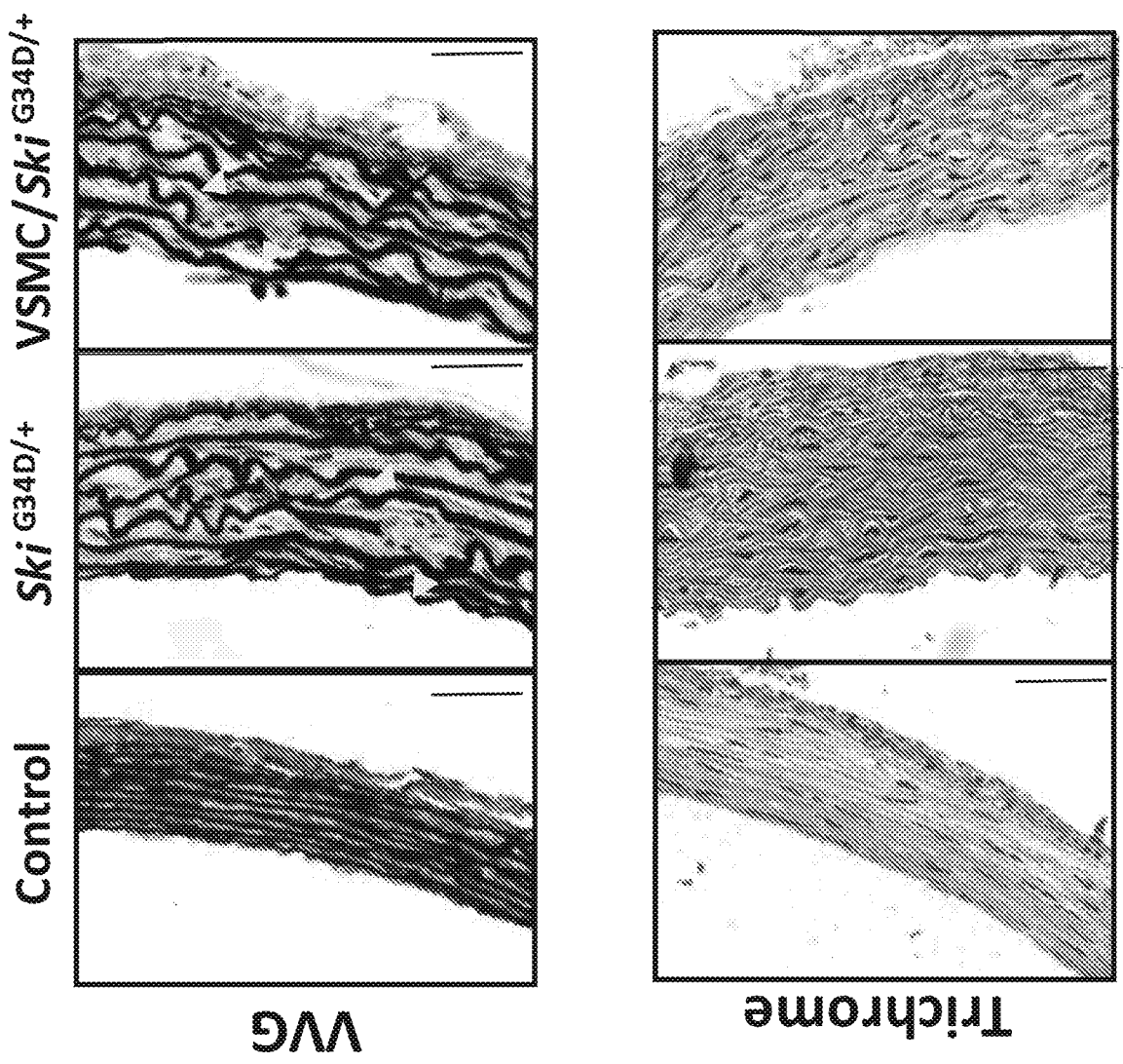
FIG. 12 is a panel of photomicrographs of VVG staining and Masson-trichrome staining of representative sections of aortic root. Compared to WT littermates, Ski G34D/+ mice and VSMC/Ski G34D/+ mice demonstrated medial thickening, elastic fiber fragmentation and increased collagen deposition.
Figure 13:
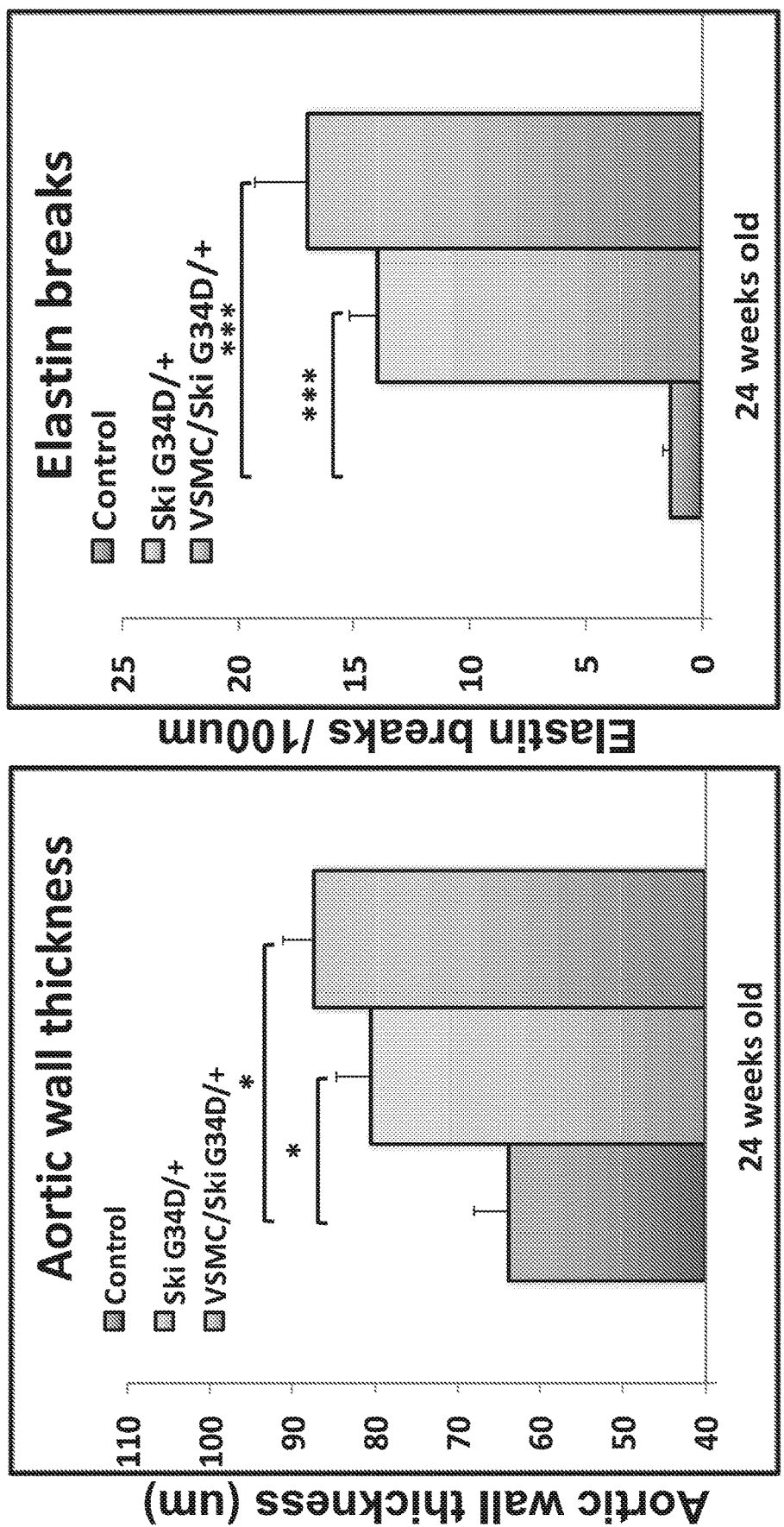
FIG. 13 are graphs showing average aortic wall thickness and average number of disruptions of the elastin fiber architecture from VVG staining of aortic root sections. Average aortic wall thickness (+/−SEM) was determined by four measurements of each of the four representative sections from each of the three mice of each genotype. The average number of disruptions of elastin fiber architecture (+/−SEM) was measured by counting fiber breaks in four sections of aorta from three mice of each genotype. The sections were processed as 5 μm of thickness and obtained every 25 μm from aortic annulus. All analyses were performed blinded to genotype. Note that compared to WT littermates, Ski G34D/+ mice and VSMC/Ski G34D/+ mice demonstrated medial thickening and elastic fiber fragmentation. Final absolute aortic wall thickness: WT (63.753+/−4.262 μm), Ski G34D/+ (80.520+/−4.169 μm), VSMC/Ski G34D/+ (87.423+/−3.791 μm). Final number of disruptions of elastin fiber architecture: WT (1.33+/−0.33), Ski G34D/+
Figure 14:
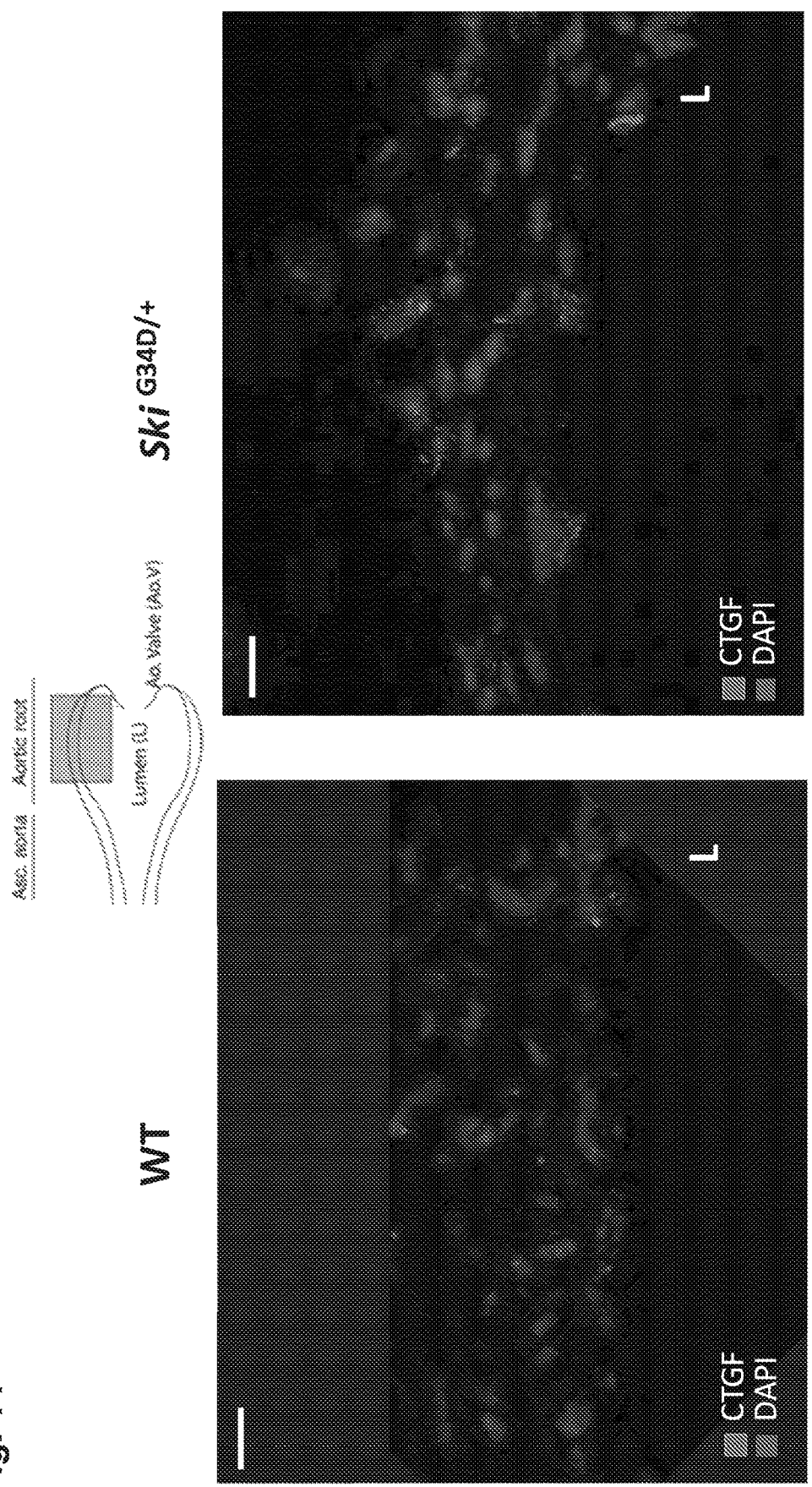

FIG. 14 is a panel of photomicrographs of CTGF mRNA (red) expression by in situ hybridization in aortic root sections. Nuclei are stained with DAPI (blue). Note that compared with WT littermates, Ski G34D/+ mice show higher expression levels of CTGF, one of the TGF target gene.

Figure 15:
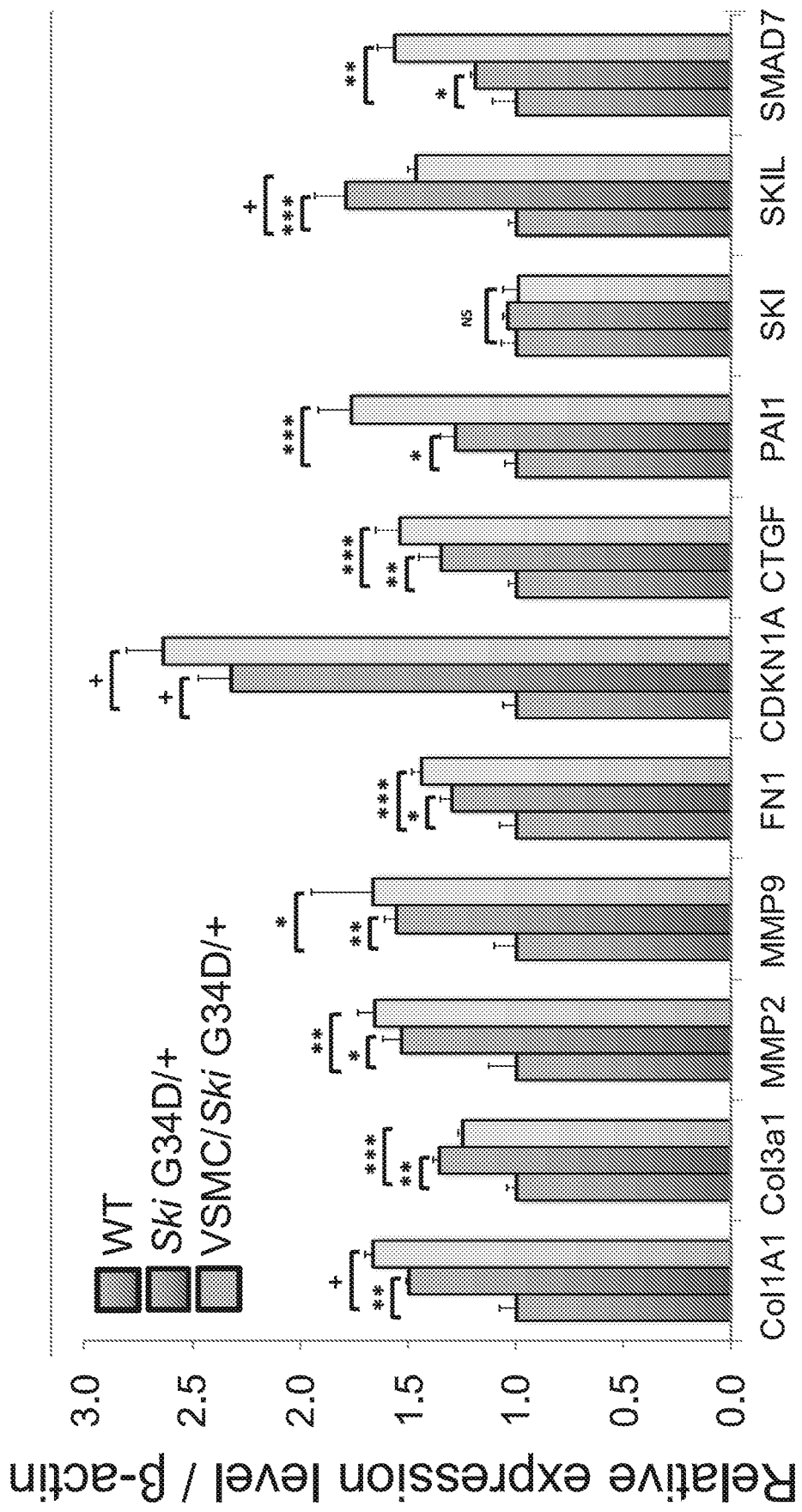

FIG. 15 is a graph showing the expression levels of TGFβ target genes relative to that of β-actin normalized by WT expression levels (+/−SEM) determined by qPCR. Compared with WT littermates, Ski G34D/+ mice and VSMC/Ski G34D/+ mice demonstrated the increased expression level of TGFβ target genes. *P<0.05; P<0.01; *P<0.001; +P<10$^{-4}$; ++P<10$^{-6}$.

Figure 16:
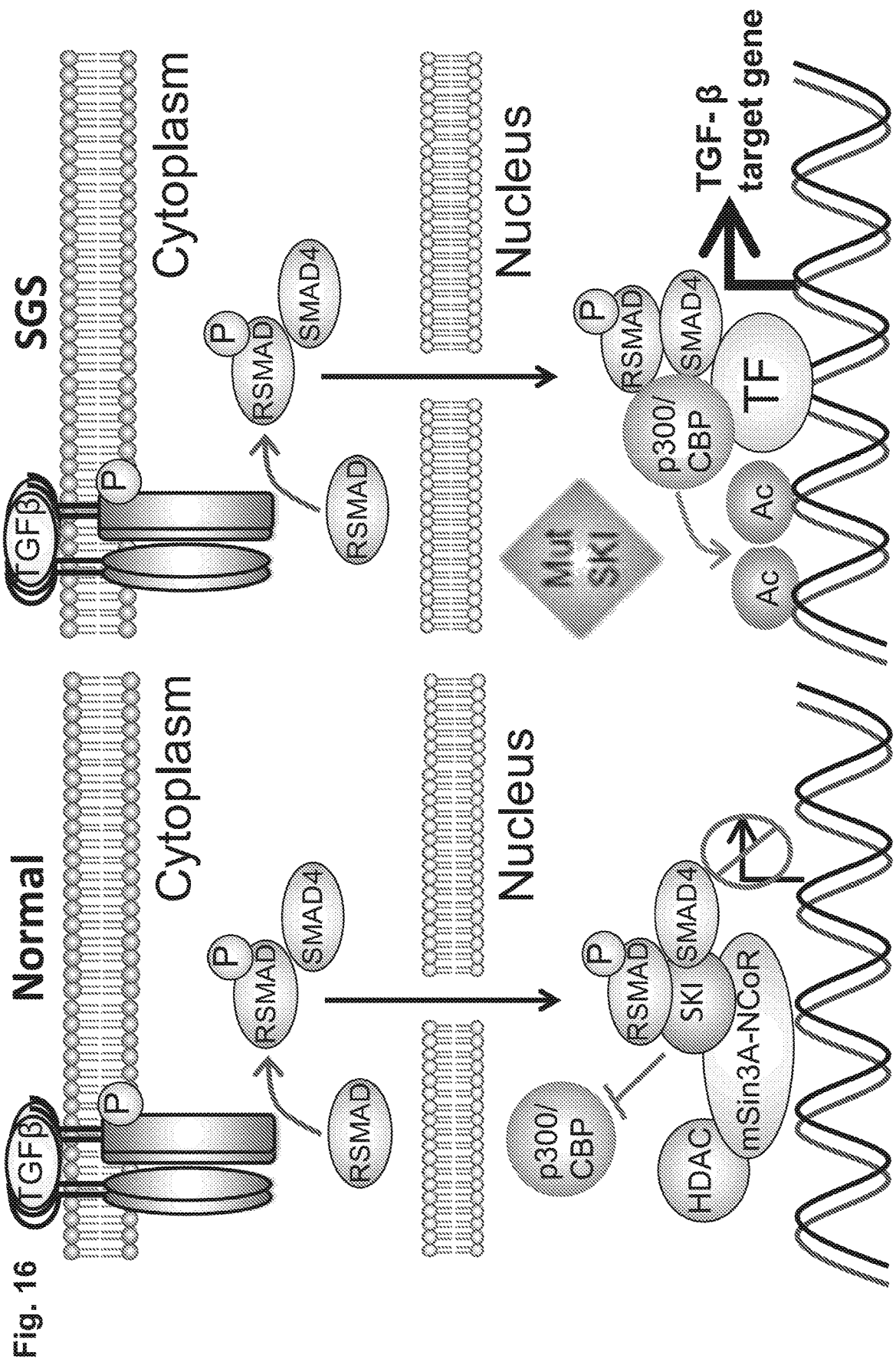

FIG. 16 is a schematic overview of WT SKI in normal cells and the mutant SKI in Shprintzen-Goldberg Syndrome (SGS) cells. When TGFβ ligand binds the TGFβ receptors, they phosphorylate R-SMAD (SMAD 2/3) which then binds Co-SMAD (SMAD 4) in the cytosol, allowing the entire SMAD complex to translocate to the nucleus. In WT cells, SKI binds to nuclear SMAD and CBP/P300 complexes and inhibits the transcription of TGFβ target genes. In SGS cells, mutant SKI cannot inhibit CBP/P300, allowing it to acetylate histone tails, and thereby activating the transcription of TGFβ target genes.

Figure 17:
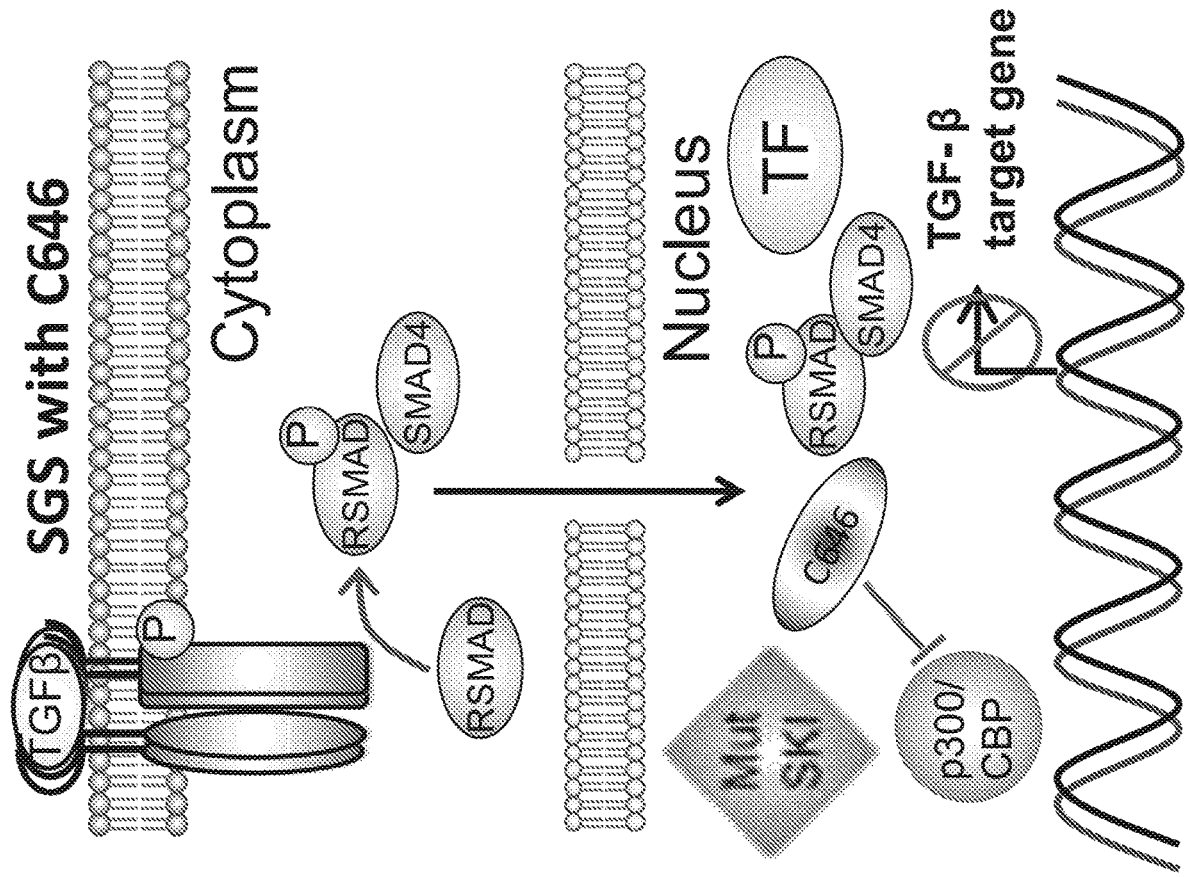

FIG. 17 is a schematic overview of how C646, a selective CBP/P300 inhibitor, works in SGS cells. By binding and inhibiting CBP/P300 HAT activity, C646 blocks TGFB target gene transcription, overcoming the defective SKI allele.

Figure 18:
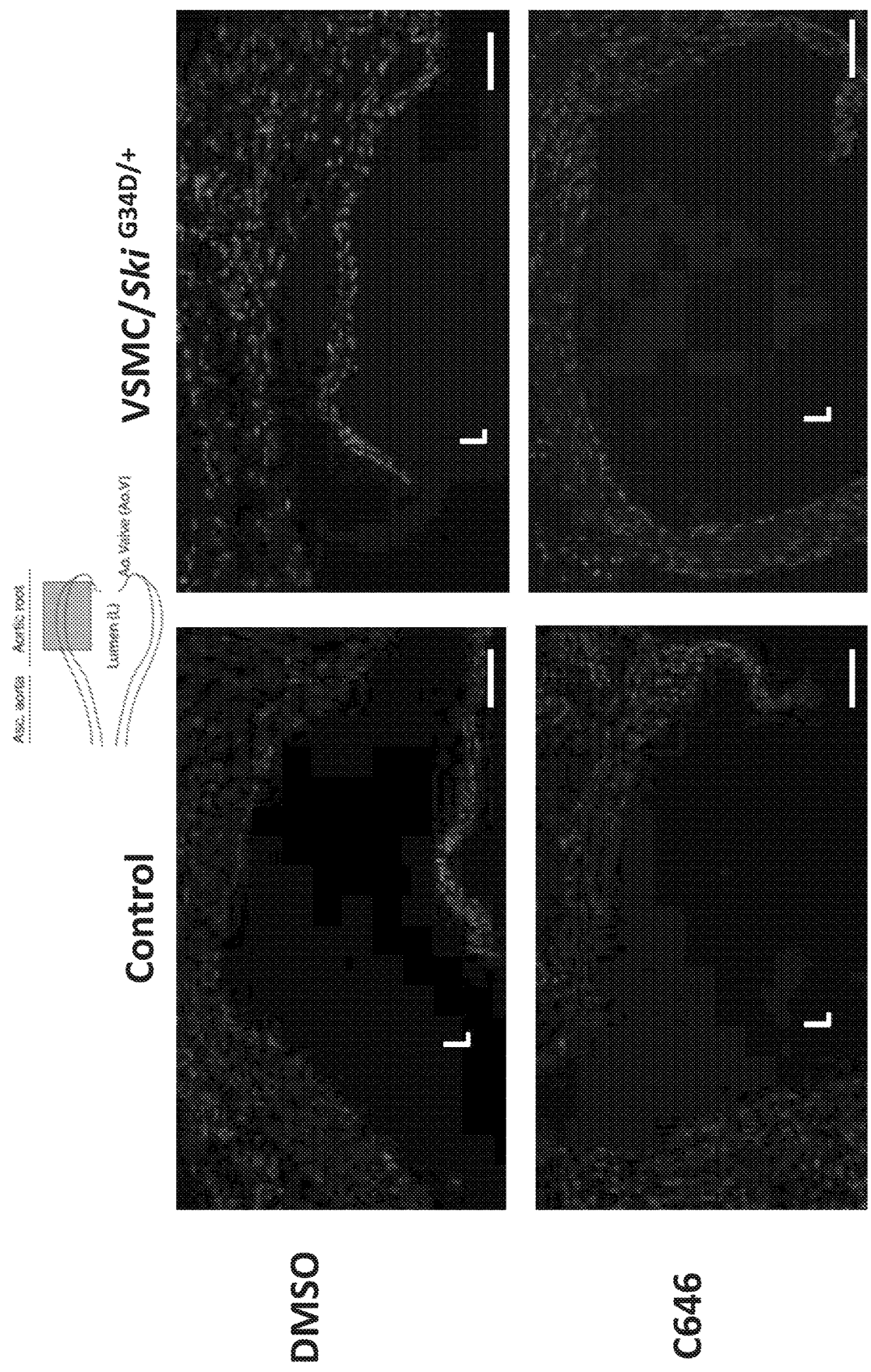

FIG. 18 is a panel of photomicrographs of immunofluorescent detection of histone 3 lysine 27 acetylation (H3K27ac) in aortic roots of control and VSMC/Ski G34D/+ mice treated with C646 or vehicle control (DMSO). For vehicle treatment, 10% DMSO in PBS was injected both in control and VSMC/Ski G34D/+ mice for placebo group. For C646 treatment, C646 dissolved in 10% DMSO was injected both of control and VSMC/Ski G34D/+ mice with 5mg/kg/day dose for the treatment group. The mice began treatment at 8 weeks of age. Compared to WT littermates, VSMC/Ski G34D/+ mice demonstrated increased acetylation of H3K27. Also, compared with DMSO-treated VSMC/Ski G34D/+ mice, C646-treated VSMC/Ski G34D/+ mice demonstrated decreased H3K27 acetylation.

Figure 19:
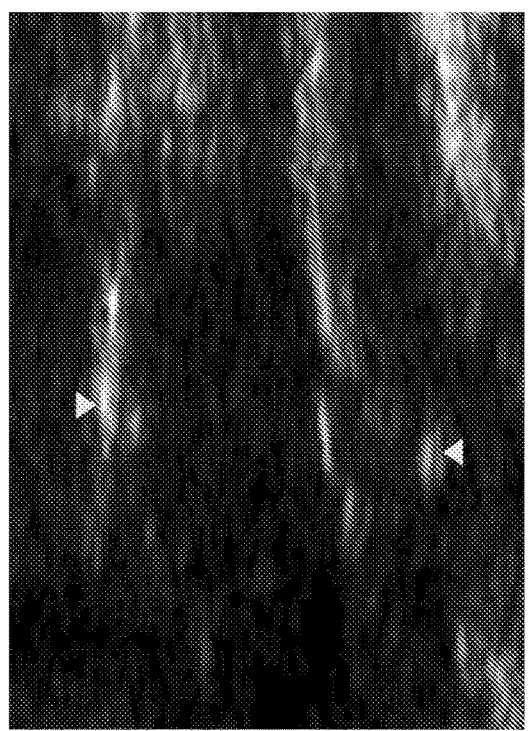
Figure 19:
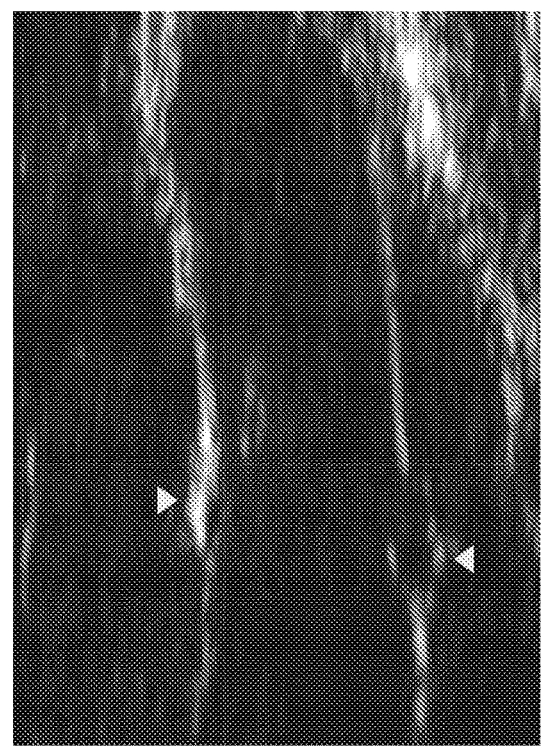
Figure 19:
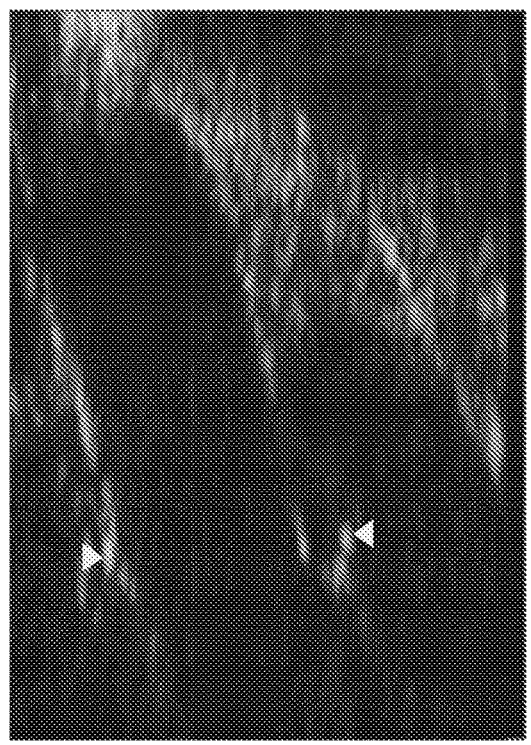
Figure 19:
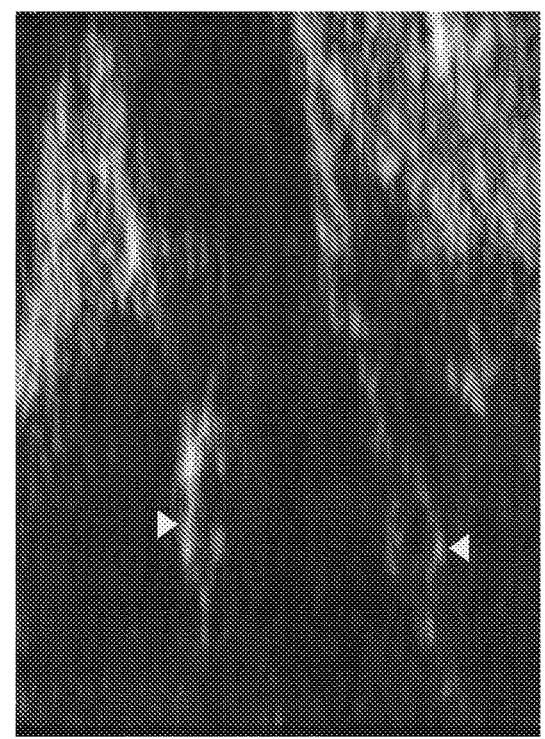

FIG. 19 is a panel of representative photomicrographs of echocardiograms for control and VSMC/Ski G34D/+ mice treated with either vehicle or C646. Compared to control littermates, VSMC/Ski G34D/+ mice demonstrated a significantly larger aortic root diameter. Also, compared with DMSO treated VSMC/Ski G34D/+ mice, C646 treated VSMC/Ski G34D/+ mice demonstrated normalized aortic root diameter.

Figure 20:
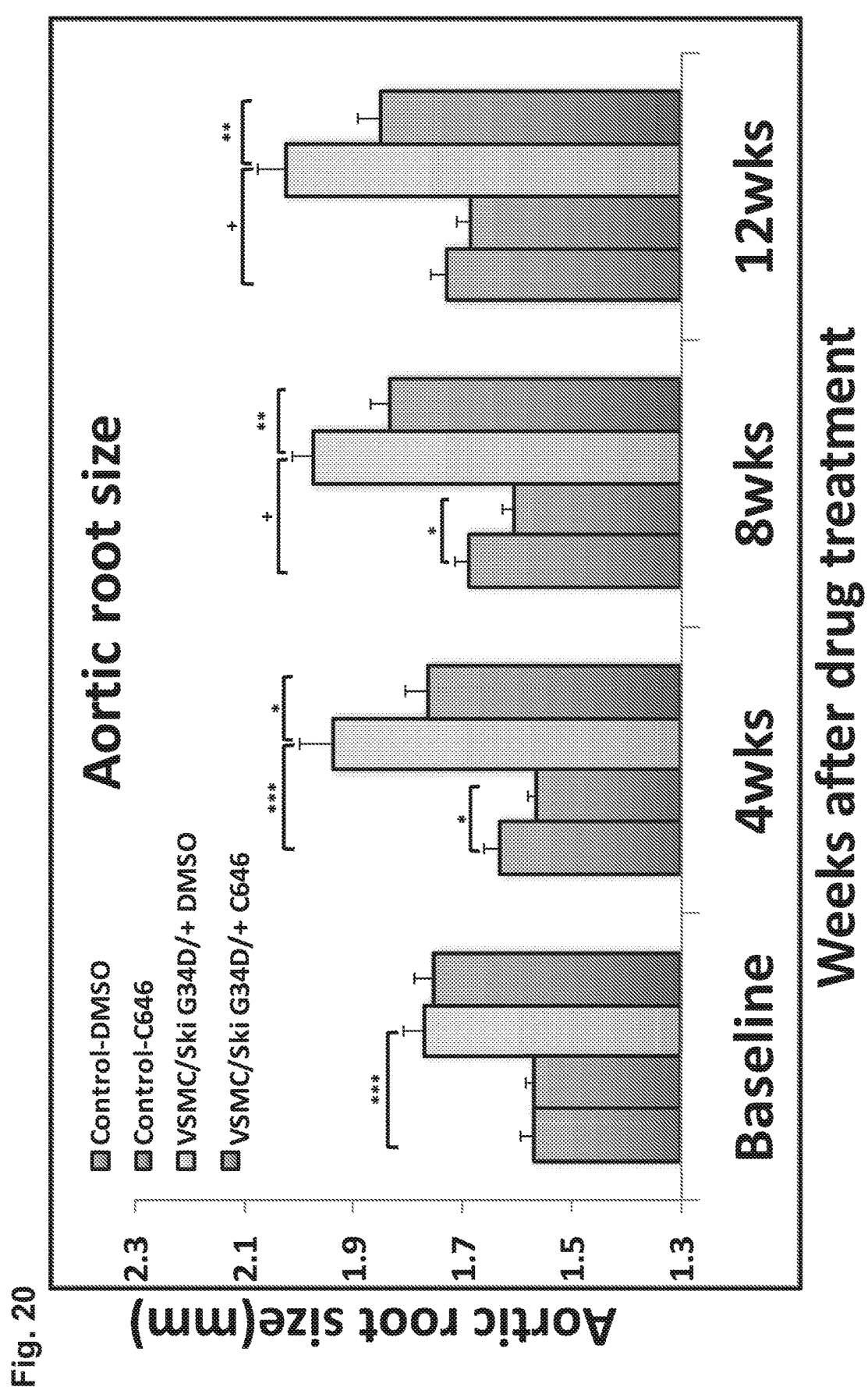

FIG. 20 shows the therapeutic effects of C646 in aortic aneurysm of VSMC/Ski G34D/+ mice. A graph shows the average absolute aortic root diameter (+/−SEM) over 12 weeks of treatment in control and VSMC/Ski G34D/+ mice with DMSO (placebo) and C646 measured serially by echocardiogram. Compared to WT littermates, VSMC/Ski G34D/+ mice demonstrated a significantly larger aortic root diameter. Also, compared with DMSO treated VSMC/Ski G34D/+ mice, C646 treated VSMC/Ski G34D/+ mice demonstrated the rescued aortic root diameter. Final absolute aortic root diameter: Control—DMSO (1.729+/−0.030 mm), VSMC/Ski G34D/+—DMSO (2.024+/−0.051 mm), Control—C646 (1.686+/−0.024 mm), VSMC/Ski G34D/+—C646 (1.848+/−0.045 mm). Control—DMSO (n=11), VSMC/Ski G34D/+—DMSO (n=13), Control—C646 (n=14), VSMC/Ski G34D/+—C646 (n=13). *P<0.05; P<0.01; *P<0.001; +P<10$^{-4}$; ++P<10$^{-6}$.

Figure 21:
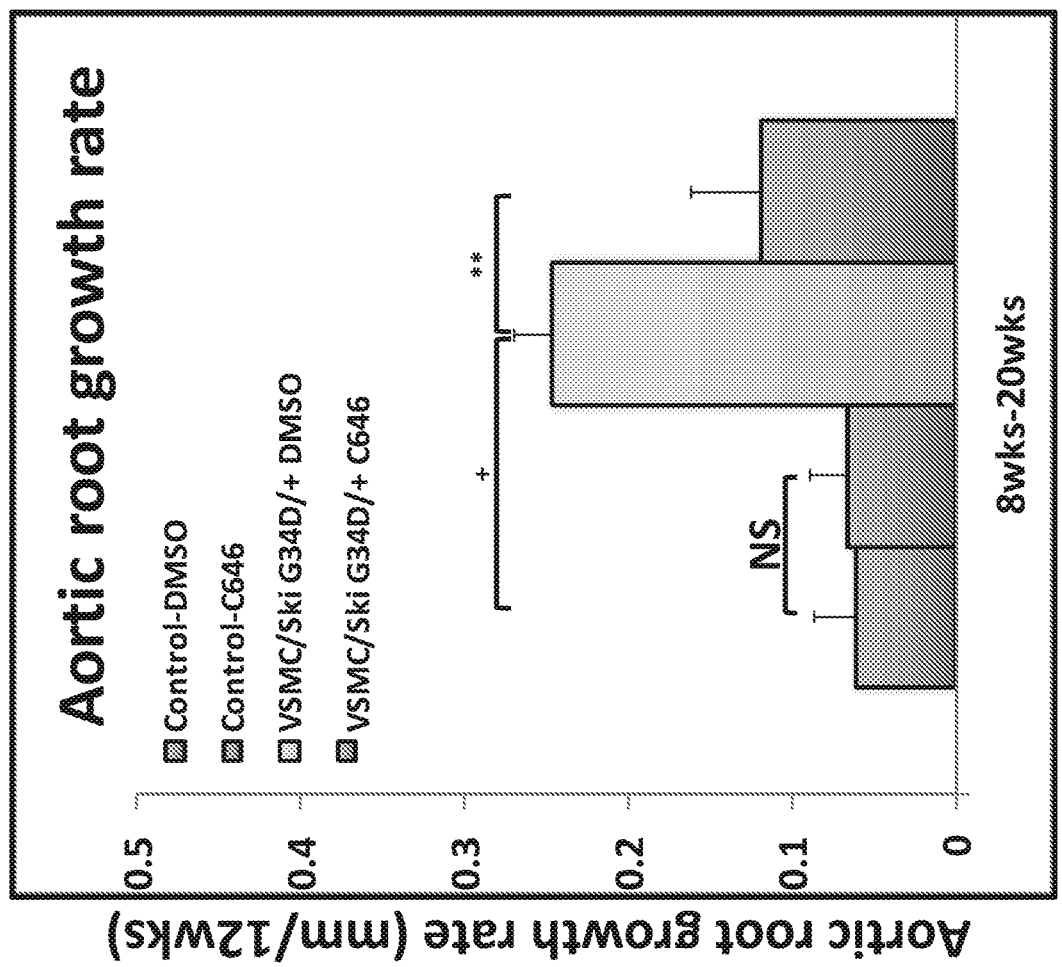

FIG. 21 is a graph showing aortic root growth (+/−SEM) over the 12 weeks of treatment in control and VSMC/Ski G34D/+ mice with DMSO (placebo) and of treated control and VSMC/Ski G34D/+ mice with C646 measured serially by echocardiogram. Compared with control littermates, VSMC/Ski G34D/+ mice demonstrated a significantly faster aortic root growth. Also, compared with DMSO treated VSMC/Ski G34D/+ mice, C646 treated VSMC/Ski G34D/+ mice demonstrated the rescued aortic root diameter. Final absolute aortic root growth rate: Control—DMSO (0.061+/−0.025 mm/12 weeks), VSMC/Ski G34D/+—DMSO (0.247+/−0.023 mm/12 weeks), Control—C646 (0.067+/−0.023 mm/12 weeks), VSMC/Ski G34D/+—C646 (0.119+/−0.042 mm/12 weeks). Control—DMSO (n=11), VSMC/Ski G34D/+—DMSO (n=13), Control—C646 (n=14), VSMC/Ski G34D/+—C646 (n=13). *P<0.05; P<0.01; *P<0.001; +P<10$^{-4}$; ++P<10$^{-6}$; NS, not significant.

Figure 22:
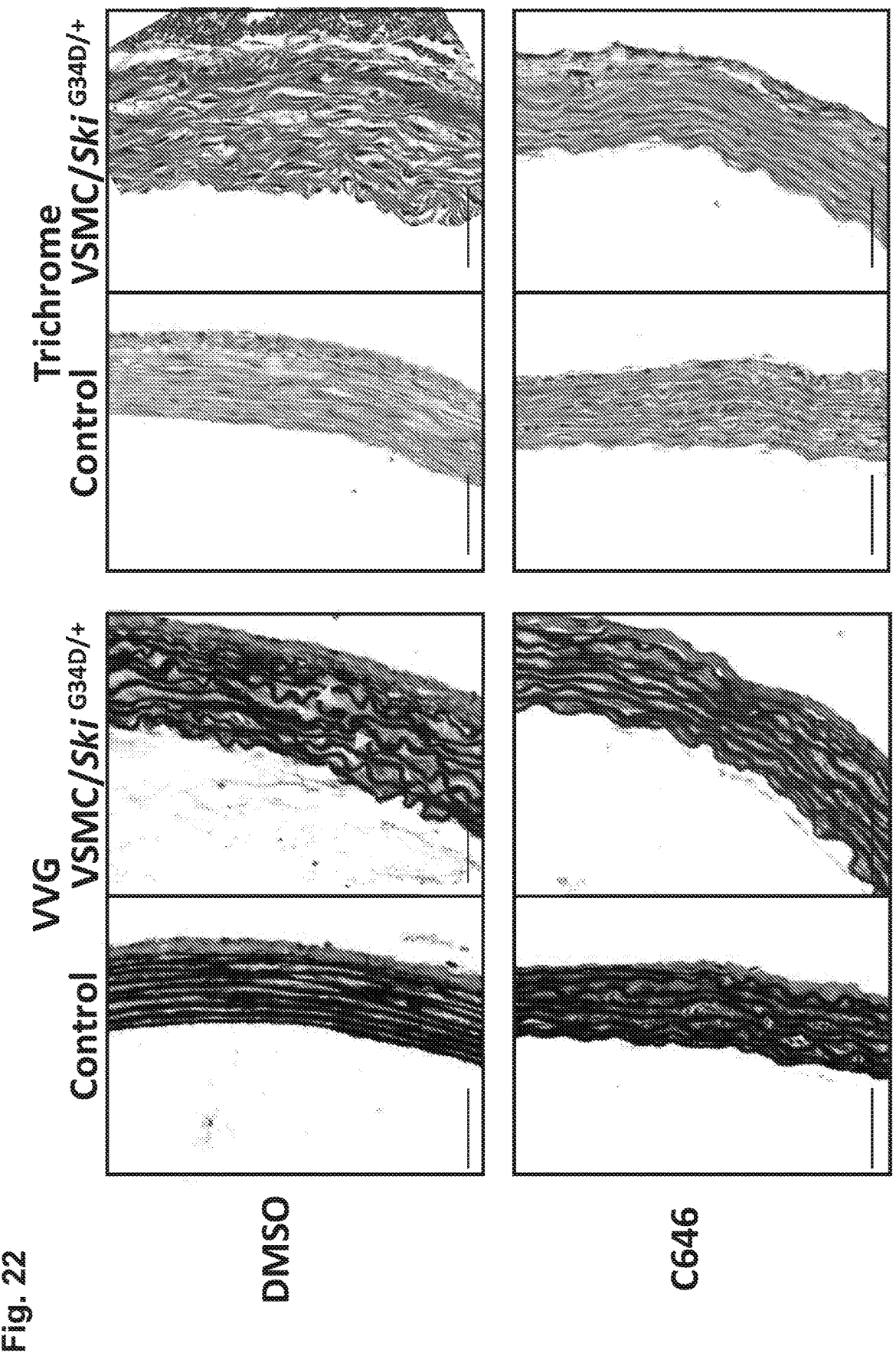

FIG. 22 is a panel of photomicrographs of VVG and Masson-trichrome staining of representative sections of aortic root. Compared with control littermates, VSMC/Ski G34D/+ mice demonstrated medial thickening, elastic fiber fragmentation and increased collagen deposition. Also, compared with DMSO treated VSMC/Ski G34D/+ mice, C646 treated VSMC/Ski G34D/+ mice demonstrated reduced medial thickening and elastic fiber fragmentation and the recovered collagen deposition.

Figure 23:
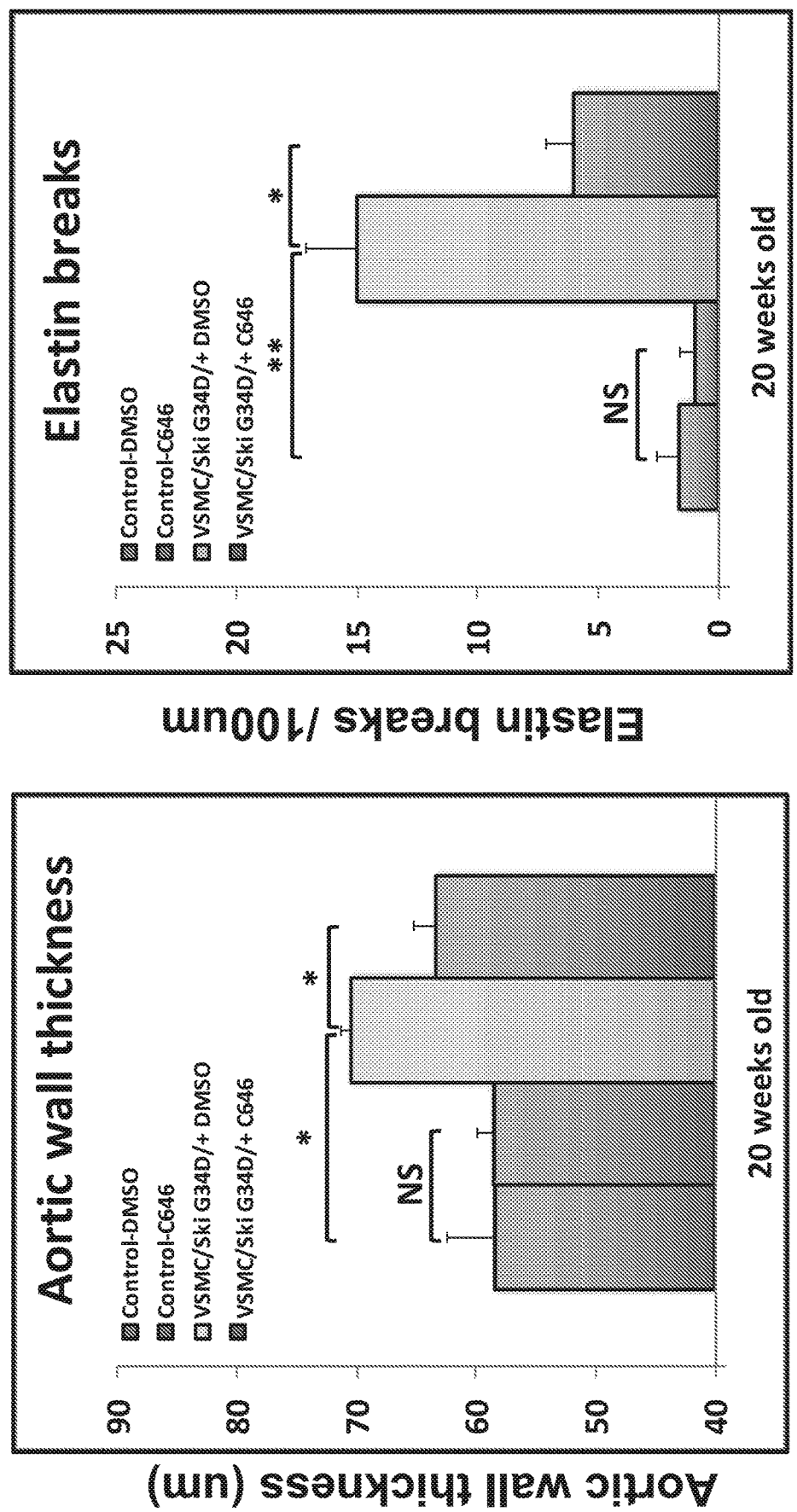

FIG. 23 are graphs showing average aortic wall thickness and average number of elastin fiber disruptions in aortic root sections. Average aortic wall thickness (+/−SEM) was determined by four measurements of each of the four representative sections from each of the three mice of each genotype. The average number of disruptions of elastin fiber architecture (+/−SEM) was measured by counting fiber breaks in four sections of aorta from three mice of each genotype. The sections were processed as 5 µm of thickness and obtained every 25 µm from aortic annulus. All analyses were performed blinded to genotype. Compared to control littermates, VSMC/Ski G34D/+ mice demonstrated medial thickening, elastic fiber fragmentation and increased collagen deposition. Also, compared with DMSO treated VSMC/Ski G34D/+ mice, C646 treated VSMC/Ski G34D/+ mice demonstrated the reduced medial thickening and elastic fiber fragmentation. Final absolute aortic wall thickness: Control—DMSO (58.309+/−4.086 µm), VSMC/Ski G34D/+—DMSO (70.491+/−0.817 µm), Control—C646 (58.547+/−1.415 µm), VSMC/Ski G34D/+—C646 (63.438+/−1.818 µm). Final number of disruptions in elastin fiber architecture: Control—DMSO (1.667+/−0.882), VSMC/Ski G34D/+—DMSO (15+/−2.082), Control—C646 (1+/−0.577), VSMC/Ski G34D/+—C646 (6+/−1.155). *P<0.05; P<0.01; *P<0.001; +P<10$^{-4}$; ++P<10$^{-6}$; NS, not significant.

Figure 24:
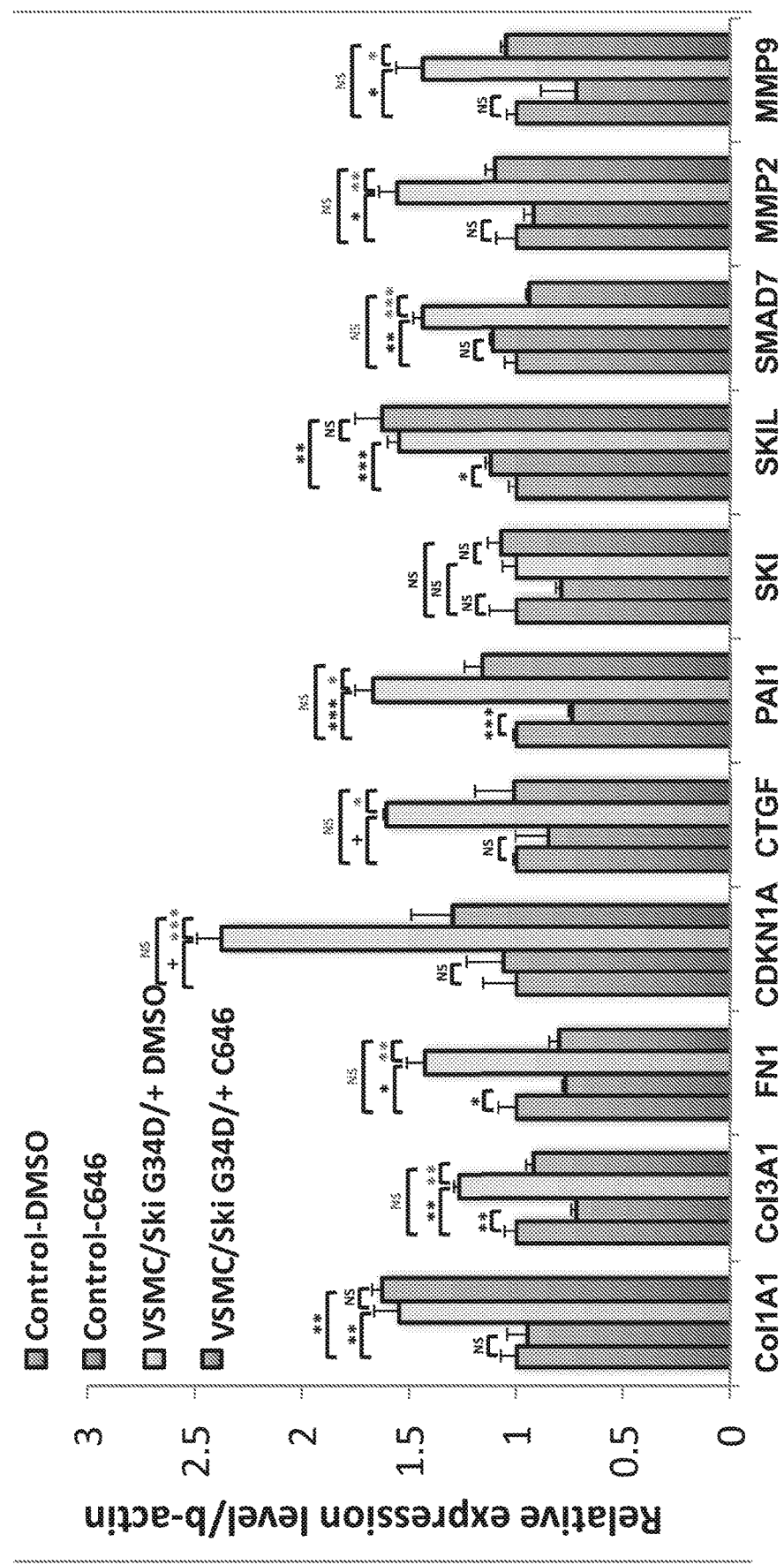

FIG. 24 is a graph showing the expression levels of TGFβ target genes relative to β-actin normalized to WT expression level (+/−SEM) determined by qPCR. Compared to control littermates, VSMC/Ski G34D/+ mice demonstrated a significantly increased expression level of TGFβ target genes. Also, compared with DMSO treated VSMC/Ski G34D/+ mice, C646 treated VSMC/Ski G34D/+ mice demonstrated decreased expression levels of TGFβ target genes except COL1A1, SKI and SKIL. *P<0.05; P<0.01; *P<0.001; +P<10$^{-4}$; ++P<10$^{-6}$; NS, not significant.

Figure 25:
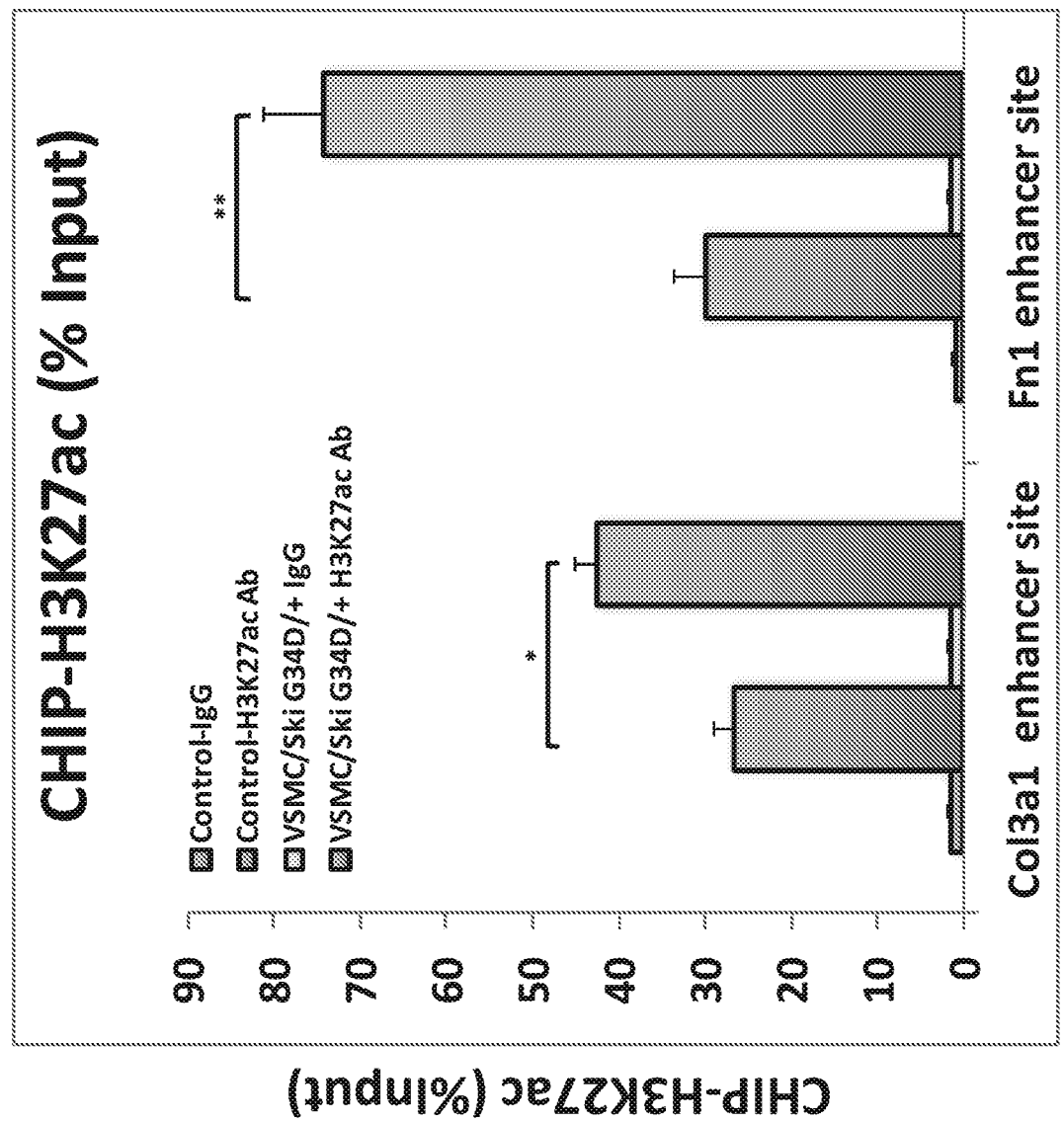

FIG. 25 is a graph showing increased acetylation of H3K27 (H3K27ac) at enhancers located proximal to the Col3a1 and Fn1 loci in the aortic root of each mouse lines by α-H3K27ac chromatin immunoprecipitation followed by qPCR (CHIP-qPCR). Compared with control littermates, aortic root of VSMC/Ski G34D/+ mice demonstrated a significantly increased acetylation of H3K27 at enhancers located proximal to the Col3a1 and Fn1 locus. *P<0.05; **P<0.01.

Figure 26:
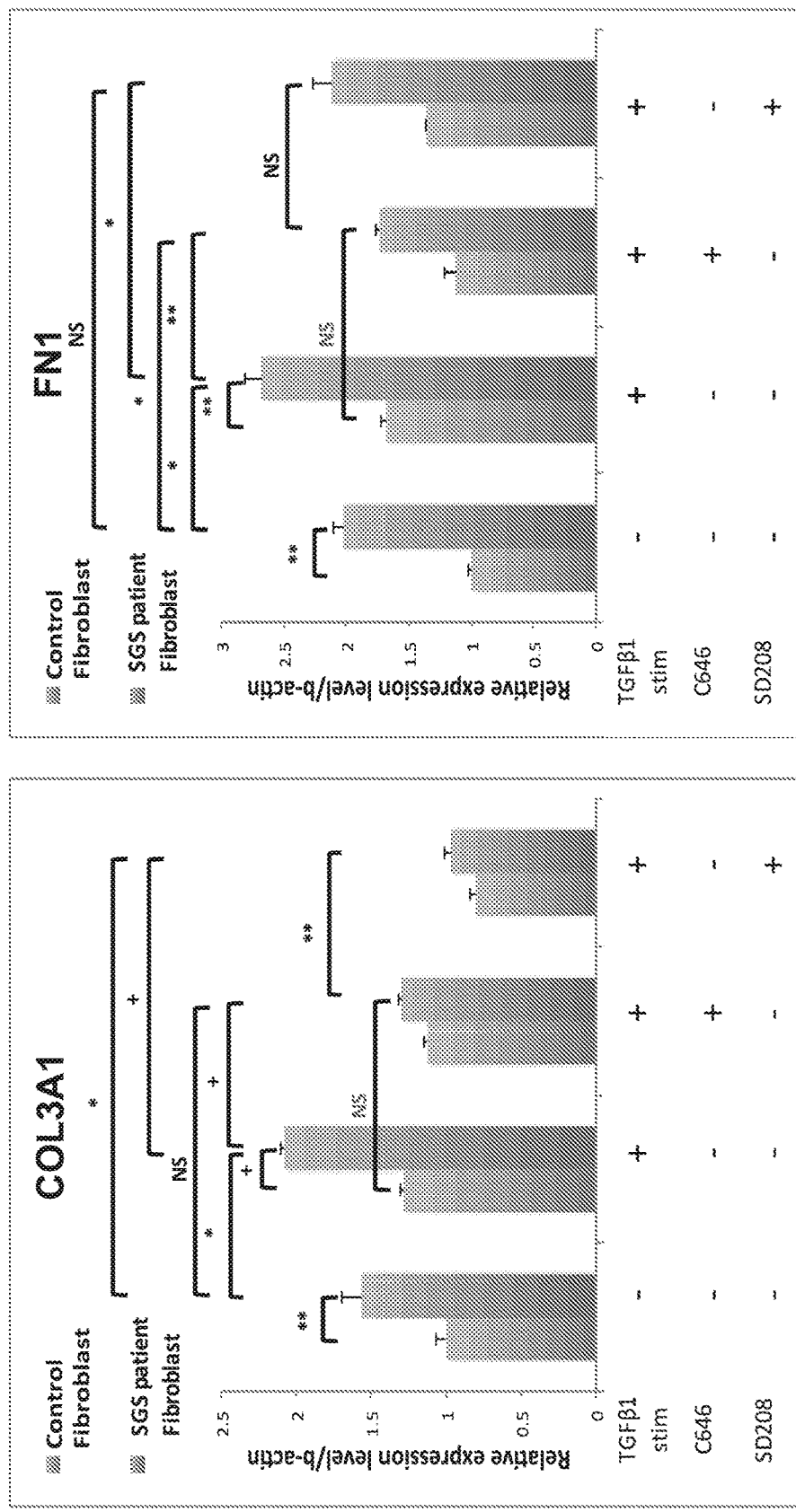

FIG. 26 are graphs showing the expression levels of COL3A1 and FN1 relative to that of β-actin in SGS patient fibroblasts normalized to expression levels of control human fibroblast (+/−SEM) determined by qPCR. Both of control fibroblast and SGS patient fibroblast compared between vehicle treated without TGFβ1 stimulation, vehicle treated with TGFβ1 stimulation (10 ng/ml for 6 hours), C646 treated (2004 for 24 hours of pre-treated before TGFβ1 stimulation) and SD208 (a TGFβ receptor kinase inhibitor) treated (10 μM for 1 hour of pre-treated before TGFβ1 stimulation) conditions. Compared with control fibroblasts, SGS patient fibroblasts demonstrated a significantly increased expression level of COL3A1 and FN1 with or without TGFβ1 stimulation. Compared with vehicle treated for both of control fibroblasts and SGS patient fibroblasts, both groups demonstrated a significantly decreased expression level of COL3A1 and FN1. Note that there is no significant difference of COL3A1 and FN1 expression level between C646 treated SGS patient fibroblast and vehicle treated control fibroblasts. *P<0.05; P<0.01; *P<0.001; +P<10$^{-4}$; ++P<10$^{-6}$; NS, not significant.

Figure 27:
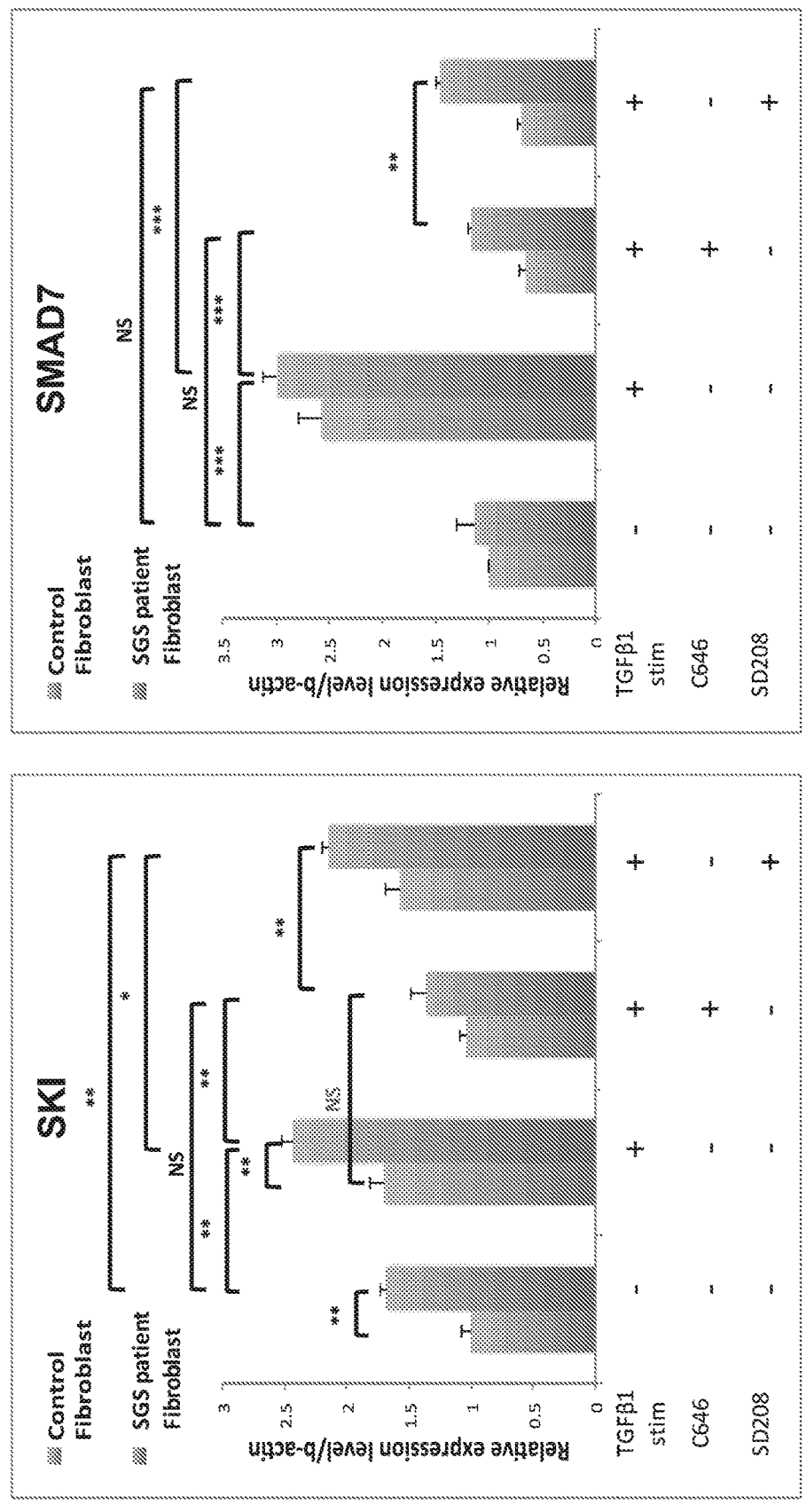

FIG. 27 are graphs showing the expression levels of SKI and SMAD7 relative to that of β-actin in SGS patient fibroblasts normalized to expression levels in control human fibroblasts (+/−SEM) determined by qPCR. Both control fibroblasts and SGS patient fibroblasts compared between vehicle treated without TGFβ1 stimulation, vehicle treated with TGFβ1 stimulation (10 ng/ml for 6 hours), C646 treated (2004 for 24 hours of pre-treated before TGFβ1 stimulation) and SD208 (a TGFβ receptor kinase inhibitor) treated (10 μM for 1 hour of pre-treated before TGFβ1 stimulation) conditions. Compared with control fibroblast, SGS patient fibroblast demonstrated a significantly increased expression level of SKI with or without TGFβ1 stimulation. Compared with vehicle treated for both of control fibroblast and SGS patient fibroblast, both fibroblast demonstrated a significantly decreased expression level of SKI and SMAD7. Note that there is no significant difference of SKI expression level between C646 treated SGS patient fibroblast and vehicle treated control fibroblast. *P<0.05; P<0.01; *P<0.001; +P<10$^{-4}$; ++P<10$^{-6}$; NS, not significant.

DETAILED DESCRIPTION

Embodiments of the invention are directed to methods and compositions for the prevention and treatment of inherited aortic aneurysm conditions by epigenetic modulation. The instant disclosure is based, at least in part, upon the discovery that treatment of mouse models of Shprintzen-Goldberg syndrome (SGS) with C646, a selective CBP/EP300 histone acetyl-transferase (HAT) inhibitor, normalizes gene expression in the aorta, preserves aortic wall architecture and abrogates aneurysm progression.

Accordingly, in certain embodiments, administration of agents that inhibit histone acetyl-transferase (HAT) expression and/or activity are therapeutic for a broad class of disorders that associate altered regulation of transforming growth factor β target genes with aortic aneurysm.

Transforming Growth Factor β and Aortic Aneurysm Syndromes

Transforming growth factor β (TGFβ) induced aortic aneurysm syndromes are unified by striking clinical overlap in craniofacial, skeletal, cutaneous and cardiovascular manifestations and a common mechanism, as evidenced by a uniform tissue signature for high TGFβ signaling in the aorta. Primary mutations occur in the genes encoding regulators of extracellular TGF bioavailability (FBN1 or BGN), TGF ligands (TGFB2 or TGFB3), TGF signaling effectors (TGFBR1, TGFBR2 or SMAD3), or regulators of the TGFβ transcriptional response (SKI). Discordance in the predicted signaling consequences of the underlying mutations and lack of precise pathogenic understanding has engendered ambiguity regarding the most promising treatment strategies. Shprintzen-Goldberg syndrome (SGS) shares most features of Marfan and Loeys-Dietz syndromes (MFS and LDS) with the added feature of intellectual disability. The underlying mutations in the Sloan-Kettering Institute proto-oncoprotein SKI occur in the Smad-binding domain and perturb recruitment of SKI to regulatory elements in TGFβ target genes. This leads to unopposed histone acetyltransferase (HAT) activity of EP300/CREB-binding protein (CBP), resulting in an amplified TGFβ transcriptional response. Mice heterozygous for a severe SGS mutation (Ski$^{G34D/+}$) phenocopy the human condition; conditional targeting specifically to vascular smooth muscle cells (Ski$^{VSMC:G34D/+}$) causes highly penetrant aortic root (AoR) aneurysm and dissection. This occurs in association with all of the histological and functional hallmarks of MFS and LDS, including aortic wall thickening caused by collagen accumulation, elastic fiber fragmentation and an overt mRNA signature for a TGFβ synthetic repertoire (TSR).

Without wishing to be bound by theory, it was hypothesized that HAT inhibitors (HATi) would have therapeutic potential. Remarkably, systemically-administered C646 (a selective EP300/CBP HATi) prevented aneurysm progression in Ski$^{VSMC:G34D/+}$ mice along with preservation of aortic wall architecture, prevention of excessive Histone 3 Lysine 27 (H3K27) acetylation (both globally and at TGFβ target gene enhancers) and normalization of the TSR. C646 also normalized TGFβ target gene expression in SGS patient fibroblasts with comparable efficiency of a TGFβ type I receptor (Alk5) kinase inhibitor. These data unambiguously implicate the TGFβ transcriptional response in the pathogenesis of AoR aneurysm and highlight novel therapeutic strategies aimed at epigenetic modulation.

Accordingly, in certain embodiments, a method for treating a subject having or at risk of developing a transforming growth factor β-associated disease, disorder and/or condition comprises administering to the subject an effective amount of one or more agents that modulate transforming growth factor β (TGFβ) expression by modulating the expression and/or activity of histone acetyl-transferase (HAT), thereby treating the subject.

In certain embodiments, a TGFβ associated disease is aortic aneurysm syndrome, and/or associated disorders thereof. Examples of an aortic aneurysm syndrome comprises Shprintzen-Goldberg syndrome (SGS), Marfan syndrome (MFS), Loeys-Dietz syndrome (LDS), Ehlers-Danlos syndrome (EDS), familial aortic dissection, or annuloaortic ectasia.

Histone acetyltransferases (HATs) modulate gene expression by catalyzing targeted acetylation of the ε-amino group of lysine residues on histones and nonhistone proteins. HATs can be classified into several families on the basis of number of highly conserved structural motifs. These include the GNAT family (Gcn5-related N-acetyltransferase e.g. Gcn5, PCAF), the MYST (MOZ, YBF2/SAS3 and TIP60) group and the p300/CBP family. The p300 and CBP are ubiquitously expressed, global transcriptional coactivators that have critical roles in a wide variety of cellular phenomenon including cell cycle control, differentiation and apoptosis. The transcriptional coactivator function of these two proteins is partially facilitated by their intrinsic HAT activity. p300/CBP also acetylates several nonhistone proteins with functional consequences. The most notable example is the acetylation of p53. p300/CBP directly interacts with p53 and acetylates the tumor suppressor in vivo and in vitro to enhance its transcriptional activation ability and consequently DNA repair.

In certain embodiments, an agent inhibits histone acetyltransferase (HAT) expression and/or activity as compared to a normal control and/or excessive acetylation of H3K27, for example at least a 5, 10, 20, 30, 40, 50, 60, 70, 80, 90 or 100% difference in HAT expression and/or activity as compared to a normal control. In some embodiments, the agent used in the methods and compositions disclosed herein is a selective inhibitor of EP300/CREB-binding protein (CBP) expression and/or activity as measured by TGFβ expression and/or activity. Other non-limiting examples of HAT inhibitors for use in the methods and compositions disclosed herein include anacardic acid, garcinol, curcumin, and quinolones. See, for example, F. Manzo et al., *Expert Opin Ther Pat.* (6):761-74 (2009).

CBP/P300 is the major enzyme that creates H3K27ac modification to enhancer sequences. In some embodiments, a selective EP300/CBP HAT inhibitor for use in the methods and compositions disclosed herein includes C646 (4-[(4Z)-4-[[5-(4,5-dimethyl-2-nitrophenyl)furan-2-yl]methylidene]-3-methyl-5-oxopyrazol-1-yl]benzoic acid) having the following structure:

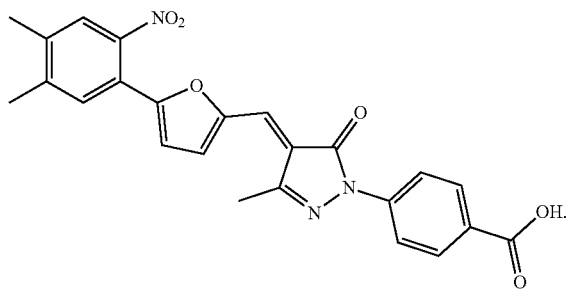 [SMILES: CC1=NN(c2ccc(C(=O)O)cc2)C(=O)/C1=C/c1ccc(-c2cc(C)c(C)cc2[N+](=O)[O-])o1]

In some embodiments, a selective EP300/CBP HAT for use in the methods and compositions disclosed herein includes an anacardic acid or a derivative thereof having a following formula:

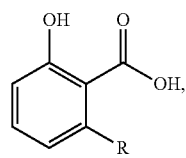

wherein R may be substituted or unsubstituted alkyl (e.g., $C_1$-$C_{30}$, $C_1$-$C_{20}$, $C_1$-$C_{15}$, $C_1$-$C_{12}$, $C_1$-$C_{10}$, or $C_1$-$C_8$), which may be saturated or unsaturated. For example, examplary anacardic acid may be

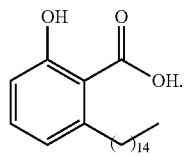

In some embodiments, a selective EP300/CBP HAT inhibitor for use in the methods and compositions disclosed herein includes garcinol ((1R,5R,7R)-3-(3,4-Dihydroxybenzoyl)-4-hydroxy-8,8-dimethyl-1,7-bis(3-methyl-2-buten-1-yl)-5-[(2S)-5-methyl-2-(1-methylethenyl)-4-hexen-1-yl]-Bicyclo[3.3.1]non-3-ene-2,9-dione, Camboginol) having the following structure:

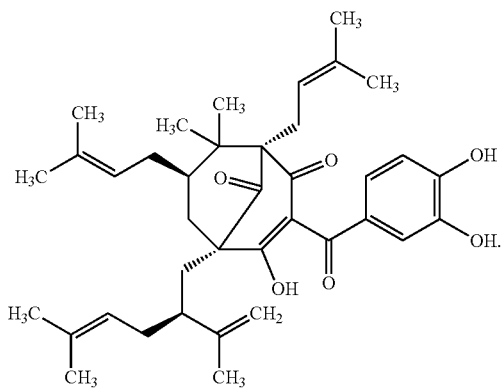 [SMILES: C=C(C)[C@@H](CC=C(C)C)C[C@@]12C[C@@H](CC=C(C)C)C(C)(C)[C@@](CC=C(C)C)(C(=O)C(C(=O)c3ccc(O)c(O)c3)=C1O)C2=O]

In some embodiments, a selective EP300/CBP HAT inhibitor for use in the methods and compositions disclosed herein includes curcumin ((1E,6E)-1,7-bis (4-hydroxy-3-methoxyphenyl)-1,6- heptadiene-3,5-dione, (1E,6E)-1,7-bis (4-hydroxy-3-methoxyphenyl)-1,6-heptadiene-3,5-dione, or diferuloylmethane) having the following structure:

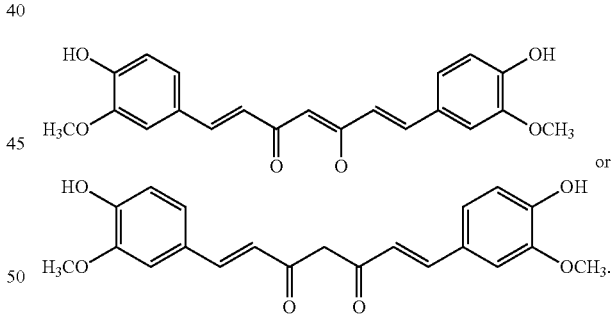

In some embodiments, a selective EP300/CBP HAT inhibitor for use in the methods and compositions disclosed herein includes MB-3 ((2R,3S)-rel-4-methylene-5-oxo-2-propyltetrahydrofuran-3-carboxylic acid) having the following structure:

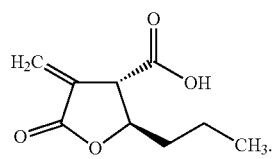

In some embodiments, a selective EP300/CBP HAT inhibitor for use in the methods and compositions disclosed herein includes isothiazolones having the following structure:

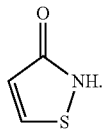

In some embodiments, a selective EP300/CBP HAT inhibitor for use in the methods and compositions disclosed herein includes quinolones such as 2-quinolone or 4-quinolone having the following structures:

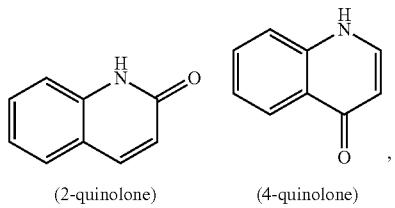

(2-quinolone)   (4-quinolone)

and isomers thereof.

In some embodiments, a selective EP300/CBP HAT inhibitor for use in the methods and compositions disclosed herein includes CPTH2 (2-[4-(4-chlorophenyl)-2-thiazolyl]hydrazone-cyclopentanone) having the following structure:

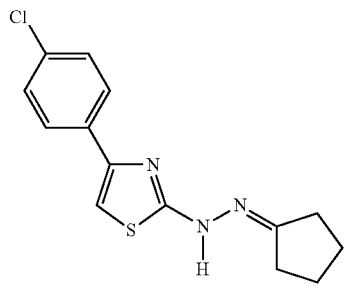 [SMILES: Clc1ccc(-c2csc(NN=C3CCCC3)n2)cc1]

and a pharmaceutically acceptable salt (e.g., 2-[4-(4-chlorophenyl)-2-thiazolyl]hydrazone-cyclopentanone monohydrochloride) thereof.

In some embodiments, a selective EP300/CBP HAT inhibitor for use in the methods and compositions disclosed herein includes MC2884 (1-benzyl-3,5-bis((E)-3-bromobenzylidene)piperidin-4-one) having the following structure:

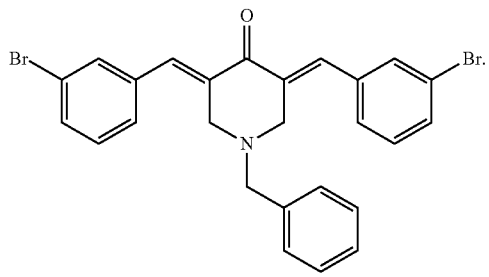 [SMILES: O=C1/C(=C/c2cccc(Br)c2)CN(Cc2ccccc2)C/C1=C\c1cccc(Br)c1]

In some embodiments, a selective EP300/CBP HAT inhibitor includes SPV106 (2-pentadecylidene-Propanedioic acid 1,3-diethyl ester) having the following structure:

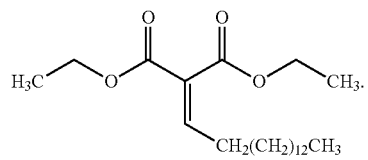

In some embodiments, a selective EP300/CBP HAT inhibitor for use in the methods and compositions disclosed herein includes L002 (4-[O-[(4-methoxyphenyl) sulfonyl]oxime]-2,6-dimethyl-2,5-cyclohexadiene-1,4-dione) having the following structure:

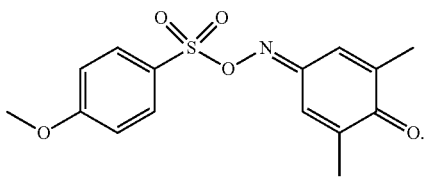

In some embodiments, a selective EP300/CBP HAT inhibitor for use in the methods and compositions disclosed herein includes windorphen ((Z)-3-Chloro-2,3-bis(4-methoxyphenyl)acrylaldehyde) having the following structure:

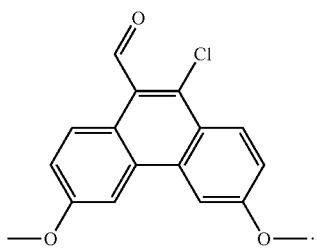

In some embodiments, a selective EP300/CBP HAT inhibitor for use in the methods and compositions disclosed herein includes PU-139 (2-(4-fluorophenyl)isothiazolo[5,4-b]pyridin-3(2H)-one) having the following structure:

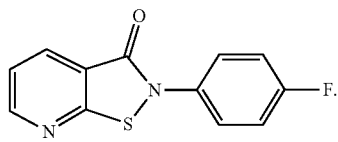 [SMILES: O=c1c2cccnc2sn1-c1ccc(F)cc1]

In some embodiments, a selective EP300/CBP HAT inhibitor i for use in the methods and compositions disclosed herein ncludes PU-141 (2-[[4-(trifluoromethyl)phenyl]methyl]isothiazolo[5,4-b]pyridin-3(2H)-one) having the following structure:

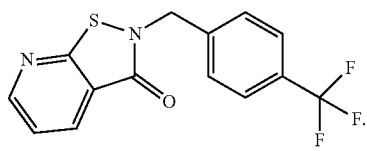 [SMILES: O=c1c2cccnc2sn1Cc1ccc(C(F)(F)F)cc1]

In some embodiments, a selective EP300/CBP HAT inhibitor for use in the methods and compositions disclosed herein includes TH1834 (2-[5-(4-{[(2-phenylethyl)({4-[4-(pyrrolidin-1-ylmethyl)phenoxy]butyl})amino]methyl}phenyl)-2H-1,2,3,4-tetrazol-2-yl] acetic acid hydrochloride) and a pharmaceutically acceptable salt thereof, for example, TH1834 dihydrochloride having the following structure:

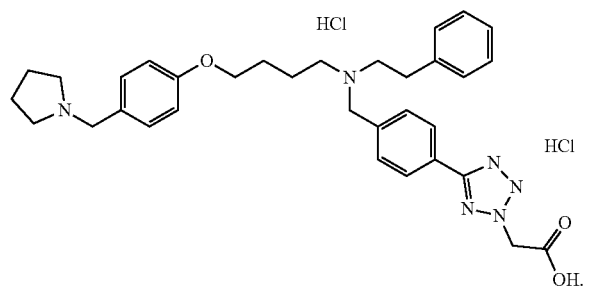 [SMILES: O=C(O)CN1N=C(c2ccc(CN(CCCCOc3ccc(CN4CCCC4)cc3)CCc3ccccc3)cc2)NN1 ; Cl ; Cl]

In some embodiments, a selective EP300/CBP HAT inhibitor for use in the methods and compositions disclosed herein includes A-485 ((1R)-N-[(4-fluorophenyl)methyl]-2,3-dihydro-5-[[(methylamino)carbonyl]amino]-2',4'-dioxo-N-[(1S)-2,2,2-trifluoro-1-methylethyl]spiro[1H-indene-1,5'-oxazolidine]-3'-acetamide) having the following structure:

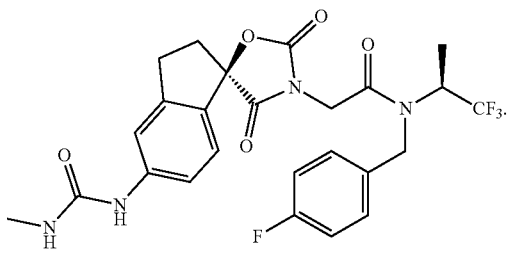 [SMILES: CNC(=O)Nc1ccc2c(c1)CC[C@@]21OC(=O)N(CC(=O)N(Cc2ccc(F)cc2)[C@@H](C)C(F)(F)F)C1=O]

In some embodiments, a selective EP300/CBP HAT inhibitor for use in the methods and compositions disclosed herein includes I-CBP112 (1-[7-(3,4-dimethoxyphenyl)-9-[[(3S)-1-methylpiperidin-3 -yl] methoxy] -2,3 ,4,5-tetrahydro- 1,4-benzoxazepin-4-yl]propan-1-one) having the following structure:

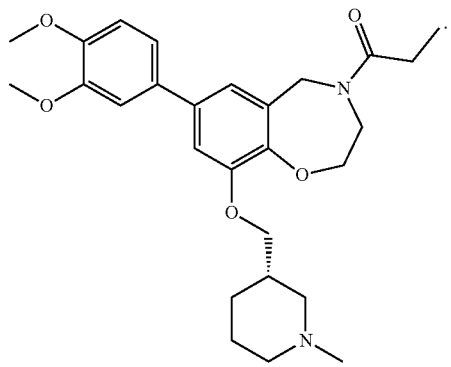 [SMILES: CCC(=O)N1CCOc2c(cc(-c3ccc(OC)c(OC)c3)cc2OC[C@H]2CCCN(C)C2)C1]

In some embodiments, a selective EP300/CBP HAT inhibitor for use in the methods and compositions disclosed herein includes CTPB (N-[4-chloro-3-(trifluoromethyl)phenyl]-2-ethoxy-6-pentadecyl-benzamide) having the following structure:

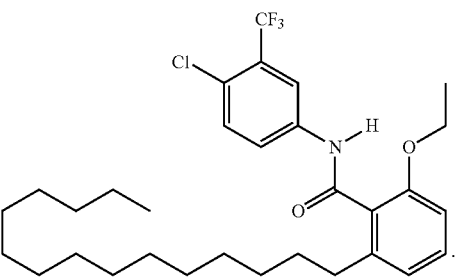 [SMILES: CCCCCCCCCCCCCCCc1cccc(OCC)c1C(=O)Nc1ccc(Cl)c(C(F)(F)F)c1]

In some embodiments, a selective EP300/CBP HAT inhibitor for use in the methods and compositions disclosed herein includes MG149 (2-[2-(4-heptylphenyl)ethyl]-6-hydroxy-benzoic acid) having the following structure:

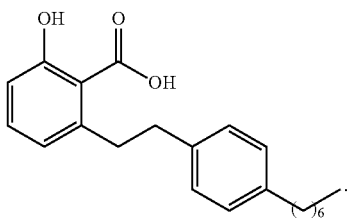

In some embodiments, a selective EP300/CBP HAT inhibitor includes remodelin (4-[2-(2-cyclopentylidenehydrazinyl)-4-thiazolyl]-benzonitrile) (4-[2-(2-cyclopentylidenehydrazinyl)-4-thiazolyl]-benzonitrile) having the following structure:

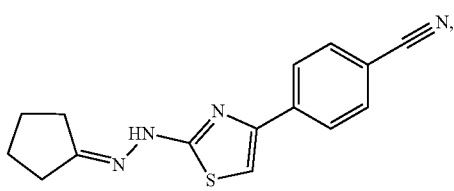 [SMILES: N#Cc1ccc(-c2csc(NN=C3CCCC3)n2)cc1]

or a pharmaceutically acceptable salt thereof (for example, 4-[2-(2-cyclopentylidenehydrazinyl)-4-thiazolyl]-benzonitrile, hydrobromide).

In some embodiments, a selective EP300/CBP HAT inhibitor includes EML 425 (5-[(4-hydroxy-2,6-dimethylphenyl)methylene]-1,3-bis(phenylmethyl)-2,4,6(1H,3H,5H)-pyrimidinetrione) having the following structure:

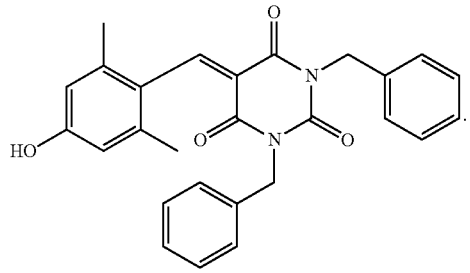 [SMILES: Cc1cc(O)cc(C)c1C=C1C(=O)N(Cc2ccccc2)C(=O)N(Cc2ccccc2)C1=O]

In some embodiments, a selective EP300/CBP HAT inhibitor includes ISOX DUAL ([3-[4-[2-[5-(dimethyl-1,2-oxazol-4-yl)-1-[2-(morpholin-4-yl)ethyl]-1H-1,3-benzodiazol-2-yl]ethyl]phenoxy]propyl]dimethylamine) having the following structure:

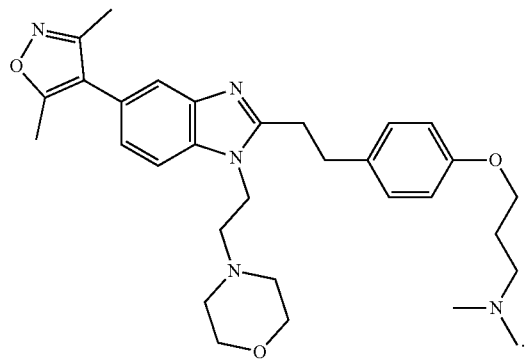 [SMILES: Cc1noc(C)c1-c1ccc2c(c1)nc(CCc1ccc(OCCCN(C)C)cc1)n2CCN1CCOCC1]

In some embodiments, a selective EP300/CBP HAT inhibitor includes Lys-CoA (S-[2-[[[(5S)-5-(acetylamino)-6-amino-6-oxohexyl]amino]-2-oxoethyl]coenzyme A trifluoroacetate), or its pharmaceutically acceptable salt (e.g., trifluoroacetate), having the following structure.

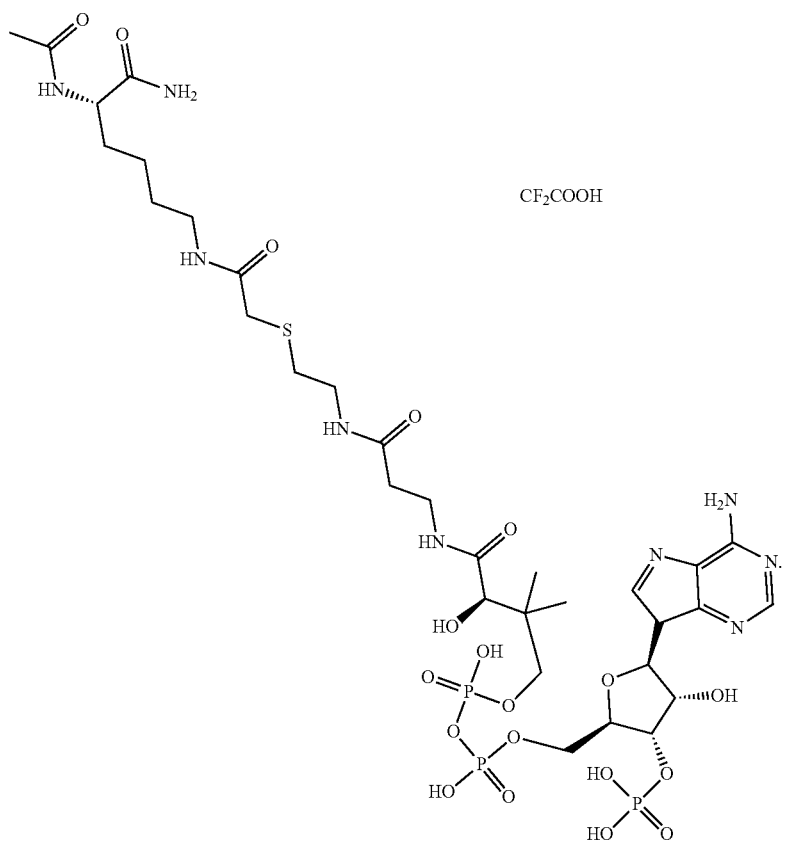 [SMILES: CC(=O)N[C@@H](CCCCNC(=O)CSCCNC(=O)CCNC(=O)[C@H](O)C(C)(C)COP(=O)(O)OP(=O)(O)OC[C@H]1O[C@@H](C2C=Nc3c(N)ncnc32)[C@H](O)[C@@H]1OP(=O)(O)O)C(N)=O ; "CF2COOH"]

In some embodiments, a selective EP300/CBP HAT inhibitor includes SGC-CBP30 (2-[2-(3-chloro-4-methoxyphenyl)ethyl]-5-(dimethyl-1,2-oxazol-4-yl)-1-[(2S)-2-(morpholin-4-yl)propyl]-1H-1,3-benzodiazole) having the following structure:

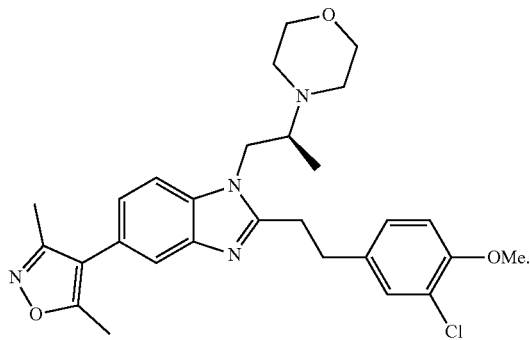 [SMILES: COc1ccc(CCc2nc3cc(-c4c(C)noc4C)ccc3n2C[C@H](C)N2CCOCC2)cc1Cl]

Agents useful in the methods of the disclosure can be small molecules, but can also be enzymes and/or nucleic acid molecules, e.g., antisense, ribozyme, or RNA interference technology, e.g., siRNA molecules corresponding to a portion of the nucleotide sequence encoding HAT.

Antisense polynucleotides may act by directly blocking translation by hybridizing to mRNA transcripts or degrading such transcripts of a gene. The antisense molecule may be recombinantly made using at least one functional portion of a gene in the antisense orientation as a region downstream of a promoter in an expression vector. Chemically modified bases or linkages may be used to stabilize the antisense polynucleotide by reducing degradation or increasing half-life in the body (e.g., methyl phosphonates, phosphorothioate, peptide nucleic acids). The sequence of the antisense molecule may be complementary to the translation initiation site (e.g., between −10 and +10 of the target's nucleotide sequence).

siRNA refers to double-stranded RNA of at least 20-25 basepairs which mediates RNA interference (RNAi). Duplex siRNA corresponding to a target RNA may be formed by separate transcription of the strands, coupled transcription from a pair of promoters with opposing polarities, or annealing of a single RNA strand having an at least partially self-complementary sequence. Alternatively, duplexed oligoribonucleotides of at least about 21 to about 23 basepairs may be chemically synthesized (e.g., a duplex of 21 ribonucleotides with 3' overhangs of two ribonucleotides) with some substitutions by modified bases being tolerated. Mismatches in the center of the siRNA sequence, however, abolishes interference. The region targeted by RNA interference should be transcribed, preferably as a coding region of the gene. Interference appears to be dependent on cellular factors (e.g., ribonuclease III) that cleave target RNA at sites 21 to 23 bases apart; the position of the cleavage site appears to be defined by the 5' end of the guide siRNA rather than its 3' end. Priming by a small amount of siRNA may trigger interference after amplification by an RNA-dependent RNA polymerase.

Nucleases: Any suitable nuclease system can be used including, for example, Argonaute family of endonucleases, clustered regularly interspaced short palindromic repeat (CRISPR) nucleases, zinc-finger nucleases (ZFNs), transcription activator-like effector nucleases (TALENs), meganucleases, other endo- or exo-nucleases, or combinations thereof. See Schiffer, 2012, *J Virol* 88(17):8920-8936, incorporated by reference. In certain embodiments, the system is an Argonaute nuclease system.

CRISPR-Cas: In certain aspects, inhibition of HAT can be achieved by administration of inhibitory nucleic acids (e.g., dsRNAs, siRNAs, antisense oligonucleotides, etc.) directed to inhibit HAT expression or activity. It is also contemplated that CRISPR-Cas (e.g., CRISPR-Cas9) methods can be used to excise and replace primary mutations that occur in the genes encoding regulators of extracellular TGFβ bioavailability (FBN1 or BGN), TGFβ ligands (TGFB2 or TGFB3), TGFβ signaling effectors (TGFBR1, TGFBR2 or SMAD3), or regulators of the TGFβ transcriptional response (SKI). Such methods can be performed upon the cells of a subject in vivo or ex vivo. Use of any combination of the above and/or other known inhibitor of HAT or TGFβ is also contemplated.

The CRISPR-Cas system is known in the art. Non-limiting aspects of this system are described in U.S. Pat. No. 8,697,359, issued Apr. 15, 2014, the entire content of which is incorporated herein by reference.

Non-limiting examples of Cas proteins include Cas1, Cas1B, Cas2, Cas3, Cas4, Cas5, Cas6, Cas7, Cas8, Cas9 (also known as Csn1 and Csx12), Cas 10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2. In some embodiments, the unmodified CRISPR enzyme has DNA cleavage activity, such as Cas9. In some embodiments, the CRISPR enzyme is Cas9, and may be Cas9 from *S. pyogenes* or *S. pneumoniae*. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In aspects of the invention, nickases may be used for genome editing via homologous recombination.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

Argonautes: Argonautes are a family of endonucleases that use 5' phosphorylated short single-stranded nucleic acids as guides to cleave targets (Swarts, D. C. et al. The evolutionary journey of Argonaute proteins. *Nat. Struct. Mol. Biol.* 21, 743-753 (2014)). Similar to Cas9, Argonautes have key roles in gene expression repression and defense against foreign nucleic acids (Swarts, D. C. et al. *Nat. Struct. Mol. Biol.* 21, 743-753 (2014); Makarova, K. S., et al. *Biol. Direct* 4, 29 (2009). Molloy, S. *Nat. Rev. Microbiol.* 11, 743 (2013); Vogel, J. *Science* 344, 972-973 (2014). Swarts, D. C. et al. *Nature* 507, 258-261 (2014); Olovnikov, I., et al. *Mol. Cell* 51, 594-605 (2013)). However, Argonautes differ from Cas9 in many ways (Swarts, D. C. et al. *Nat. Struct. Mol. Biol.* 21, 743-753 (2014)). Cas9 only exist in prokaryotes, whereas Argonautes are preserved through evolution and exist in virtually all organisms; although most Argonautes associate with single-stranded (ss)RNAs and have a central role in RNA silencing, some Argonautes bind ssDNAs and cleave target DNAs (Swarts, D. C. et al. *Nature* 507,258-261 (2014); Swarts, D. C. et al. *Nucleic Acids Res.* 43, 5120-5129 (2015)). guide RNAs must have a 3' RNA-RNA hybridization structure for correct Cas9 binding, whereas no specific consensus secondary structure of guides is required for Argonaute binding; whereas Cas9 can only cleave a target upstream of a PAM, there is no specific sequence on targets required for Argonaute. Once Argonaute and guides bind, they affect the physicochemical characteristics of each other and work as a whole with kinetic properties more typical of nucleic-acid-binding proteins (Salomon, W. E., et al. *Cell* 162, 84-95 (2015)).

Argonaute proteins typically have a molecular weight of ~100 kDa and are characterized by a Piwi-Argonaute-Zwille (PAZ) domain and a PIWI domain. Crystallographic studies of archaeal and bacterial Argonaute proteins revealed that the PAZ domain, which is also common to Dicer enzymes, forms a specific binding pocket for the 3'-protruding end of the small RNA with which it associates (Jinek and Doudna, (2009) *Nature* 457,405-412)). The structure of the PIWI domain resembles that of bacterial RNAse H, which has been shown to cleave the RNA strand of an RNA-DNA hybrid (Jinek and Doudna, (2009) *Nature* 457,405-412)). More recently, it was discovered that the catalytic activity of miRNA effector complexes, also referred to as Slicer activity, resides in the Argonaute protein itself.

Members of the human Ago subfamily, which consists of AGO1, AGO2, AGO3 and AGO4, are ubiquitously expressed and associate with miRNAs and siRNAs. Ago proteins are conserved throughout species, and many organisms express multiple family members, ranging from one in *Schizosaccharomyces pombe,* five in *Drosophila,* eight in humans, ten in Arabidopsis to twenty-seven in *C. elegans* (Tolia and Joshua-Tor, (2007) *Nat. Chem. Biol.* 3, 36-43). Argonaute proteins are also present in some species of budding yeast, including *Saccharomyces castellii.* It was found that *S. castellii* expresses siRNAs that are produced by a Dicer protein that differs from the canonical Dicer proteins found in animals, plants and other fungi (Drinnenberg et al., (2009) *Science* 326, 544-550).

More recently, structural studies have been extended to *Thermus thermophilus* Argonaute in complex with a guide strand only or a guide DNA strand and a target RNA duplex. This analysis revealed that the structure of the complex is divided into two lobes. One lobe contains the PAZ domain connected to the N-terminal domain through a linker region, L1. The second lobe consists of the middle (MID) domain (located between the PAZ and the PIWI domains) and the PIWI domain. The 5' phosphate of the small RNA, to which Argonaute binds, is positioned in a specific binding pocket in the MID domain (Jinek and Doudna, (2009) *Nature* 457, 405-412). The contacts between the Argonaute protein and the guide DNA or RNA molecule are dominated by interactions with the sugar-phosphate backbone of the small RNA or DNA; thus, the bases of the RNA or DNA guide strand are free for base pairing with the complementary target RNA. The structure indicates that the target mRNA base pairs with the guide DNA strand, but does not touch the protein (Wang et al., (2008a) *Nature* 456, 921-926; Wang, Y. et al., (2009) *Nat. Struct. Mol. Biol.* 16, 1259-1266; Wang et al., (2008b) *Nature* 456, 209-213).

The useful features of Argonaute endonucleases, e.g. *Natronobacterium gregoryi* Argonaute (NgAgo) for genome editing include the following: (i) NgAgo has a low tolerance to guide-target mismatch. (ii) 5' phosphorylated short ssDNAs are rare in mammalian cells, which minimizes the possibility of cellular oligonucleotides misguiding NgAgo. (iii) NgAgo follows a 'one-guide-faithful' rule, that is, a guide can only be loaded when NgAgo protein is in the process of expression, and, once loaded, NgAgo cannot swap its gDNA with other free ssDNA at 37° C.

Accordingly, in certain embodiments, Argonaute endonucleases comprise those which associate with single stranded RNA (ssRNA) or single stranded DNA (ssDNA). In certain embodiments, the Argonaute is derived from *Natronobacterium gregoryi.* In other embodiments. the *Natronobacterium gregoryi* Argonaute (NgAgo) is a wild type NgAgo, a modified NgAgo, or a fragment of a wild type or modified NgAgo. The NgAgo can be modified to increase nucleic acid binding affinity and/or specificity, alter an enzymatic activity, and/or change another property of the protein. For example, nuclease (e.g., DNase) domains of the NgAgo can be modified, deleted, or inactivated.

The wild type NgAgo sequence can be modified. The NgAgo nucleotide sequence can be modified to encode biologically active variants of NgAgo, and these variants can have or can include, for example, an amino acid sequence that differs from a wild type NgAgo by virtue of containing one or more mutations (e.g., an addition, deletion, or substitution mutation or a combination of such mutations). One or more of the substitution mutations can be a substitution (e.g., a conservative amino acid substitution). For example, a biologically active variant of an NgAgo polypeptide can have an amino acid sequence with at least or about 50% sequence identity (e.g., at least or about 50%, 55%, 60%, 65%, 70%, 75%, 80%, 85%, 90%, 95%, 97%, 98%, or 99% sequence identity) to a wild type NgAgo polypeptide. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. The amino acid residues in the NgAgo amino acid sequence can be non-naturally occurring amino acid residues. Naturally occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrrolysine can be used in place of lysine and selenocysteine can be used in place of cysteine). Non-naturally occurring amino acid residues are those that have not been found in nature, but that conform to the basic formula of an amino acid and can be incorporated into a peptide. These include D-alloisoleucine(2R,3S)-2-amino-3-methylpentanoic acid and Lcyclopentyl glycine (S)-2-amino-2-cyclopentyl acetic acid. For other examples, one can consult textbooks or the worldwide web (a site currently maintained by the California Institute of Technology displays structures of non-natural amino acids that have been successfully incorporated into functional proteins).

Candidate Therapeutic Agents

Candidate therapeutic agents can be screened using any number and types of assays. For example, high throughput functional genomics assays can be used to identify modulators of: HAT expression, TGFβ expression, acetylation of H3K27 or any combination thereof.

Any type of cell can be used, including ones which have been transformed with one or more vectors encoding the TGFβ nucleic acid sequences and/or HAT. Typically, in such assays the cells are contacted with a candidate therapeutic agent, such as for example, cDNA, a random peptide library (encoded by nucleic acids), antisense reagents, antibodies etc. In cases where the agents comprise a cDNA library, the cDNA library can comprise sense, antisense, full length, and truncated cDNAs. The peptide library is encoded by nucleic acids. The effect of the candidate therapeutic agent on TGFβ expression or the inhibition of HAT expression and/or activity, is then monitored. The effect of the agent can be validated and distinguished from somatic mutations, using, e.g., regulatable expression of the nucleic acid such as expression from a tetracycline promoter.

Proteins interacting with the peptide or with the protein encoded by the cDNA (e.g., distal enhancers) can be isolated using a yeast two-hybrid system, mammalian two hybrid system, or phage display screen, etc. Targets so identified can be further used as bait in these assays to identify additional members of the TGFβ regulatable pathways, which members are also targets for drug development (see, e.g., Fields et al., *Nature* 340:245 (1989); Vasavada et al., *Proc. Nat'l Acad. Sci.* USA 88:10686 (1991); Fearon et al., *Proc. Nat'l Acad. Sci.* USA 89:7958 (1992); Dang et al., *Mol. Cell. Biol.* 11:954 (1991); Chien et al., *Proc. Nat'l Acad. Sci.* USA 9578 (1991); and U.S. Pat. Nos. 5,283,173, 5,667,973, 5,468,614, 5,525,490, and 5,637,463).

In a preferred embodiment, a method of identifying therapeutic agents comprises contacting: culturing an isolated cell expressing HAT with a candidate therapeutic agent; determining whether (i) the agent modulates expression of TGFβ; and/or (ii) the agent modulates expression and/or activity of HAT; and/or (iii) the agent modulates acetylation of H3K27; and/or (iv) the agent is a selective inhibitor of EP300/CREB-binding protein (CBP) expression and/or activity; and/or (v) the agent normalizes TGFβ synthetic repertoire (TSR) expression, or any combination thereof; correlating HAT expression or activity and/or TGF expression in the presence or absence of a candidate therapeutic agent as compared to control cells, wherein a drug is identified based on desirable therapeutic outcomes.

Another suitable method for diagnosis and candidate drug discovery includes contacting a test sample with a cell expressing HAT, an allele or fragment thereof; and detecting interaction of the test sample with HAT sequences and/or transcriptional elements thereof, and/or expression of TGFβ, an allele or fragment thereof, and/or acetylation of H3K27. HAT, an allele or fragment thereof, or expression product thereof, can be detectably labeled e.g. with a fluorescent or radioactive component.

In another preferred embodiment, a cell from a patient is isolated and contacted with a candidate therapeutic molecule. The genes, expression products thereof, are monitored to identify which genes or expression products are regulated by the drug.

Nucleic Acid Microarrays: Identification of a nucleic acid sequence capable of binding to a HAT sequence can be achieved by immobilizing a library of nucleic acids onto the substrate surface so that each unique nucleic acid is located at a defined position to form an array. In general, the immobilized library of nucleic acids is exposed to a biomolecule or candidate agent under conditions which favored binding of the biomolecule to the nucleic acids. Non-specifically binding biomolecules could be washed away using mild to stringent buffer conditions depending on the level of specificity of binding desired. The nucleic acid array would then be analyzed to determine which nucleic acid sequences bound to the biomolecule. Preferably the biomolecules would carry a fluorescent tag for use in detection of the location of the bound nucleic acids. These molecules can then also be cross-tested in one or more assays to determine HAT expression and/or function and/or activity or any combination thereof.

An assay using an immobilized array of nucleic acid sequences may be used for determining the sequence of an unknown nucleic acid; single nucleotide polymorphism (SNP) analysis; analysis of gene expression patterns from a particular species, tissue, cell type, etc.; gene identification; etc.

Additional diagnostic uses for oligonucleotides designed from the sequences encoding a desired gene expression product may involve the use of PCR. These oligomers may be chemically synthesized, generated enzymatically, or produced in vitro. Oligomers will preferably contain a fragment of a polynucleotide encoding the expression products, or a fragment of a polynucleotide complementary to the polynucleotides, and will be employed under optimized conditions for identification of a specific gene. Oligomers may also be employed under less stringent conditions for detection or quantitation of closely-related DNA or RNA sequences.

In further embodiments, oligonucleotides or longer fragments derived from any of the polynucleotide sequences, may be used as targets in a microarray. The microarray can be used to monitor the identity and/or expression level of HAT and/or enhancer sequences, genes and gene transcripts simultaneously to identify any other genes with which target genes or its product interacts and/or to assess the efficacy of candidate therapeutic agents in regulating expression products of genes that mediate, for example, TGFβ-associated diseases or disorders.

Microarrays may be prepared, used, and analyzed using methods known in the art (see, e.g., Brennan et al., 1995, U.S. Pat. No. 5,474,796; Schena et al., 1996, *Proc. Natl. Acad. Sci.* U.S.A. 93: 10614-10619; Baldeschweiler et al., 1995, PCT application WO95/251116; Shalon, et al., 1995, PCT application WO95/35505; Heller et al., 1997, *Proc. Natl. Acad. Sci.* U.S.A. 94: 2150-2155; and Heller et al., 1997, U.S. Pat. No. 5,605,662). In other embodiments, a microarray comprises peptides, or other desired molecules which can be assayed to identify a candidate agent.

Candidate agents include numerous chemical classes, though typically they are organic compounds including small organic compounds, nucleic acids including oligonucleotides, and peptides. Small organic compounds suitably may have e.g. a molecular weight of more than about 40 or 50 yet less than about 2,500. Candidate agents may comprise functional chemical groups that interact with proteins and/or DNA.

Candidate agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of e.g. bacterial, fungal and animal extracts are available or readily produced.

Screening of therapeutic agent assays of the invention suitably include, animal models, cell-based systems and non-cell based systems. Preferably, identified genes, variants, fragments, or oligopeptides thereof are used for identifying agents of therapeutic interest, e.g. by screening libraries of compounds or otherwise identifying compounds of interest by any of a variety of drug screening or analysis techniques. The gene, allele, fragment, or oligopeptide thereof employed in such screening may be free in solution, affixed to a solid support, borne on a cell surface, or located intracellularly.

Another technique for drug screening provides for high throughput screening of compounds having suitable binding affinity to the protein of interest (see, e.g., Geysen et al., 1984, PCT application WO84/03564). In this method, large numbers of different small test compounds are synthesized on a solid substrate. The test compounds are reacted with identified genes, or fragments thereof, and washed. Bound molecules are then detected by methods well known in the art. Alternatively, non-neutralizing antibodies can be used to capture the peptide and immobilize it on a solid support.

The methods of screening of the invention comprise using screening assays to identify, from a library of diverse molecules, one or more compounds having a desired activity e.g. histone acetyltransferase activity. A "screening assay" is a selective assay designed to identify, isolate, and/or determine the structure of, compounds within a collection that have a preselected activity. By "identifying" it is meant that a compound having a desirable activity is isolated, its chemical structure is determined (including without limitation determining the nucleotide and amino acid sequences of nucleic acids and polypeptides, respectively) the structure of and, additionally or alternatively, purifying compounds having the screened activity). Biochemical and biological assays are designed to test for activity in a broad range of systems ranging from protein-protein interactions, enzyme catalysis, small molecule-protein binding, to cellular functions. Such assays include automated, semi-automated assays and HTS (high throughput screening) assays.

In HTS methods, many discrete compounds are preferably tested in parallel by robotic, automatic or semi-automatic methods so that large numbers of test compounds are screened for a desired activity simultaneously or nearly simultaneously. It is possible to assay and screen up to about 6,000 to 20,000, and even up to about 100,000 to 1,000,000 different compounds a day using the integrated systems of the invention.

Typically in HTS, target molecules are administered or cultured with isolated cells with modulated receptors, including the appropriate controls.

In one embodiment, screening comprises contacting each cell culture with a diverse library of member compounds, some of which are ligands of the target, under conditions where complexes between the target and ligands can form, and identifying which members of the libraries are present in such complexes. In another non limiting modality, screening comprises contacting a target enzyme with a diverse library of member compounds, some of which are inhibitors (or activators) of the target, under conditions where a product or a reactant of the reaction catalyzed by the enzyme produce a detectable signal. In the latter modality, inhibitors of target enzyme decrease the signal from a detectable product or increase a signal from a detectable reactant (or vice-versa for activators).

In one embodiment the invention provides soluble assays using an HAT nucleic acid sequence or product thereof, or a cell or tissue expressing an HAT protein, either naturally occurring or recombinant. In another embodiment, the invention provides solid phase based in vitro assays in a high throughput format, where the nucleic acid sequence and/or product and/or fragment thereof, is attached to a solid phase substrate. Any one of the assays described herein can be adapted for high throughput screening, e.g., ligand binding, TGFβ2 expression, enhancer function, acetylation/deacetylation state of an enhancer element of TGFβ2, TGFβ2 cell surface marker flux, radiolabeled ligand binding, second messenger flux, e.g., $Ca^{2+}$, cytokine production, etc.

In the high throughput assays of the invention, either soluble or solid state, it is possible to screen up to several thousand different modulators or ligands in a single day. This methodology can be used for proteins in vitro, or for cell-based or membrane-based assays. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non-covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder. A number of tags and tag binders can be used, based upon known molecular interactions well described in the literature. Similarly, any haptenic or antigenic compound can be used in combination with an appropriate antibody to form a tag/tag binder pair. Thousands of specific antibodies are commercially available and many additional antibodies are described in the literature Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Chemical Libraries: Developments in combinatorial chemistry allow the rapid and economical synthesis of hundreds to thousands of discrete compounds. These compounds are typically arrayed in moderate-sized libraries of small molecules designed for efficient screening. Combinatorial methods can be used to generate unbiased libraries suitable for the identification of novel compounds. In addition, smaller, less diverse libraries can be generated that are descended from a single parent compound with a previously determined biological activity. In either case, the lack of efficient screening systems to specifically target therapeutically relevant biological molecules produced by combinational chemistry such as inhibitors of important enzymes hampers the optimal use of these resources.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in a large number of combinations, and potentially in every possible way, for a given compound length (i.e., the number of amino acids in a polypeptide compound). Millions of chemical compounds can be synthesized through such combinatorial mixing of chemical building blocks.

A "library" may comprise from 2 to 50,000,000 diverse member compounds. Preferably, a library comprises at least 48 diverse compounds, preferably 96 or more diverse compounds, more preferably 384 or more diverse compounds, more preferably, 10,000 or more diverse compounds, preferably more than 100,000 diverse members and most preferably more than 1,000,000 diverse member compounds. By "diverse" it is meant that greater than 50% of the compounds in a library have chemical structures that are not identical to any other member of the library. Preferably, greater than 75% of the compounds in a library have chemical structures that are not identical to any other member of the collection, more preferably greater than 90% and most preferably greater than about 99%.

The preparation of combinatorial chemical libraries is well known to those of skill in the art. For reviews, see Thompson et al., Synthesis and application of small molecule libraries, *Chem Rev* 96:555-600, 1996; Kenan et al., Exploring molecular diversity with combinatorial shape libraries, *Trends Biochem Sci* 19:57-64, 1994; Janda, Tagged versus untagged libraries: methods for the generation and screening of combinatorial chemical libraries, *Proc Natl Acad Sci USA.* 91:10779-85, 1994; Lebl et al., One-bead-one-structure combinatorial libraries, *Biopolymers* 37:177-98, 1995; Eichler et al., Peptide, peptidomimetic, and organic synthetic combinatorial libraries, *Med Res Rev.* 15:481-96, 1995; Chabala, Solid-phase combinatorial chemistry and novel tagging methods for identifying leads, *Curr Opin Biotechnol.* 6:632-9, 1995; Dolle, Discovery of enzyme inhibitors through combinatorial chemistry, *Mol Divers.* 2:223-36, 1997; Fauchere et al., Peptide and non-peptide lead discovery using robotically synthesized soluble libraries, Can J. Physiol Pharmacol. 75:683-9, 1997; Eichler et al., Generation and utilization of synthetic combinatorial libraries, *Mol Med Today* 1: 174-80, 1995; and Kay et al., Identification of enzyme inhibitors from phage-displayed combinatorial peptide libraries, *Comb Chem High Throughput Screen* 4:535-43, 2001.

Other chemistries for generating chemical diversity libraries can also be used. Such chemistries include, but are not limited to, peptoids (PCT Publication No. WO 91/19735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., *Proc. Nat. Acad. Sci. USA,* 90:6909-6913 (1993)); vinylogous polypeptides (Hagihara, et al., *J. Amer. Chem. Soc.* 114:6568 (1992)); nonpeptidal peptidomimetics with .beta.-D-glucose scaffolding (Hirschmann, et al., *J. Amer. Chem. Soc.,* 114:9217-9218 (1992)); analogous organic syntheses of small compound libraries (Chen, et al., *J. Amer. Chem. Soc.,* 116:2661 (1994)); oligocarbamates (Cho, et al., *Science,* 261:1303 (1993)); and/or peptidyl phosphonates (Campbell, et al., *J. Org. Chem.* 59:658 (1994)); nucleic acid libraries (see, Ausubel, Berger and Sambrook, all supra); peptide nucleic acid libraries (see, e.g., U.S. Pat. No. 5,539, 083); antibody libraries (see, e.g., Vaughn, et al., *Nature Biotechnology,* 14(3):309-314 (1996) and PCT/US96/ 10287); carbohydrate libraries (see, e.g., Liang, et al., *Sci-* ence, 274:1520-1522 (1996) and U.S. Pat. No. 5,593,853); small organic molecule libraries (see, e.g., benzodiazepines, Baum C&E News, January 18, page 33 (1993); isoprenoids (U.S. Pat. No. 5,569,588); thiazolidinones and metathiazanones (U.S. Pat. No. 5,549,974); pyrrolidines (U.S. Pat. Nos. 5,525,735 and 5,519,134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Bio sciences, Columbia, Md., etc.).

High throughput screening can be used to measure the effects of drugs on complex molecular events, e.g. regulation of HAT expression by one or a multitude of transcriptional regulators of HAT. Multicolor fluorescence permits multiple targets and cell processes to be assayed in a single screen. Cross-correlation of cellular responses will yield a wealth of information required for target validation and lead optimization.

In another aspect, the present invention provides a method for analyzing cells comprising providing an array of locations which contain multiple cells wherein the cells contain one or more fluorescent reporter molecules; scanning multiple cells in each of the locations containing cells to obtain fluorescent signals from the fluorescent reporter molecule in the cells; converting the fluorescent signals into digital data; and utilizing the digital data to determine the distribution, environment or activity of the fluorescent reporter molecule within the cells.

A major component of the new drug discovery paradigm is a continually growing family of fluorescent and luminescent reagents that are used to measure the temporal and spatial distribution, content, and activity of intracellular ions, metabolites, macromolecules, and organelles. Classes of these reagents include labeling reagents that measure the distribution and amount of molecules in living and fixed cells, environmental indicators to report signal transduction events in time and space, and fluorescent protein biosensors to measure target molecular activities within living cells. A multiparameter approach that combines several reagents in a single cell is a powerful new tool for drug discovery.

This method relies on the high affinity of fluorescent or luminescent molecules for specific cellular components. The affinity for specific components is governed by physical forces such as ionic interactions, covalent bonding (which includes chimeric fusion with protein-based chromophores, fluorophores, and lumiphores), as well as hydrophobic interactions, electrical potential, and, in some cases, simple entrapment within a cellular component. The luminescent probes can be small molecules, labeled macromolecules, or genetically engineered proteins, including, but not limited to green fluorescent protein chimeras.

Those skilled in this art will recognize a wide variety of fluorescent reporter molecules that can be used in the present invention, including, but not limited to, fluorescently labeled biomolecules such as proteins, phospholipids, RNA and DNA hybridizing probes. Similarly, fluorescent reagents specifically synthesized with particular chemical properties of binding or association have been used as fluorescent reporter molecules (Barak et al., (1997), *J. Biol. Chem.* 272:27497-27500; Southwick et al., (1990), *Cytometry* 11:418-430; Tsien (1989) in *Methods in Cell Biology, Vol.* 29 Taylor and Wang (eds.), pp. 127-156). Fluorescently labeled antibodies are particularly useful reporter molecules due to their high degree of specificity for attaching to a single molecular target in a mixture of molecules as complex as a cell or tissue. The luminescent probes can be synthesized within the living cell or can be transported into the cell via several non-mechanical modes including diffusion, facilitated or active transport, signal-sequence-mediated transport, and endocytotic or pinocytotic uptake. Mechanical bulk loading methods, which are well known in the art, can also be used to load luminescent probes into living cells (Barber et al. (1996), *Neuroscience Letters* 207:17-20; Bright et al. (1996), *Cytometry* 24:226-233; McNeil (1989) in *Methods in Cell Biology, Vol.* 29, Taylor and Wang (eds.), pp. 153-173). These methods include electroporation and other mechanical methods such as scrape-loading, bead-loading, impact-loading, syringe-loading, hypertonic and hypotonic loading. Additionally, cells can be genetically engineered to express reporter molecules, such as GFP, coupled to a protein of interest as previously described (Chalfie and Prasher U.S. Pat. No. 5,491,084; Cubitt et al. (1995), *Trends in Biochemical Science* 20:448-455).

Once in the cell, the luminescent probes accumulate at their target domain as a result of specific and high affinity interactions with the target domain or other modes of molecular targeting such as signal-sequence-mediated transport. Fluorescently labeled reporter molecules are useful for determining the location, amount and chemical environment of the reporter. For example, whether the reporter is in a lipophilic membrane environment or in a more aqueous environment can be determined (Giuliano et al. (1995), *Ann. Rev. of Biophysics and Biomolecular Structure* 24:405-434; Giuliano and Taylor (1995), *Methods in Neuroscience* 27.1-16). The pH environment of the reporter can be determined (Bright et al. (1989), *J. Cell Biology* 104:1019-1033; Giuliano et al. (1987), *Anal. Biochem.* 167:362-371; Thomas et al. (1979), *Biochemistry* 18:2210-2218). It can be determined whether a reporter having a chelating group is bound to an ion, such as $Ca^{++}$, or not (Bright et al. (1989), In*Methods in Cell Biology,* Vol. 30, Taylor and Wang (eds.), pp. 157-192; Shimoura et al. (1988), *J. of Biochemistry* (Tokyo) 251:405-410; Tsien (1989) In *Methods in Cell Biology,* Vol. 30, Taylor and Wang (eds.), pp. 127-156).

Those skilled in the art will recognize a wide variety of ways to measure fluorescence. For example, some fluorescent reporter molecules exhibit a change in excitation or emission spectra, some exhibit resonance energy transfer where one fluorescent reporter loses fluorescence, while a second gains in fluorescence, some exhibit a loss (quenching) or appearance of fluorescence, while some report rotational movements (Giuliano et al. (1995), *Ann. Rev. of Biophysics and Biomol. Structure* 24:405-434; Giuliano et al. (1995), *Methods in Neuroscience* 27:1-16).

The whole procedure can be fully automated. For example, sampling of sample materials may be accomplished with a plurality of steps, which include withdrawing a sample from a sample container and delivering at least a portion of the withdrawn sample to test cell culture (e.g., a cell culture wherein gene expression is regulated). Sampling may also include additional steps, particularly and preferably, sample preparation steps. In one approach, only one sample is withdrawn into the auto-sampler probe at a time and only one sample resides in the probe at one time. In other embodiments, multiple samples may be drawn into the auto-sampler probe separated by solvents. In still other embodiments, multiple probes may be used in parallel for auto sampling.

In the general case, sampling can be effected manually, in a semi-automatic manner or in an automatic manner. A sample can be withdrawn from a sample container manually, for example, with a pipette or with a syringe-type manual probe, and then manually delivered to a loading port or an injection port of a characterization system. In a semi-automatic protocol, some aspect of the protocol is effected automatically (e.g., delivery), but some other aspect requires manual intervention (e.g., withdrawal of samples from a process control line). Preferably, however, the sample(s) are withdrawn from a sample container and delivered to the characterization system, in a fully automated manner—for example, with an auto-sampler.

Labels: The particular label or detectable moiety or tag used in the assay is not a critical aspect of the invention. The detectable group can be any material having a detectable physical or chemical property. Such detectable labels have been well developed in the field of immunoassays and, in general, most labels useful in such methods can be applied to the present invention. Thus, a label is any composition detectable by spectroscopic, photochemical, biochemical, immunochemical, electrical, optical, or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horseradish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound.

The molecules can also be conjugated directly to signal generating compounds, e.g., by conjugation with an enzyme or fluorophore. Any type of enzyme label can be used as long as they do not interfere with one of the desired outputs of the assay, e.g. HAT expression and/or enhancer function and/or acetylation/deacetylation state of an enhancer element of HAT fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge-coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Methods of Treatment

As used herein, the term "TGFβassociated disease, disorder and/or condition" is intended to mean any disease, disorder and/or condition that has been identified or may be identified as associated with altered expression and/or activity of TGFβ.

The agents and pharmaceutical compositions of the disclosure can be administered to a subject to treat or prevent diseases, disorders and conditions associated with aberrant expression or activity of TGFβ. In one embodiment, the agents and pharmaceutical compositions are used to treat or prevent aortic aneurysm syndrome, and/or associated disorders thereof. Examples of an aortic aneurysm syndrome comprises Shprintzen-Goldberg syndrome (SGS), Marfan syndrome (MFS), Loeys-Dietz syndrome (LDS), Ehlers-Danlos syndrome (EDS), familial aortic dissection, or annuloaortic ectasia.

In one embodiment, the agents or pharmaceutical compositions are administered in an effective amount using a dosing schedule determined by a medical provider to treat or prevent a disease or disorder set forth herein. The agents or pharmaceutical compositions can be administered in a variety of methods, as described herein and known to one of skill in the art.

In one aspect, the disclosure provides a method for treating or preventing in a subject, a disease or condition associated with aberrant expression or activity of TGFβ, or a gene product thereof, by administering to the subject an agent which modulates HAT expression and/or activity. Subjects at risk for a disease which is caused or contributed to by aberrant expression or activity of TGFβ, or a gene product thereof, can be identified by, for example, any or a combination of diagnostic or prognostic assays as described herein.

Administration of a prophylactic agent can occur prior to the manifestation of symptoms characteristic of the aberrancy of expression or activity of HAT and/or TGFβ, such that a disease or disorder is prevented or, alternatively, delayed in its progression.

Another aspect of the disclosure pertains to methods of modulating expression or activity of a regulator of HAT, for therapeutic purposes. Accordingly, in an exemplary embodiment, the modulatory method of the disclosure involves contacting a cell with an agent that modulates one or more of the activities of HAT. An agent that modulates expression or activity of HAT can be an agent as described herein, such as a small molecule, nucleic acid or polypeptide. In one embodiment, the agent inhibits one or more activities of HAT. These modulatory methods can be performed in vitro (e.g., by culturing the cell with the agent) or, alternatively, in vivo (e.g., by administering the agent to a subject). As such, the present disclosure provides methods of treating an individual afflicted with a disease or disorder characterized by aberrant TGFβ expression, e.g., aortic aneurysm syndrome, and/or associated disorders thereof. In one embodiment, the method involves administering an agent, or combination of agents that modulates In certain embodiments, a method for treating a subject having or at risk of developing a transforming growth factor β-associated disease, disorder and/or condition comprises administering to the subject an effective amount of one or more agents that modulate transforming growth factor β (TGFβ) expression by modulating the expression and/or activity of histone acetyl-transferase (HAT), thereby treating the subject.

The disclosure further provides kits comprising agents or pharmaceutical compositions of the disclosure and instructions for use. In one embodiment, the kits of the disclosure are for the treatment of diseases and disorders characterized by aberrant TGFβ expression.

Pharmaceutical Compositions of the Invention

The agents described herein can be formulated into pharmaceutical compositions for the treatment of the diseases, disorders and conditions disclosed herein. The language "pharmaceutical composition" includes preparations suitable for administration to mammals, e.g., humans. When the compounds used in the methods of the present disclosure are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present disclosure to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present disclosure include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present disclosure with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. A compound of the present disclosure may also be administered as a bolus, electuary or paste.

In solid dosage forms of the disclosure for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the disclosure include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert dilutents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the disclosure for rectal or vaginal administration may be presented as a suppository, which may be prepared by mixing one or more compounds of the disclosure with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present disclosure which are suitable for vaginal administration also include pessaries, tampons, creams, gels, pastes, foams or spray formulations containing such carriers as are known in the art to be appropriate.

Dosage forms for the topical or transdermal administration of a compound of this disclosure include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this disclosure, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this disclosure.

Pharmaceutical compositions of this disclosure suitable for parenteral administration comprise one or more compounds of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue, The preparations of the present disclosure may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present disclosure, which may be used in a suitable hydrated form, and/or the pharmaceutical compositions of the present disclosure, are formulated into pharmaceutically acceptable dosage forms by conventional methods known to those of skill in the art.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present disclosure employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In general, a suitable daily dose of a compound of the disclosure will be that amount of the compound that is the lowest dose effective to produce a therapeutic effect. Such an effective dose will generally depend upon the factors described above. Generally, intravenous and subcutaneous doses of the compounds of this disclosure for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day.

An effective amount is that amount treats a disease, disorder or condition set forth herein.

If desired, the effective daily dose of the active compound may be administered as two, three, four, five, six or more sub-doses administered separately at appropriate intervals throughout the day, optionally, in unit dosage forms.

While it is possible for a compound of the present disclosure to be administered alone, it is preferable to administer the compound as a pharmaceutical composition.

Certain aspects of the disclosure involve administration of nucleic acid agents. Nucleic acid agents can be effectively delivered to a subject as stabilized agents, with such stability often provided via lipid nanoparticle (LNP) encasement of active nucleic acid agents and/or modification of therapeutic nucleic acid agents with one or more stabilizing modifications, including, e.g., 2'-O-alkyl modifications (including 2'-O-methyl), 2'-F modifications, backbone modifications, locked nucleic acid (LNA) configurations, GalNAc modifications, cholesterol conjugates, etc. Such modifications are known in the art and can be readily employed by the skilled artisan for delivery of the nucleic acid agents of the instant disclosure.

All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Mouse Lines

All mice were cared for under strict compliance with the Animal Care and Use Committee of the Johns Hopkins University School of Medicine. $Ski^{G34D/+}$ mice were generated by homologous recombination as described in the next section.

$Ski^{tm1a(EUCOMM)Hmgu}$ (tm1a represents targeted mutation 1a, and hmgu represents Helmholtz Zentrum Muenchen GmbH) ES cells were obtained from the European Conditional Mouse Mutagenesis Program and injected into the cavity of day 3.5-balstocysts from C57BL/6J mice at the Johns Hopkins University School of Medicine transgenic core. Male chimeras were mated with C57BL/6J wild-type female mice to establish germline transmission. LacZ-Neo cassette was removed by crossing with FlpO deleter stain (B6.Cg-Tg(Pgk1-flpo)10Sykr/J, #011065) purchased from the Jackson Laboratory and to generate Ski +/− mice, exon 2 and 3 of Ski gene flanking by loxP sequences was removed by crossing with Cre deleter stain (B6.C-Tg(CMV-cre) 1Cgn/J, #006054) purchased from the Jackson Laboratory, followed by mating to C57BL/6J strain at least five generations. Mef2c-Cre mouse sperm (Tg(Mef2c-cre)2Blk, # 030262-UNC) was purchased from the Mutant Mouse Regional Resource Centers (MMRRC). A colony was established following rederivation by in vitro fertilization of C57BL/6J oocytes. Wnt1-Cre mice (B6.Cg-Tg(Wnt1-cre) 2Sor/J, #022501) and Sm22α-Cre mice (B6.Cg-Tg(Tagln-cre)1Her/J, #017491) were purchased from the Jackson Laboratory, followed by mating to C57BL/6J strain at least five generations. To minimize potentially confounding background effects, all comparisons between genotypes and between treatment arms within a genotype were made between gender-matched littermates.

Mice were checked daily for evidence of premature lethality. At the end of a drug trial, all mice were euthanized through inhalational halothane (Sigma) or anesthetized with isofluorane. Following sacrifice, mice underwent immediate laparotomy, descending abdominal aortic transection, and PBS (pH 7.4) was infused throughout the vascular tree via the left ventricle. For aorta frozen section, additional 4% paraformaldehyde in PBS was infused again for fixation tissue. Sacrificed mice used for three harvest methods, latex infusion for histological analysis, freezing heart and aorta embedded in optimal cutting temperature compound (O.C.T compound) for immunofluorescent staining and in situ hybridization and snap-frozen aorta in liquid nitrogen.

For quantitative RT-PCR and chromatin immunoprecipitation, mice aortic root and ascending aorta (above aortic root to the origin of right brachiocephalic trunk) harvested separately, snap-frozen in liquid nitrogen and stored at minus 80 degrees Celsius until processed. For RNA extraction, Aortas were homogenized in Trizol (ThermoFisher) by FastPrep-24 (MP Biomedicals, LLC.), as per the manufacturer's manual. After homogenization, RNA was extracted by RNeasy mini kit (QIAGEN), as per the manufacturer's manual. RNA samples were then stored once more at minus 80 degrees until quantitative RT-PCR experiment was performed.

For aorta frozen section, harvested aorta with heart was fixed in fresh 4% paraformaldehyde in PBS at 4 degree overnight and then placed in cold 30% sucrose in PBS solution and incubated at 4 degree overnight again. Tissue was then embedded in Tissue-Tek O.C.T compound ad snap-frozen in liquid nitrogen and stored at minus 80 degree until processed.

According to a previously described protocol with slight modification (1), mice that were analyzed for aortic histology had latex infused into the left ventricle through descending abdominal aorta. Mice were then fixed for 24 hours in 10% neutral buffered formalin and then switched into 70% ethanol until histological analysis was performed.

Generation of Ski $^{G34D/+}$ mice

Ski$^{G34D/+}$ mice were generated by homologous recombination. A 10 kilo-bases Ski fragment was generated by PCR from mouse ES cell DNA. The amplicon was subcloned into pCR2.1-TOPO (Invitrogen Corp.) Site-directed mutagenesis was performed with the In-Fusion HD kit (Clontech Inc.), creating G34D mutation. The Neo cassette was amplified from pMC lneo-polyA vector (Stratagene Inc.) and the fragment containing Sal1 restriction site and Neo cassette with flanking loxP sequences was subcloned into a unique Sal1 site in the Ski intron after exon 1. All targeting vector sequence including the sequences of the loxP sites and site-directed mutagenesis-created mutations were confirmed by sanger sequencing. The vector was linearized using a unique (EcoR1) site and electroporated into R1 embryonic stem cells. Positive clones were identified by PCR test. Positives clones were injected into 129S6/ScEvTac blastocysts at embryonic day 3.5 and transferred into pseudopregnant females. Chimeric offspring were mated to C57BL/6J mice, and germline transmission was observed for at least three independent targeting events for mutant genotype. All exons encompassed by and immediately flanking the targeting vector were analyzed by sequencing of PCR-amplified genomic DNA derived from mutant mice to demonstrate the fidelity of targeting. Mice were genotyped on the basis of creation of a new BamH1 site in correctly targeted mice. Primers used for amplification were 5'-GAGCCCGATCG CACCATGGAA-3' (sense; SEQ ID NO: 1) and 5'-AAGAGATGGTCTCCCCTTCC-3' (antisense; SEQ ID NO: 2). For testing random insertion of linearized targeted vector, quantitative PCR of Neo cassette sequence was performed with previously verified DNA sample which contained only single Neo cassette sequence. The loxP-flanked Neo cassette was removed by crossing with Cre deleter stain either CMV-Cre (B6.C-Tg(CMV-cre)1Cgn/J, #006054) purchased from the Jackson Laboratory, followed by mating to C57BL/6J strain at least five generations for C57BL/6J genetic background or Prm-Cre (1295/Sv-Tg (Prm-cre)580g/J, #003328) purchased from Jackson Laboratory, followed by mating to 12956/ScEvTac strain at least five generations for 12956/ScEvTac genetic background. 12956/ScEvTac genetic background Ski $^{G34D/+}$ mice were used for dermal, skeletal and cardiovascular phenotypes analyses and C57BL/6J genetic background Ski $^{G34D/+}$ mice were used for behavioral phenotype analysis. Ski G34D/+: Neo mice were bred to 12956/ScEvTac strain at least five generations without deletion of Neo cassette as a separate mouse line. Complete concordance of phenotype for three or two independent lines and backcrossing to each congenic inbred strains at least five generations excluded any major off-target effect.

Mouse Drug Treatment

C646 (Selleckchem, #S7152) was reconstituted in 10% DMSO (Sigma) dissolved in PBS, and administered daily by intraperitoneal (IP) injection at dose of 5 mg/kg/day. Treatment was initiated at 8 weeks of age and continued for 12 weeks. 10% DMSO in PBS was administered as a control.

Mouse Echocardiography

Nair hair removal cream was used to remove fur from the anterior thorax of the mice the day prior to echocardiography. According to previously described with slight modifications (1), all echocardiography were performed on mice that were awake and unsedated with the use of the Vevo 2100 imaging system and 40 MHz transducer (Visualsonics). Mice were imaged at 8 weeks of age as a baseline and every 4 weeks thereafter, until 20 weeks of age. Mice aorta were imaged in the parasternal long-axis view. Three separate measurements of the maximal internal dimension at the sinus of Valsalva during systole were made in separate cardiac cycles and averaged. All imaging and analysis was performed blinded to genotype and treatment arm.

Mouse Blood Pressure

According to previously described with slight modifications (1), blood pressure was measured by tail cuff plethysmography with using a Harvard Apparatus IITC Non-Invasive tail cuff device. Mice were placed in a standard acrylic restrainer for adult mice, internal diameter 25 mm with an adjustable head gate, and the end plate was removable, allowing the mice to walk into the restrainer without force. Hemodynamic recordings were made without sedation or anesthesia. Blood pressure was measured at the end of drug trial. Mice were habituated for 4 days. On the 5$^{th}$ day, 10 blood pressures were obtained and averaged.

Mouse Radiography

According to previously described protocols with slight modifications (1), Mice were anesthetized using a combination of 50 mg/kg of ketamine-HCl and 5mg/kg xylazine-HCl by intraperitoneal (IP) injection before X-ray imaging. Mice were placed in the left lateral decubitus position on a radiolucent platform with metal paper clip as a scale bar and imaged at 1x magnification using a Faxitron MX20 (Faxitron).

Mouse Aorta Histological Analysis

According to previously described protocols with slight modifications (1), latex-infused heart and aorta were removed from body and transected just below the level of the aortic annulus, and just above aortic root, and 2-3 mm transverse sections were mounted in 4% agar prior to paraffin fixation. Five micron aortic sections underwent Verhoeff-van Giesen (VVG) and Masson's Trichrome staining, and were imaged 40× magnification, using a Nikon Eclipse E400 microscope. Aortic wall thickness was measured of four sites of four representative sections for each mouse and the disruptions of elastin fiber architecture were counted in four sections every 25 micron from aortic annulus. All analyses were performed blinded to genotype and treatment arm and the results were averaged.

Mouse Behavioral Test

Behavioral tests were performed as per manufacturer's manual. All of behavioral tests were performed at 10 weeks of age. For open field test, mice were placed into one of the corners of each 45×45 cm open filed chambers (San Diego Instruments) with a 16×16 photobeam configuration and their behavior was monitored for 5 minutes per each cycle of 6 cycles (total 30 minutes). Mice activity in center area and/or peripheral activities were recorded by all beam interruptions. Total activity was calculated by add up all beam interruptions during the cycles and center activity and peripheral activity were calculated by add up beam interruptions at center area and peripheral area respectively. For rotarod test, mice were placed on a horizontally oriented, rotating cylinder (rod) suspended above cage floor of Rotamex 5 rotarod (Columbus Instruments). The acceleration started at 0 rpm and increased by 1.0 rpm for every 5 seconds. Velocity and time were recorded at time of falling for three measurements. Mice had 3 minutes of rest time between each trials. All analyses were performed blinded to genotype and the results were averaged.

Human Cell Culture

Primary human dermal fibroblasts were derived from forearm skin biopsies of two controls and two patients with Shprintzen-Goldberg syndrome from previously described. The fibroblasts were cultured in Dulbecco's modified eagle medium (DMEM) with 10% fetal bovine serum (FBS) in the presence of antibiotics and passaged confluence. According to previously described protocols with slight modifications (2), all cell culture experiments were conducted in serum-starved media for 24 hours prior to drug treatment. Stimulation was performed using 10 ng/ml recombinant human TGFβ1 (R&D system). C646 dissolved in DMSO was treated at a dose of 2004 for 24 hours of pre-treated before TGFβ1 stimulation and SD208 dissolved in DMSO was treated at a dose of 10 μM for 24 hours of pre-treated before TGFβ1 stimulation. Cells were collected at baseline, 6 hours after TGFβ1 stimulation. RNA was extracted from the cells using Trizol (ThermoFisher) by RNeasy mini kit (QIAGEN), as per the manufacturer's manual.

Quantitative RT-PCR Expression Analysis

Total RNA was isolated from mouse aortas or cultured cells by RNeasy mini kit (QIAGEN), as per the manufacturer's manual. Quantitative PCR was performed in triplicate with TaqMan Universal PCR Master Mix using an ABI Prism 7900 HT QPCR machine (all from Applied Biosystems), as per the manufacturer's manual. The following prevalidated TaqMan probes were used to detect specific transcripts: Mm00801666_g1 (Col1a1), Mm01254476_m1 (Col3A1), Mm01256744_m1 (Fn1), Mm04205640_g1 (Cdkn1a), Mm01192932_g1 (Ctgf), and Mm00435860_m1 (Serpine1), Mm00448744_m1 (Ski), Mm00456917_m1 (Skil), Mm00484742_m1 (Smad7) and Mm00607939_s1 (Actb) (Life Technologies). For human samples, the following probes were used: Hs00943809_m1 (COL3A1), Hs00365052_m1 (FN1), Hs00161707_m1 (SKI), Hs01045418_m1 (SKIL) and Hs01060665_g1 (ACTB). Reactions were run in triplicate, and relative quantification for each transcript was obtained by normalizing against housekeeping control transcript such as β-ACTIN (ACTB) according to the formula $2^{-Ct}/2^{-Ct(ACTB)}$.

Chromatin Immunoprecipitation Quantitative PCR Analysis

Chromatin Immunoprecipitation was performed using the EpiQuik Tissue Chromatin Immunoprecipitation (ChIP) Kit (Epigentek) with the following adjustments to the standard protocol. In brief, snap-frozen aortas were cross-linked in fresh 1% paraformaldehyde in PBS. Sonication was performed using a Bioruptor (Diagenode). The following antibody was used: H3K27ac (Abcam, ab4729). Primers are named after proximal putative target genes of the investigated enhancers. For each tested genomic element, a set of primers was used. Quantitative PCR primer sequences are Col3a1: 5'-AGGGAAGCCAAACTTTTTCC-3' (sense; SEQ ID NO: 3), and 5'-GAGACTCTTTGTGCAAAAGA-3'(antisense; SEQ ID NO: 4) and Fn1: 5'-GGAGGTG-GAGATGGACTGTA-3' (sense; SEQ ID NO: 5) and 5'-CGGCATTAACTCTGTACTGT-3' (antisense; SEQ ID NO: 6). Quantitative analysis was performed with Fast SYBR Green Master Mix (ThermoFisher) using an ABI Prism 7900 HT QPCR machine (Applied Biosystems). Reactions were run in triplicate, and the results were calculated as percentage of input.

Immunofluorescence Staining

Immunofluorescence staining was performed as previous described (3). Frozen 10 μm long-axis view sections were obtained with a cryostat and mounted on glass slides. Sections were dried for at room temperature for overnight prior to staining. Sections were permeabilized in staining buffer (PBS containing 0.1% Triton-X 100) for 30 minutes and then incubated with Fc Receptor Block from Innovex for 30 minutes at room temperature, washed briefly in staining buffer, and then incubated again in blocking solution (0.1% Triton-X 100, 1:50 goat serum, 0.3M glycine) for 30 minutes. Primary antibodies were diluted at 1:100 in staining buffer were performed prior to incubation goat anti-rabbit secondary antibody conjugated to Alexa Fluor 555 (Life Technologies) at 1:200 for 1 hour and then mounted with VECTASHIELD Hard Set Mounting Media with DAPI. Images were acquired on Zeiss AxioExaminer with 710NLO-Meta multiphoton confocal microscope at a 25× magnification. The following primary antibody was used: anti-H3K27ac (Abcam, ab4729).

RNA in situ Hybridization

Frozen 10 μM long-axis view sections were obtained with a cryostat and mounted on glass slides. RNA in situ hybridization (ISH) assay was performed with RNAscope Fluorescent Multiplex Reagent Kit (Advanced Cell Diagnostics, Inc.), as per the manufacturer's manual. In brief, frozen sections were permeabilized in the buffer and CTGF RNA in the sections were hybridized with CTGF specific probes (Mm-CTGF-C2,#314541-C2). Hybridized probes were amplified with amplifiers and label probes provided by manufacturer and then mounted with VECTASHIELD Hard Set Mounting Media with DAPI. Images were acquired on Zeiss AxioExaminer with 710NLO-Meta multiphoton confocal microscope at a 40× magnification.

Statistical Analysis

All quantitative data are shown as bar graphs produced using Microsoft Excel. Mean±standard errors of the mean (SEM) are displayed. Statistical analyses were performed using two-tailed t tests. Additional statistical analyses included use of two-way ANOVA to assess whether there was a significant interaction between the genotype of the mice and the medication effect. A p-value <0.05 was considered statistically significant for all tests.

REFERENCES

1) Holm, T. M. et al. Noncanonical TGF signaling contributes to aortic aneurysm progression in Marfan syndrome mice. *Science* 332, 358-361 (2011).

2) Doyle, A. J et al. Mutations in the TGF-β repressor SKI cause Shprintzen-Goldberg syndrome with aortic aneurysm. *Nat Genet.* 44, 1249-1254 (2012).

3) Gallo, E M et al. Angiotensin II-dependent TGF-β signaling contributes to Loeys-Dietz syndrome vascular pathogenesis. *J Clin Invest.* 124, 448-460 (2014).

What is claimed is:

1. A method for treating an aortic aneurysm syndrome in a subject in need thereof, the method comprising administering to the subject an effective amount of an HAT inhibitor selected from C646, anacardic acid, garcinol, isothiazol-3(2H)-one, 2-quinolone, 4-quinolone, CPTH2, MC2884, SPV106, L002, windorphen, PU-139, PU-141, TH1834, A-485, I-CBP112, CTPB, MG149, EML, ISOX, Lys-CoA, and SGC-CBP30, or a pharmaceutically acceptable salt thereof, thereby treating the aortic aneurysm in the subject.

2. The method of claim 1, wherein the HAT inhibitor is C646.

3. The method of claim 1, wherein the aortic aneurysm is a transforming growth factor β (TGFβ) induced aortic aneurysm.

4. The method of claim 1, wherein the aortic aneurysm is selected from Shprintzen-Goldberg syndrome (SGS), Marfan syndrome (MFS), Loeys-Dietz syndrome (LDS), Ehlers-Danlos syndrome (EDS), familial aortic dissection, or annuloaortic ectasia.

5. The method of claim 1, wherein the subject is a mammal.

6. The method of claim 5, wherein the mammal is a human.

7. The method of claim 1, wherein administering is via systemic administration.

8. The method of claim 1, wherein the effective amount is a therapeutically effective amount.

* * * * *